United States Patent
Schuster et al.

(10) Patent No.: US 9,144,573 B2
(45) Date of Patent: Sep. 29, 2015

(54) PROSTAGLANDIN TRANSPORTER INHIBITORS

(75) Inventors: Victor L. Schuster, New York, NY (US); Yuling Chi, Bronx, NY (US); Young-Tae Chang, Singapore (SG); Jaeki Min, Marietta, GA (US)

(73) Assignees: Albert Einstein College of Medicine of Yeshiva University, Bronx, NY (US); New York University, New York, NY (US)

( * ) Notice: Subject to any disclaimer, the term of this patent is extended or adjusted under 35 U.S.C. 154(b) by 386 days.

(21) Appl. No.: 13/555,408

(22) Filed: Jul. 23, 2012

(65) Prior Publication Data
US 2013/0171171 A1    Jul. 4, 2013

Related U.S. Application Data

(63) Continuation of application No. 12/227,267, filed as application No. PCT/US2007/011693 on May 15, 2007, now Pat. No. 8,227,466.

(60) Provisional application No. 60/801,440, filed on May 17, 2006.

(51) Int. Cl.
*A61K 31/53* (2006.01)
*A61K 31/713* (2006.01)
*C07D 251/54* (2006.01)
*G01N 33/68* (2006.01)

(52) U.S. Cl.
CPC .............. *A61K 31/53* (2013.01); *A61K 31/713* (2013.01); *C07D 251/54* (2013.01); *G01N 33/68* (2013.01)

(58) Field of Classification Search
CPC ..... A61K 31/53; A61K 31/713; C07D 251/54
USPC .................... 514/245, 242; 544/196
See application file for complete search history.

(56) References Cited

U.S. PATENT DOCUMENTS

| | | |
|---|---|---|
| 5,792,851 A | 8/1998 | Schuster et al. |
| 8,227,466 B2 | 7/2012 | Schuster et al. |
| 2004/0209881 A1 | 10/2004 | Timmer et al. |
| 2004/0225125 A1 | 11/2004 | Chang |
| 2009/0233933 A1 | 9/2009 | Schuster et al. |

OTHER PUBLICATIONS

Communication pursuant to Article 94(3) EPC regarding corresponding European Application No. 07794912.1-2123 dated Dec. 9, 2009.
European Search Report regarding corresponding European Application No. 07794912.1-2123 dated Nov. 10, 2009.
Chi, et al. "Identification of a New Class of Prostaglandin Transporter Inhibitors and Characterization of Their Biological Effects on Prostaglandin E2 Transport." The Journal of Pharamcology and Experimental Therapeutics 2006 vol. 316, No. 3 JPET 316:1346-1350.
The International Preliminary Report on Patentability for PCT Application No. PCT/US2007/011693.
Chi, et al. "Identification of a New Class of Prostaglandid Transporter Inhibitors and Characterization of Their Biological Effects on Prostaglandin E2 Transport." Journal of Pharmacology and Experimental Therapeutics, 2005, 316:1346-1350, pp. 1346-1347; Abstract; Fig. 1-3.
The International Search Report as published under WO 2007/136638 A3.
The Written Opinion for PCT Application No. PCT/US2007/011693.
The International Preliminary Report on Patentability Report on Patentability for PCT/US2007/011693.
European Office Action dated Jan. 17, 2012 corresponding to European Patent Application No. 0779412-2123.

*Primary Examiner* — Jennifer M Kim
(74) *Attorney, Agent, or Firm* — Amster, Rothstein & Ebenstein LLP

(57) ABSTRACT

The present invention generally relates to prostaglandin transport. More specifically, the invention is directed to compounds that inhibit prostaglandin transport and subsequent COX-2 induction, and methods relating thereto.

6 Claims, 27 Drawing Sheets

| Time (min) | Δ[PGE2] (nM) | $V_i$ (fmoles/s) |
|---|---|---|
| 3 | 12.884 | 0.19217 |
| 6 | 17.754 | 0.24083 |
| 9 | 25.120 | 0.32091 |
| 20 | 19.915 | 0.24794 |
| 35 | 14.189 | 0.19359 |

|  | Inhibition |
|---|---|
| TGBz M52 | 40% |
| TGBz M54 | 46% |
| TGBz H55 | 34% |

Screening of PGT Inhibitors In Cell Culture

The best inhibitor to date:

TGBz T26    $K_i$ = 300 nM
(competitive inhibition)

With Y-T Chang, NYU

PROSTAGLANDIN TRANSPORTER INHIBITORS

CROSS-REFERENCE TO RELATED APPLICATION

This application is a continuation of U.S. Ser. No. 12/227,267, filed Mar. 11, 2009, now U.S. Pat. No. 8,227,466, issued Jul. 24, 2012, a §371 U.S. national phase of PCT Application No. PCT/US2007/011693, filed May 15, 2007, which claims the benefit of U.S. Provisional Application No. 60/801,440, filed May 17, 2006.

STATEMENT REGARDING FEDERALLY SPONSORED RESEARCH OR DEVELOPMENT

This invention was made with government support under grant numbers R01DK049688, P50DK064236 and R01CA096912 awarded by the National Institutes of Health. The government has certain rights in the invention.

BACKGROUND OF THE INVENTION (1) Field of the Invention

The present invention generally relates to prostaglandin transport. More specifically, the invention is directed to compounds that inhibit prostaglandin transport and subsequent COX-2 induction, and methods relating thereto.

(2) Description of the Related Art

Prostaglandins (PGs) are synthesized from arachidonic acid by cyclooxygenases (COX1 and COX2) and corresponding synthases (Helliwell et al., 2004). PGs play an important role in physiology and clinical settings. Their biological effects include triggering inflammation, fever and pain (Blatteis and Sehic, 1997; Bley et al., 1998; Vanegas and Schaible, 2001; Samad et al., 2002); induction of labor (Ulmann et al., 1992); modulation of renal hemodynamics and of water and solute reabsorption (Epstein, 1986; Wang et al., 1998; Yokoyama et. al., 2002); and arterial vasodilatation (Clyman et. al., 1978; Coceani and Olley, 1988; Smith et al., 1994). PG analogues, such as latanoprost and unoprostone, have been used to treat glaucoma (Stjernschantz, 1995; Alm, 1998; Susanna et al., 2002; Stjernschantz, 2004). At the cellular level, PGs are involved in several major signaling pathways, including the MAP kinase and protein kinase A pathways by upregulation of cAMP (Narumiya et al., 1999; Bos et al., 2004).

The magnitude of PG effects depends not only on their production but also their metabolism. The prostaglandin transporter (PGT) (Kanai et al., 1995) removes PGs from the extracellular compartment and thereby terminates their interactions with receptors on cell membranes. PGT delivers PGs to cytoplasmic 15-OH PG dehydrogenase (Schuster, 2002; Nomura et al., 2004), resulting in oxidation and inactivation.

Because PGT is highly expressed in the tissues and organs where PGs are synthesized (Bao et al., 2002), and because PGT regulates a broad and complex PG signaling system, an inhibitor of PGT would be important for manipulating signaling. Known PGT blockers include inhibitors of the organic anion transporters (OATs), such as bromcresol green and bromosulfophthalein, and some COX2 inhibitors, such as indomethacin and ibuprofen (Bito and Salvador, 1976; Kanai et al., 1995). One of the main problems with these inhibitors is that they are not specific for PGT (Jacquemin et al., 1994; Sweet et al., 1997).

It would thus be desirable to identify specific PGT inhibitors. The present invention addresses that need.

SUMMARY OF THE INVENTION

Accordingly, the inventors have identified compounds that inhibit mammalian prostaglandin transporter (PGT) activity. These compounds are useful, e.g., in the treatment of disorders that are at least partially mediated by excessive PGT activity.

Thus, the present invention is directed to methods of inhibiting prostaglandin transporter (PGT) activity in mammals. The methods comprise administering a compound to the mammal effective to inhibit PGT activity. In these methods, the compound has Formula 1:

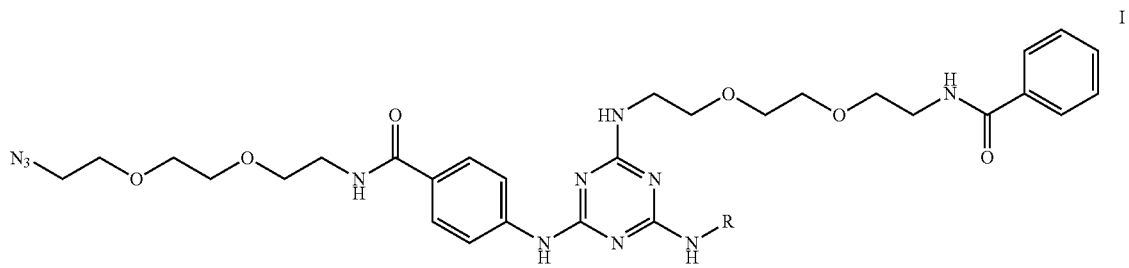

or, a pharmaceutically acceptable salt, ester, or tautomer thereof, wherein R is a $C_1$-$C_{15}$ straight or branched alkyl, a substituted alkyl, a cycloalkyl, a carboxyalkyl, a substituted cycloalkyl, a $C_1$-$C_{15}$ straight or branched alkenyl, a substituted alkenyl, a cycloalkenyl, a substituted cycloalkenyl, a $C_1$-$C_{15}$ straight or branched alkinyl, a substituted alkinyl, a cycloalkinyl, a substituted cycloalkinyl, a $C_1$-$C_{10}$ straight or branched ether, a substituted ether, a cycloether, an ester, an amide, an acetyl, an aminal, an anhydride, an aryl, a substituted aryl, a heteroaryl, a substituted heteroaryl, a carboxyaryl, a heterocyclic group, a substituted heterocyclic group, a fused cycloalkyl, a substituted fused cycloalkyl, a fused heterocyclic group, a substituted fused heterocyclic group, a fused aryl, a substituted fused aryl, a fused heteroaryl, a substituted fused heteroaryl ring, or any combination thereof, optionally further comprising a hydroxy, an alkoxy, an aryloxy, an oxo, an ester, an ether, an amine, an azo, an azido, a nitro, an imine, an isothionate, a carbonyl, a peroxide, a halogen, a formyl, an acyl, a carboxy, an amido, a carbamoyl, a guanidino, a ureido, a amidino, a thiol, a mercapto, a sulfinyl, a sulfonyl and/or a sulfonamide.

The invention is also directed to methods of determining whether a test compound is an inhibitor of a prostaglandin transporter. These methods comprise contacting the test compound with the prostaglandin transporter, then determining whether the prostaglandin transporter has less transporter activity when contacted with the test compound than when no so contacted. The test compound in these methods is

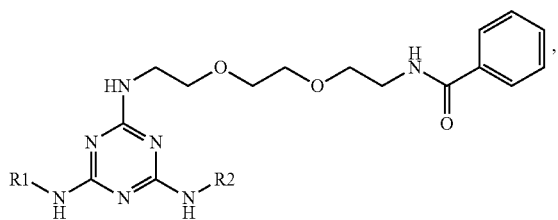

or a pharmaceutically acceptable salt, ester, or tautomer thereof, wherein R1 and R2 are independently a $C_1$-$C_{15}$ straight or branched alkyl, a substituted alkyl, a cycloalkyl, a carboxyalkyl, a substituted cycloalkyl, a $C_1$-$C_{15}$ straight or branched alkenyl, a substituted alkenyl, a cycloalkenyl, a substituted cycloalkenyl, a $C_1$-$C_{15}$ straight or branched alkinyl, a substituted alkinyl, a cycloalkinyl, a substituted cycloalkinyl, a $C_1$-$C_{10}$ straight or branched ether, a substituted ether, a cycloether, an ester, an amide, an acetyl, an aminal, an anhydride, an aryl, a substituted aryl, a heteroaryl, a substituted heteroaryl, a carboxyaryl, a heterocyclic group, a substituted heterocyclic group, a fused cycloalkyl, a substituted fused cycloalkyl, a fused heterocyclic group, a substituted fused heterocyclic group, a fused aryl, a substituted fused aryl, a fused heteroaryl, a substituted fused heteroaryl ring, or any combination thereof, optionally further comprising a hydroxy, an alkoxy, an aryloxy, an oxo, an ester, an ether, an amine, an azo, an azido, a nitro, an imine, isothionate, a carbonyl, a peroxide, a halogen, a formyl, an acyl, carboxy, an amido, a carbamoyl, a guanidino, a ureido, a amidino, a thiol, a mercapto, a sulfinyl, a sulfonyl and/or a sulfonamide.

The invention is further directed to compounds that inhibit prostaglandin transporter activity. These compounds are

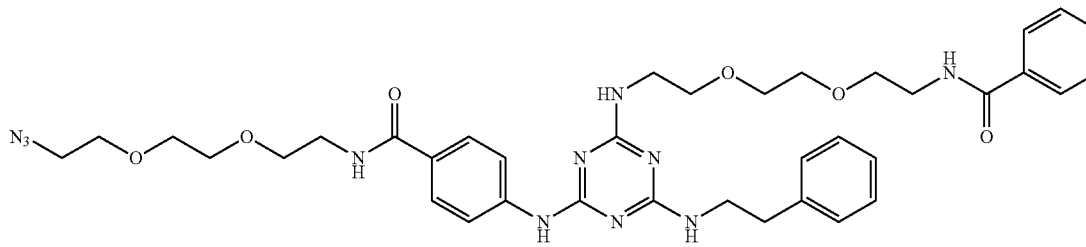

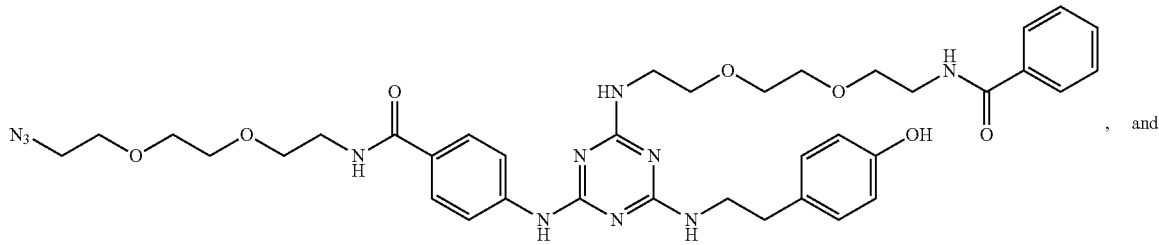

, and

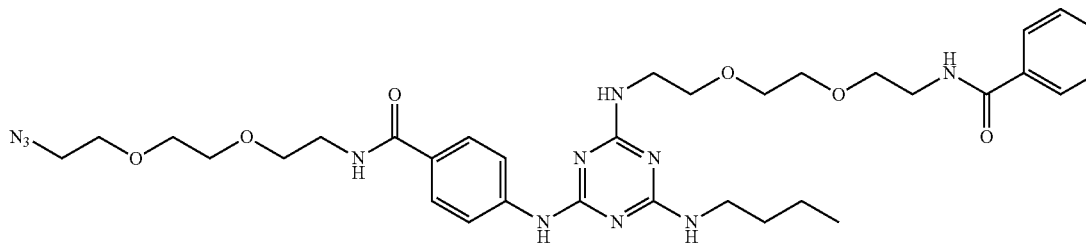

.

The invention is additionally directed to pharmaceutical compositions comprising any of the above compounds in a pharmaceutically acceptable excipient.

The invention is further directed to methods of inhibiting prostaglandin transporter (PGT) activity in a mammal. The methods comprise administering a compound to the mammal effective to inhibit PGT activity. In these methods, the compound is

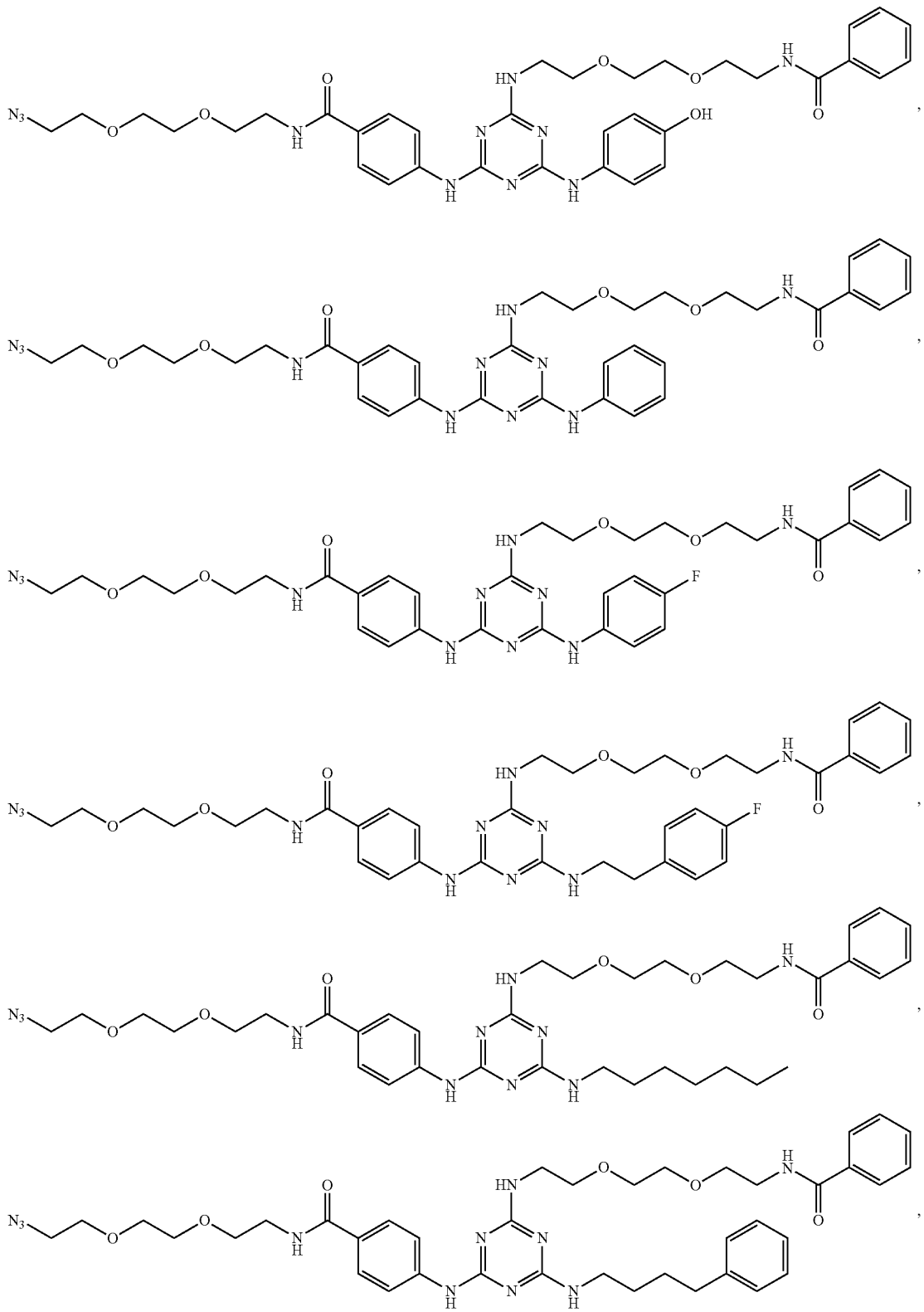

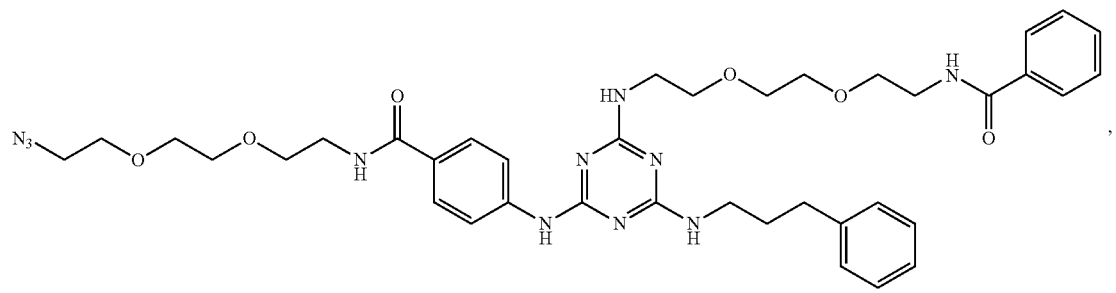
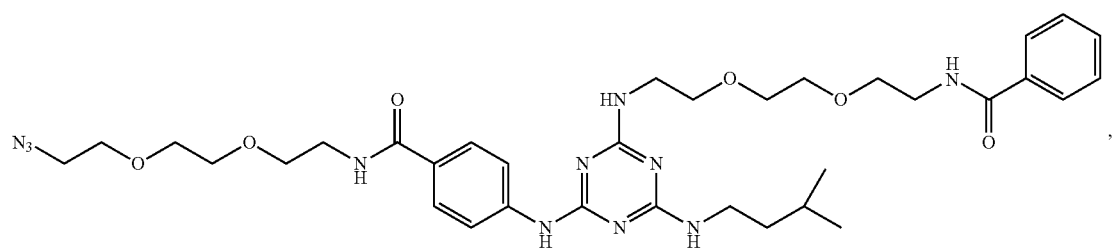
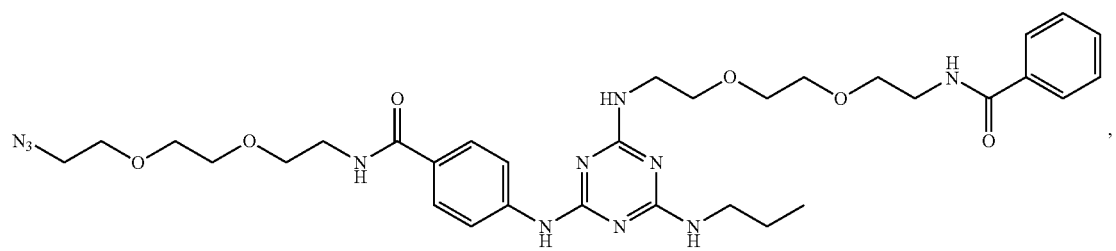
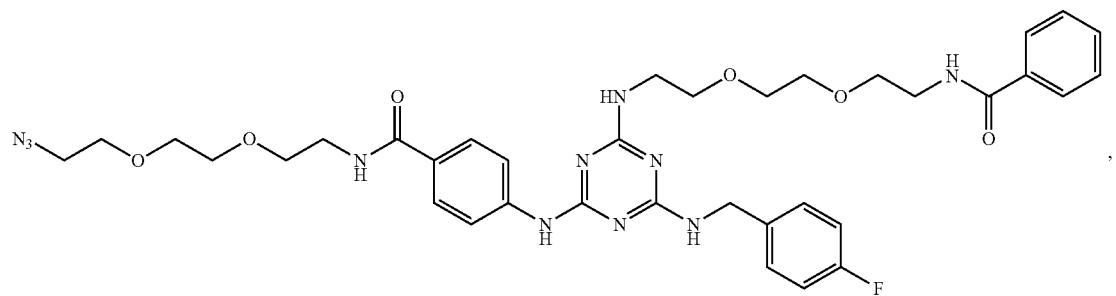
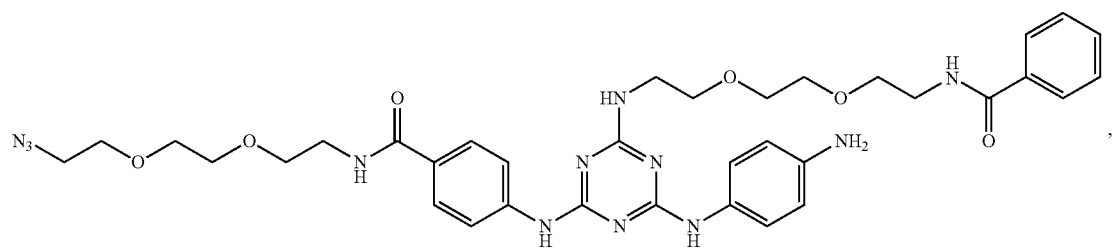
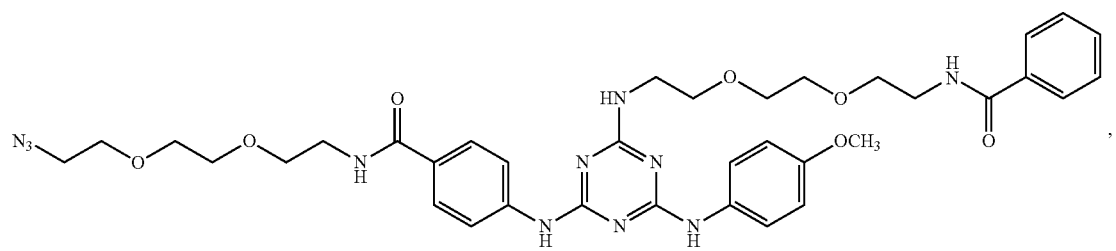

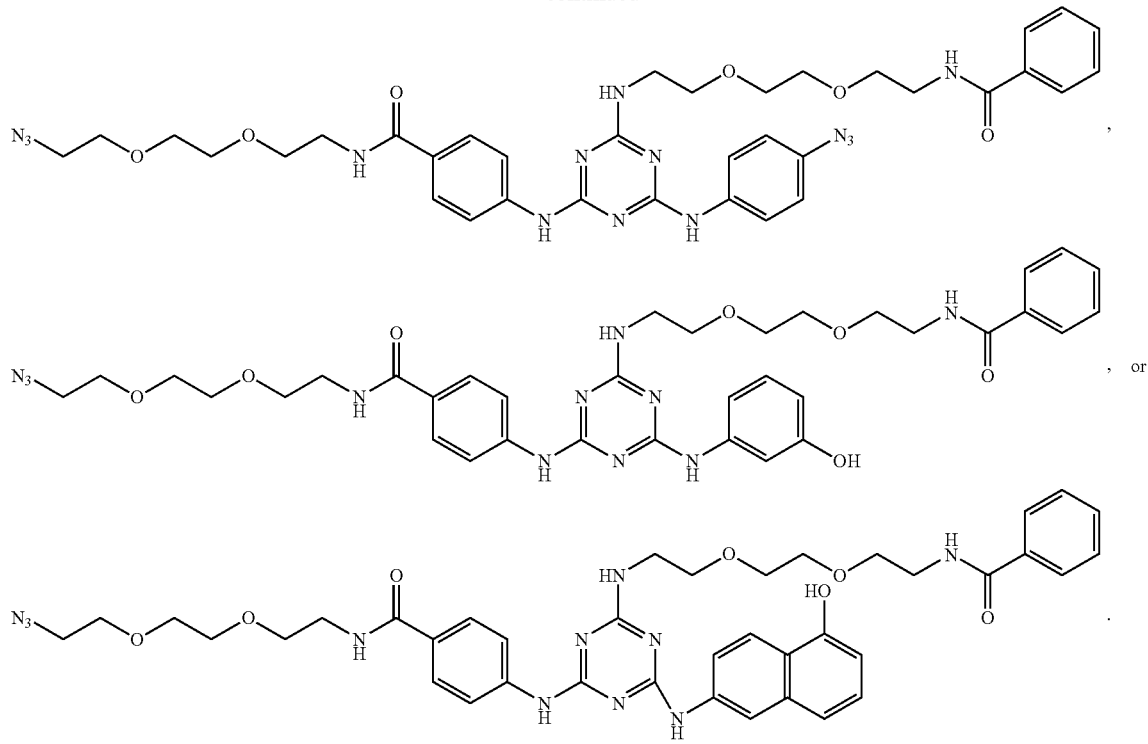

Additionally, the invention is directed to methods of determining whether a test compound is an inhibitor of a prostaglandin transporter. The methods comprise contacting the test compound with the prostaglandin transporter, then determining whether the prostaglandin transporter has less transporter activity when contacted with the test compound than when not so contacted. In these methods, the test compound is

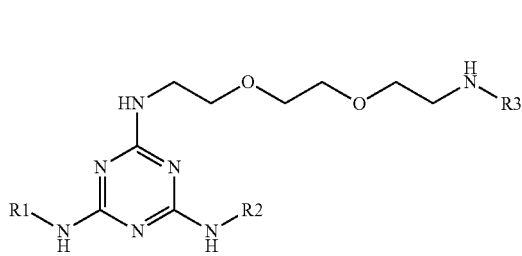

or a pharmaceutically acceptable salt, ester, or tautomer thereof, wherein R1, R2 and R3 are independently a $C_1$-$C_{15}$ straight or branched alkyl, a substituted alkyl, a cycloalkyl, a carboxyalkyl, a substituted cycloalkyl, a $C_1$-$C_{15}$ straight or branched alkenyl, a substituted alkenyl, a cycloalkenyl, a substituted cycloalkenyl, a $C_1$-$C_{15}$ straight or branched alkinyl, a substituted alkinyl, a cycloalkinyl, a substituted cycloalkinyl, a $C_1$-$C_{10}$ straight or branched ether, a substituted ether, a cycloether, an ester, an amide, an acetyl, an aminal, an anhydride, an aryl, a substituted aryl, a heteroaryl, a substituted heteroaryl, a carboxyaryl, a heterocyclic group, a substituted heterocyclic group, a fused cycloalkyl, a substituted fused cycloalkyl, a fused heterocyclic group, a substituted fused heterocyclic group, a fused aryl, a substituted fused aryl, a fused heteroaryl, a substituted fused heteroaryl ring, or any combination thereof; optionally further comprising a hydroxy, an alkoxy, an aryloxy, an oxo, an ester, an ether, an amine, an azo, an azido, a nitro, an imine, an isothionate, a carbonyl, a peroxide, a halogen, a formyl, an acyl, a carboxy, an amido, a carbamoyl, a guanidino, a ureido, a amidino, a thiol, a mercapto, a sulfinyl, a sulfonyl and/or a sulfonamide, and wherein R3 is not

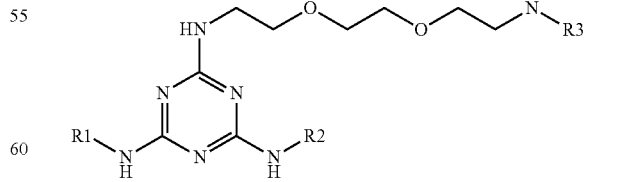

The invention is also directed to other methods of determining whether a test compound is an inhibitor of a prostaglandin transporter. These methods comprise contacting the test compound with the prostaglandin transporter, then determining whether the prostaglandin transporter has less transporter activity when contacted with the test compound than when no so contacted. Here, the test compound is

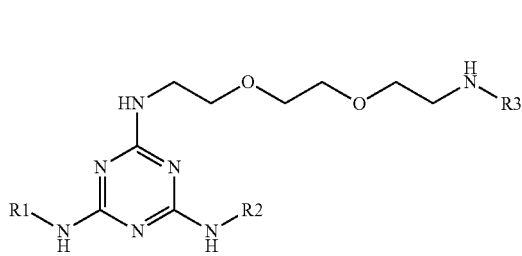

or a pharmaceutically acceptable salt, ester, or tautomer thereof, wherein R1 and R3 are independently a $C_1$-$C_{15}$ straight or branched alkyl, a substituted alkyl, a cycloalkyl, a carboxyalkyl, a substituted cycloalkyl, a $C_1$-$C_{15}$ straight or branched alkenyl, a substituted alkenyl, a cycloalkenyl, a substituted cycloalkenyl, a $C_1$-$C_{15}$ straight or branched alkinyl, a substituted alkinyl, a cycloalkinyl, a substituted cycloalkinyl, a $C_1$-$C_{10}$ straight or branched ether, a substituted ether, a cycloether, an ester, an amide, an acetyl, an aminal, an anhydride, an aryl, a substituted aryl, a heteroaryl, a substituted heteroaryl, a carboxyaryl, a heterocyclic group, a substituted heterocyclic group, a fused cycloalkyl, a substituted fused cycloalkyl, a fused heterocyclic group, a substituted fused heterocyclic group, a fused aryl, a substituted fused aryl, a fused heteroaryl, a substituted fused heteroaryl ring, or any combination thereof; optionally further comprising a hydroxy, an alkoxy, aryloxy, an oxo, an ester, an ether, an amine, an azo, an azido, a nitro, an imine, an isothionate, a carbonyl, a peroxide, a halogen, a formyl, an acyl, a carboxy, an amido, a carbamoyl, a guanidino, a ureido, a amidino, a thiol, a mercapto, a sulfinyl, a sulfonyl and/or a sulfonamide, and wherein R2 is

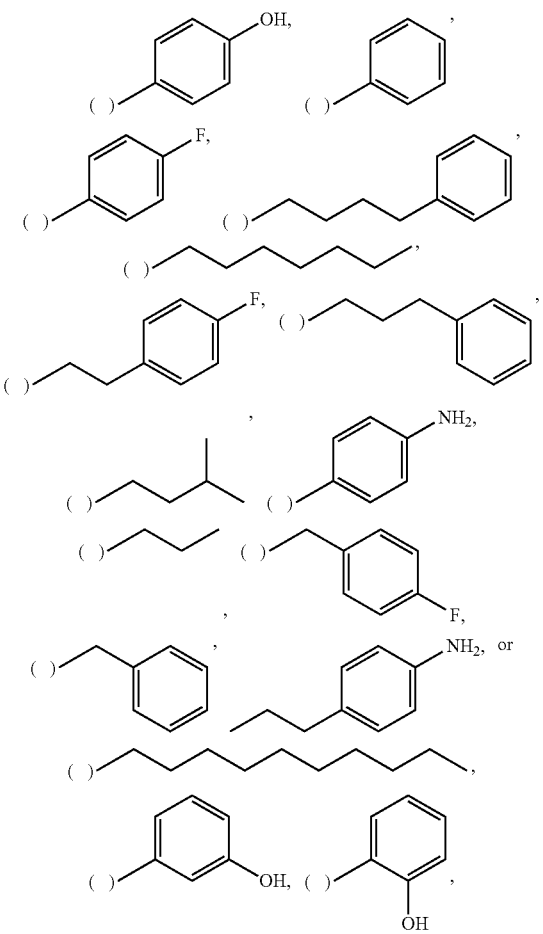

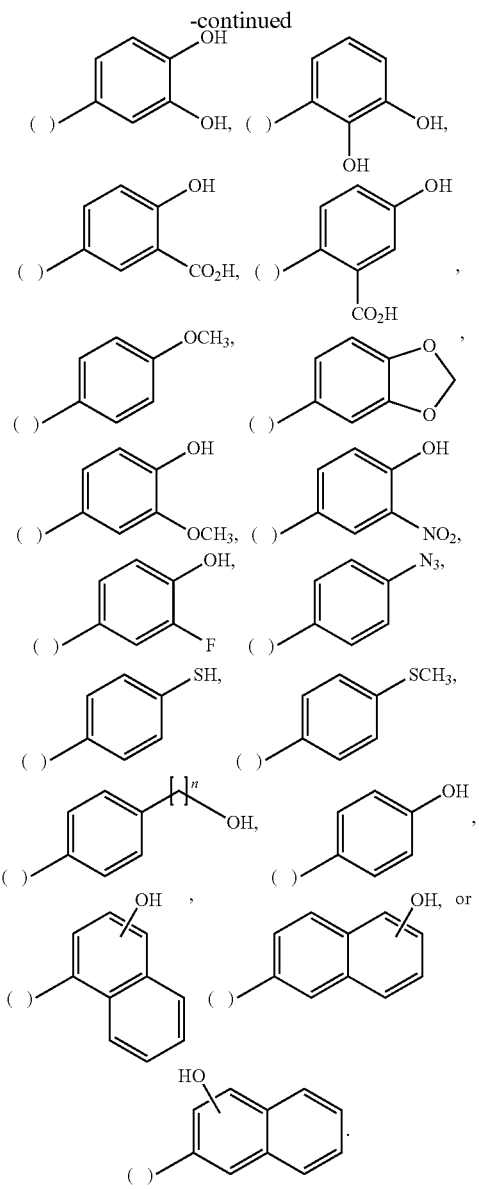

The invention is additionally directed to methods of inhibiting COX-2 in a mammal. The methods comprise administering an inhibitor of prostaglandin transporter activity to the mammal.

The present invention is further directed to methods of treating pain or inflammation in a mammal. The methods comprise administering an inhibitor of prostaglandin transporter activity to the mammal.

The invention is also directed to compounds that inhibit prostaglandin transporter activity, where the compound is

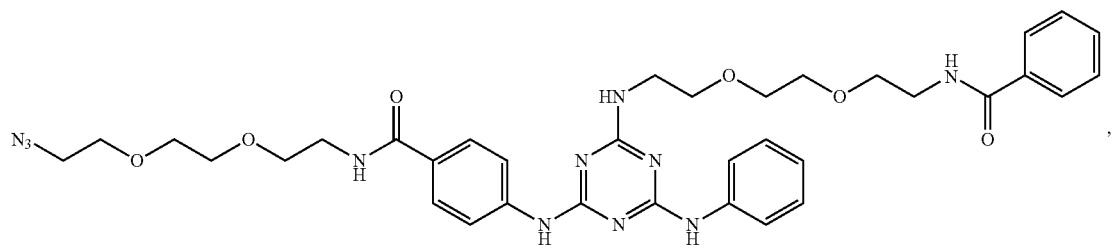,
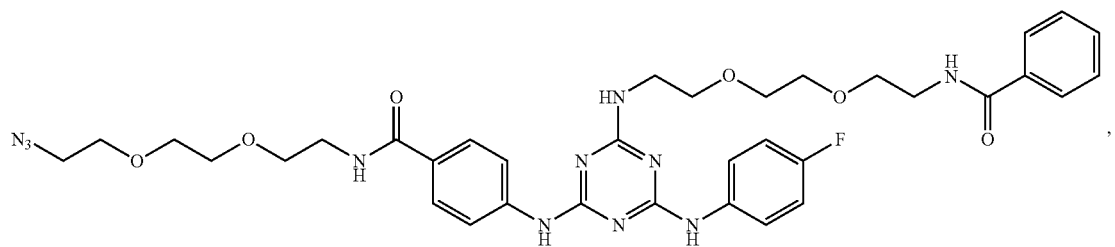,
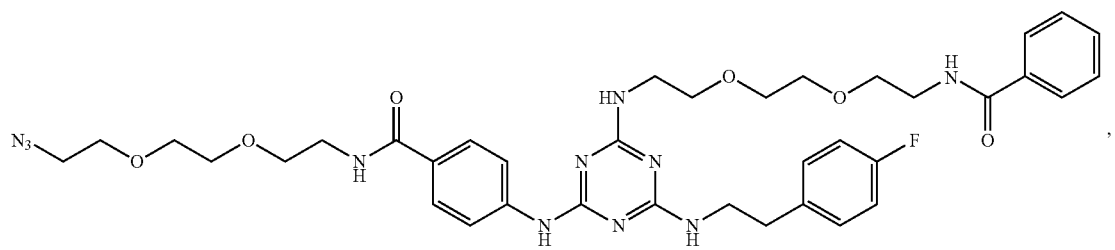,
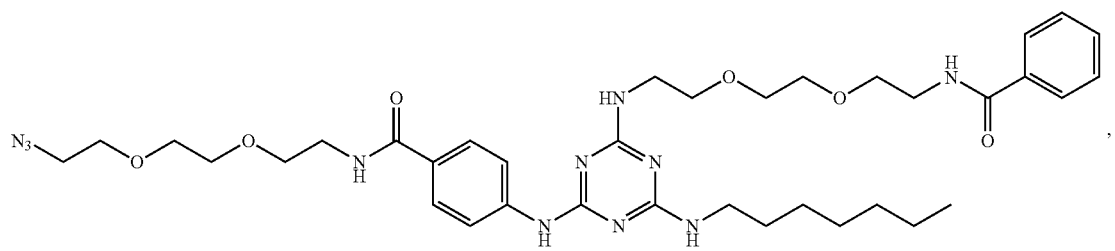,
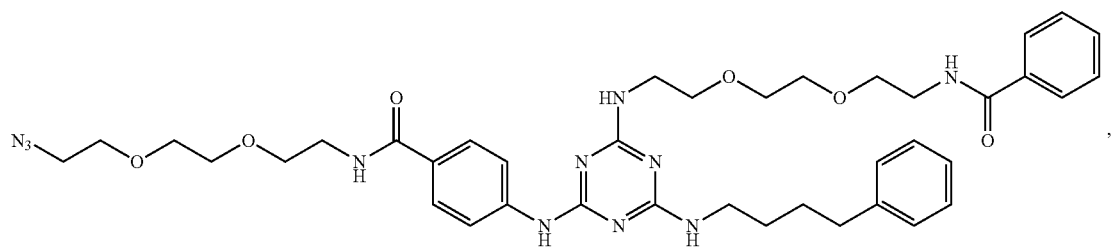,
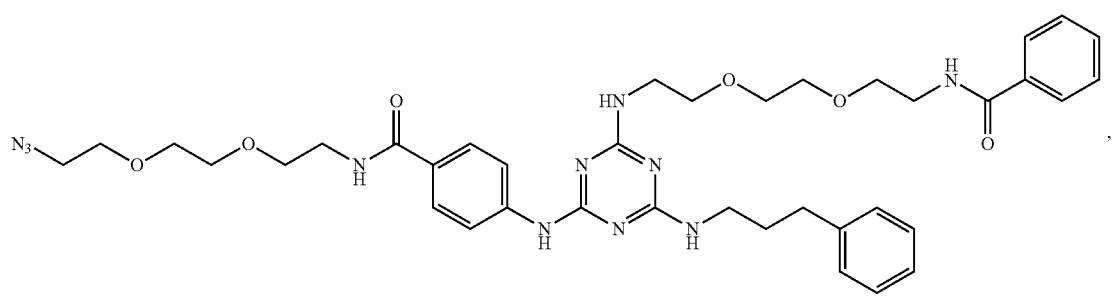,

-continued
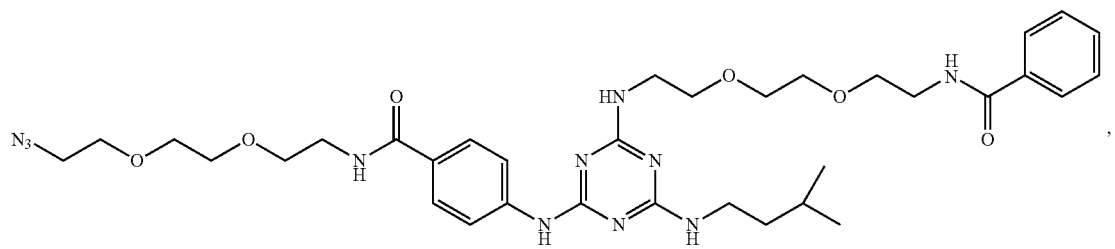
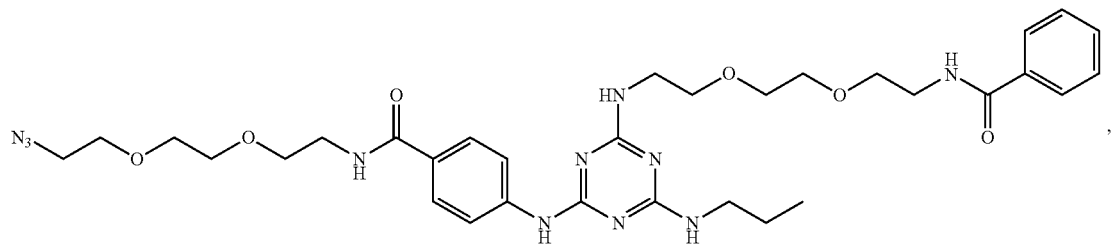
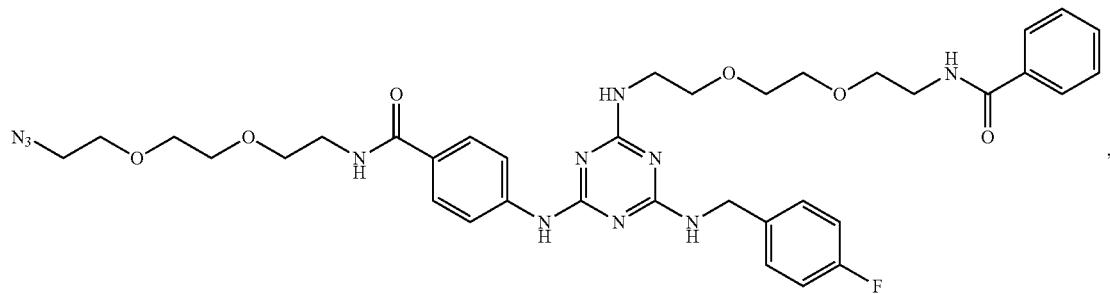
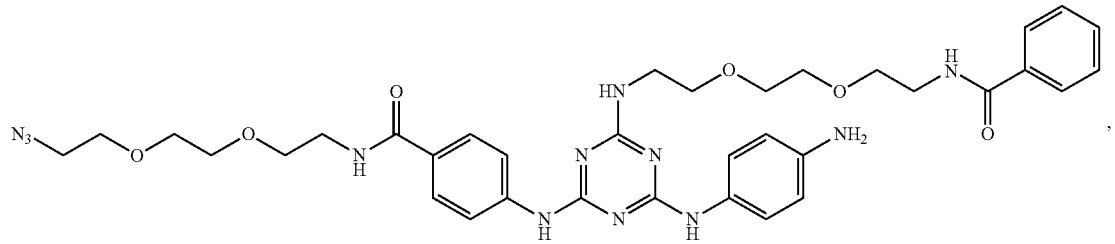
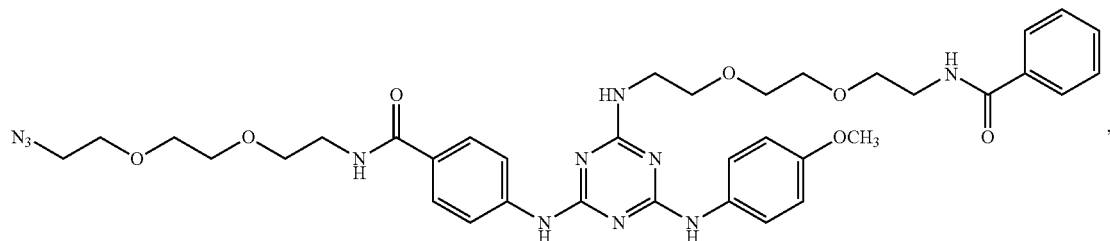
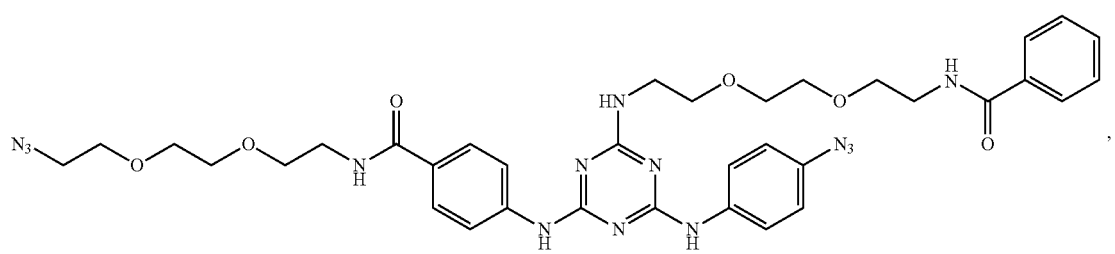

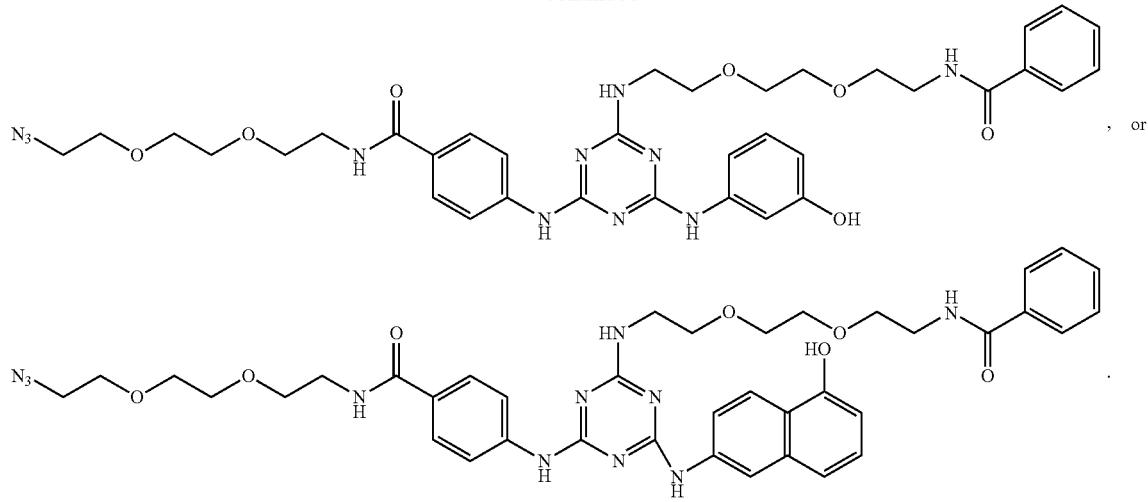

, or

The invention is further directed to pharmaceutical compositions comprising any of the above-described compounds in a pharmaceutically acceptable excipient.

Additionally, the invention is directed to the use of a COX-2-inhibiting effective amount of Compound I, or a pharmaceutically acceptable salt, ester, or tautomer thereof, for the manufacture of a medicament for the treatment of a disorder or condition at least partially mediated by COX-2 in a mammal. Here, Compound I is

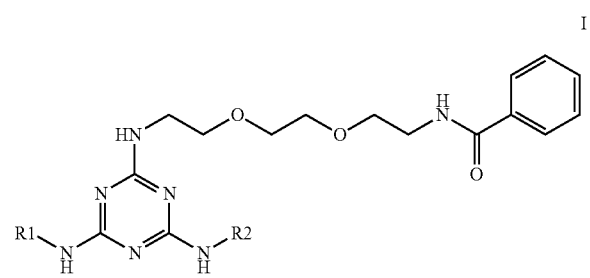

I or a pharmaceutically acceptable salt, ester, or tautomer thereof, wherein R is a $C_1$-$C_{15}$ straight or branched alkyl, a substituted alkyl, a cycloalkyl, a carboxyalkyl, a substituted cycloalkyl, $C_1$-$C_{15}$ straight or branched alkenyl, a substituted alkenyl, a cycloalkenyl, a substituted cycloalkenyl, a $C_1$-$C_{10}$ straight or branched alkinyl, a substituted alkinyl, a cycloalkinyl, a substituted cycloalkinyl, a $C_1$-$C_{10}$ straight or branched ether, a substituted ether, a cycloether, an ester, an amide, an acetyl, an aminal, an anhydride, an aryl, a substituted aryl, a heteroaryl, a substituted heteroaryl, a carboxyaryl, a heterocyclic group, a substituted heterocyclic group, a fused cycloalkyl, a substituted fused cycloalkyl, a fused heterocyclic group, a substituted fused heterocyclic group, a fused aryl, a substituted fused aryl, a fused heteroaryl, a substituted fused heteroaryl ring, or any combination thereof, optionally further comprising a hydroxy, an alkoxy, an aryloxy, an oxo, an ester, an ether, an amine, an azo, an azido, a nitro, an imine, isothionate, a carbonyl, a peroxide, a halogen, a formyl, acyl, a carboxy, an amido, a carbamoyl, guanidine, a ureido, a amidino, a thiol, a mercapto, sulfinyl, a sulfonyl and/or a sulfonamide.

DETAILED DESCRIPTION OF THE INVENTION

Figure 8:
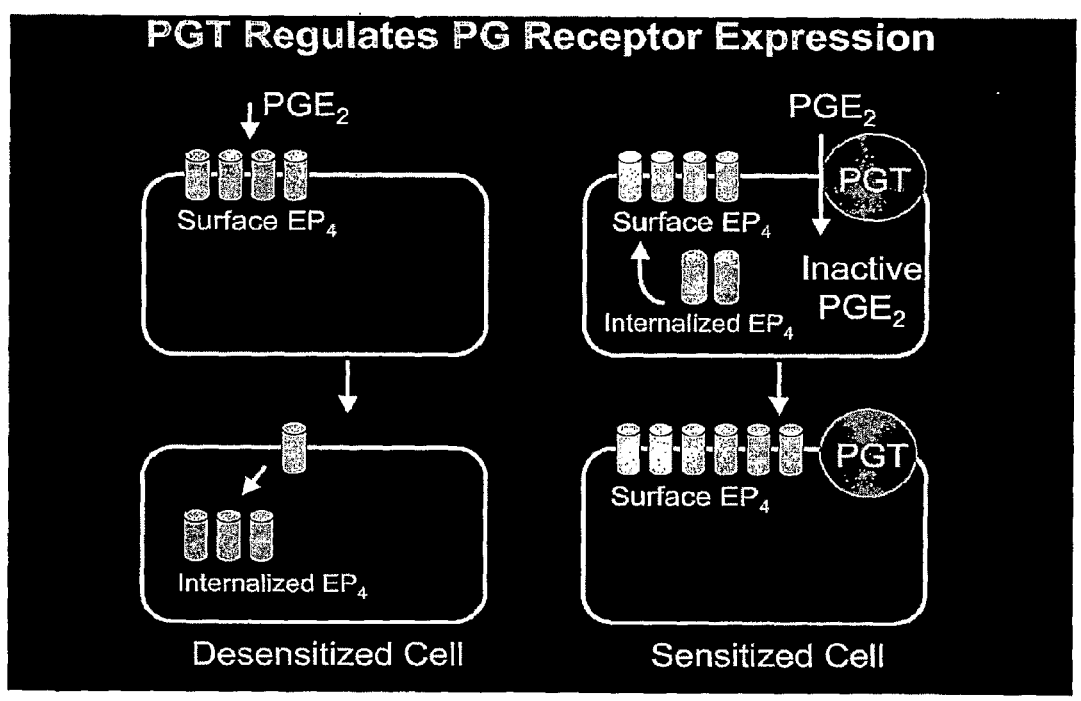
FIG. 8 is a diagram showing a model for PGT regulation of $PGE_2$ receptor (EP) expression.

Abbreviations
GFP, green fluorescence protein; MRP4, Multi Drug Resistance Protein 4; OAT, Organic Anion Transporter Accordingly, the inventors have identified compounds that inhibit mammalian prostaglandin transporter (PGT) activity. See Examples. These compounds are useful, e.g., in the treatment of disorders that are at least partially mediated by excessive PGT activity. Without being bound by any particular mechanism, it is believed that prostaglandin transport prevents prostaglandins from binding to EP$_4$ receptors on the cells surface (FIG. 8). That binding does take place if PGT is inhibited, causing the EP$_4$ receptors to become internalized and desensitizing the cell to later prostaglandin binding. Thus, inhibiting prostaglandin transport is believed to inhibit the effect of a subsequent exposure of the cell to induced prostaglandins by desensitizing cells to the prostaglandin effects.

Thus, the present invention is directed to methods of inhibiting prostaglandin transporter (PGT) activity in a mammal. The methods comprise administering a compound to the mammal effective to inhibit PGT activity. In these methods, the compound has Formula 1:

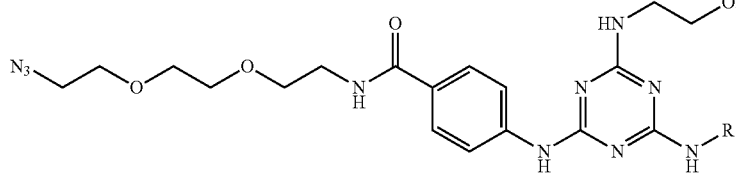
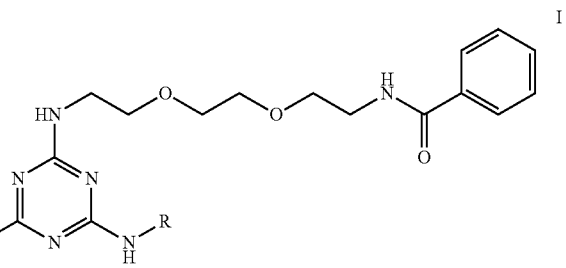

or a pharmaceutically acceptable salt, ester, or tautomer thereof, wherein R is a $C_1$-$C_{15}$ straight or branched alkyl, a substituted alkyl, a cycloalkyl, a carboxyalkyl, a substituted cycloalkyl, a $C_1$-$C_{15}$ straight or branched alkenyl, a substituted alkenyl, a cycloalkenyl, a substituted cycloalkenyl, a $C_1$-$C_{15}$ straight or branched alkinyl, a substituted alkinyl, a cycloalkinyl, a substituted cycloalkinyl, a $C_1$-$C_{10}$ straight or branched ether, a substituted ether, a cycloether, an ester, an amide, an acetyl, an aminal, an anhydride, an aryl, a substituted aryl, a heteroaryl, a substituted heteroaryl, a carboxyaryl, a heterocyclic group, a substituted heterocyclic group, a fused cycloalkyl, a substituted fused cycloalkyl, a fused heterocyclic group, a substituted fused heterocyclic group, a fused aryl, a substituted fused aryl, a fused heteroaryl, a substituted fused heteroaryl ring, or any combination thereof, optionally further comprising a hydroxy, an alkoxy, an aryloxy, an oxo, an ester, an ether, an amine, an azo, an azido, a nitro, an imine, an isothionate, a carbonyl, a peroxide, a halogen, a formyl, an acyl, a carboxy, an amido, a carbamoyl, a guanidino, a ureido, a amidino, a thiol, a mercapto, a sulfinyl, a sulfonyl and/or a sulfonamide.

As used herein, unless otherwise specifically designated, a "substituted" moiety is a moiety that further comprises a halogen (F, Cl, Br, or I), a hydroxy, a $C_1$-$C_3$ alkyl, a $C_1$-$C_3$ alkoxy, an azido, an amino, a nitro, a keto, a formyl, an azo, a carbonyl, a carboxy, an amido, a carbamoyl, a thiol, a mercapto, a sulfinyl, or a sulfonyl.

Preferably, R comprises a carboxyl or phenol group. More preferably, R is a $C_1$-$C_{10}$ straight or branched alkyl, a phenyl, a fused aryl, a fused heteroaryl, or any combination thereof, optionally substituted with a halogen, a carboxyl, an amino, a nitro, a SCH$_3$, a hydroxyl, a $C_1$-$C_3$ alkoxy, $C_1$-$C_3$ straight or branched alkyl, an azido, or a combination thereof. Even more preferably, R is a $C_1$-$C_5$ straight or branched alkyl, a phenyl, a fused aryl, or a combination of a $C_1$-$C_5$ straight or branched alkyl and a phenyl, optionally substituted with a halogen, one or more hydroxyls, a methoxy, a nitro, a carboxy, or a combination thereof. Still more preferably, R is

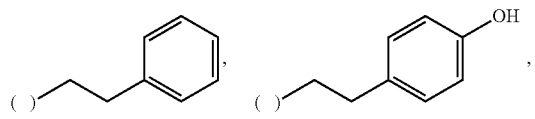

-continued

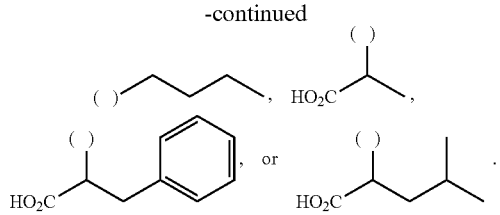

Most preferably, the compound is

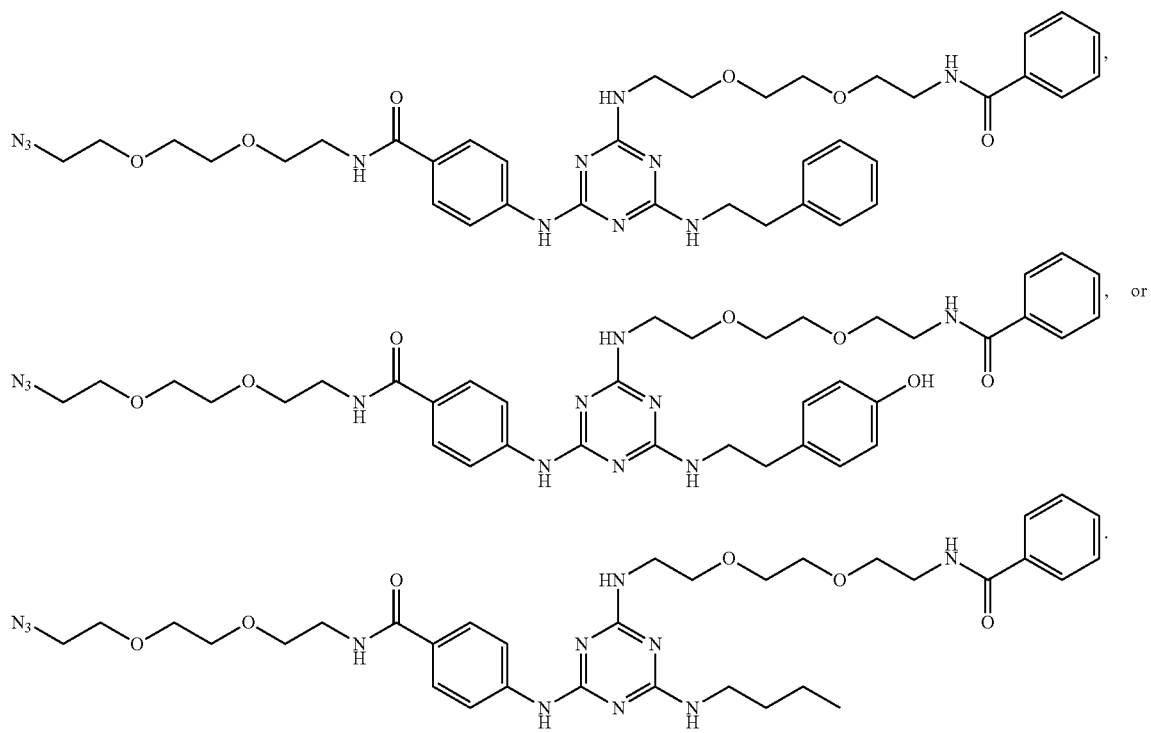

The inventors have also discovered that inhibiting prostaglandin transport inhibits COX-2 expression. See Example 2. Thus, the mammal in these methods is preferably a human suffering from a disease or disorder at least partially mediated by a cyclooxygenase-2. More preferably, the disease or disorder involves pain and/or inflammation. Non-limiting examples of diseases or disorders at least partially mediated by a cyclooxygenase-2 are arthritis, fever, common cold, hypertension, glaucoma, slow wound healing, slow initiation of labor, dysmenorrhea, menstrual cramps, inflammatory bowel disease. Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer, tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis, aortic aneurysm, periarteritis nodosa, congestive heart failure, myocardial infarction, stroke, cerebral ischemia, head trauma, spinal cord injury, neuralgia, neurodegenerative disorders, autoimmune disorders, Huntington's disease, Parkinson's disease, migraine, depression, peripheral neuropathy, pain, gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders, myasthenia gravis, polymyositis, myositis, bursitis, burns, diabetes, tumor invasion, tumor growth, tumor metastasis, corneal scarring, scleritis, immunodeficiency diseases, sepsis, premature labor, hyporothrombinemia, hemophilia, thyroiditis, sarcoidosis, Behcet's syndrome, hypersensitivity, kidney disease, rickettsial infections, protozoan diseases, reproductive disorders or septic shock.

The invention is also directed to methods of determining whether a test compound is an inhibitor of a prostaglandin transporter. These methods comprise contacting the test compound with the prostaglandin transporter, then determining whether the prostaglandin transporter has less transporter activity when contacted with the test compound than when not so contacted. The test compound in these methods is

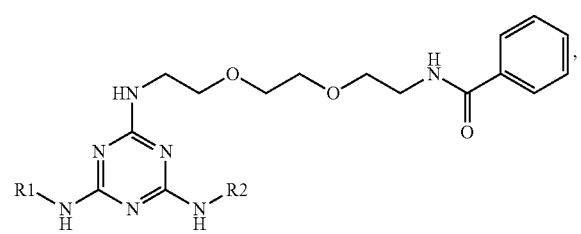

or a pharmaceutically acceptable salt, ester, or tautomer thereof, wherein R1 and R2 are independently a $C_1$-$C_{15}$ straight or branched alkyl, a substituted alkyl, a cycloalkyl, a carboxyalkyl, a substituted cycloalkyl, a $C_1$-$C_{15}$ straight or branched alkenyl, a substituted alkenyl, a cycloalkenyl, a substituted cycloalkenyl, a $C_1$-$C_{15}$ straight or branched alkinyl, a substituted alkinyl, a cycloalkinyl, a substituted cycloalkinyl, a $C_1$-$C_{10}$ straight or branched ether, a substituted ether, a cycloether, an ester, an amide, an acetyl, an aminal, an anhydride, an aryl, a substituted aryl, a heteroaryl, a substituted heteroaryl, a carboxyaryl, a heterocyclic group, a substituted heterocyclic group, a fused cycloalkyl, a substituted fused cycloalkyl, a fused heterocyclic group, a substituted fused heterocyclic group, a fused aryl, a substituted fused aryl, a fused heteroaryl, a substituted fused heteroaryl ring, or any combination thereof, optionally further comprising a hydroxy, an alkoxy, an aryloxy, an oxo, an ester, an ether, an amine, an azo, an azido, a nitro, an imine, an isothionate, a carbonyl, a peroxide, a halogen, a formyl, an acyl, a carboxy, an amido, a carbamoyl, a guanidino, a ureido, a amidino, a thiol, a mercapto, a sulfinyl, a sulfonyl and/or a sulfonamide.

These methods could employ any known procedures for determining prostaglandin transporter activity, e.g., those used in the Examples.

In these methods, R1 is preferably

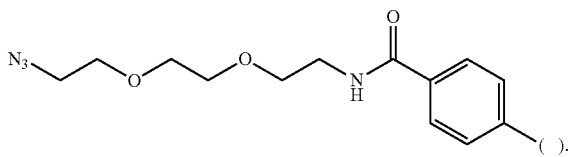

The invention is further directed to compounds that inhibit prostaglandin transporter activity. These compounds are With these, or any other set of PGT inhibitors identified herein (unless specifically excluded), it is understood that each of the above compounds individually could have different effects on PGT and prostaglandin metabolism or signaling, or side effects in particular species or individuals within any species. The skilled artisan could select the most preferred of any of the inhibitors for any particular application without undue experimentation.

The invention is additionally directed to pharmaceutical compositions comprising any of the above compounds in a pharmaceutically acceptable excipient.

By "pharmaceutically acceptable" it is meant a material that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, water, emulsions such as oil/water emulsions, microemulsions, and the like.

The above-described compounds can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, lingual, sublingual, buccal and intrabuccal administration can be made without undue experimentation by means well known

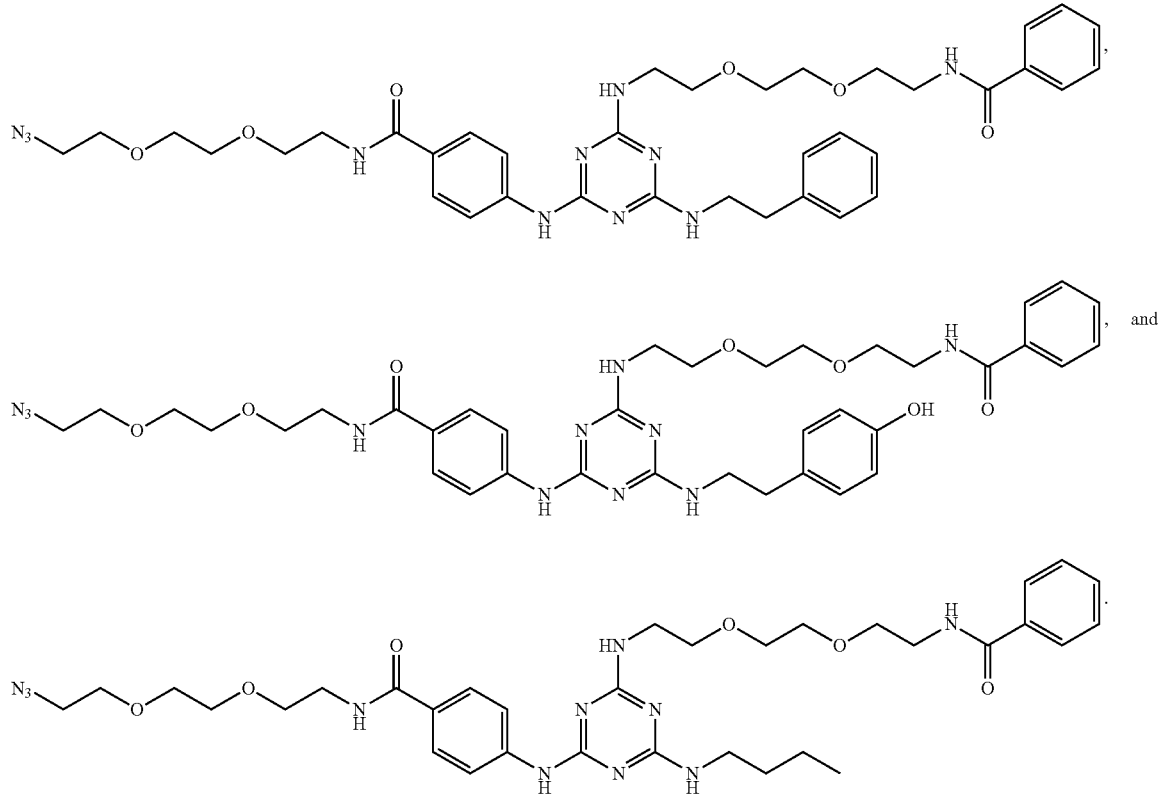

in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the compound, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the compound. As used herein, nasally administering or nasal administration includes administering the compound to the mucous membranes of the nasal passage or nasal cavity of the patient. As used herein, pharmaceutical compositions for nasal administration of the compound include therapeutically effective amounts of the compound prepared by well-known methods to be administered, for example, as a nasal spray, nasal drop, suspension, gel, ointment, cream or powder. Administration of the compound may also take place using a nasal tampon or nasal sponge.

Where the compound is administered peripherally such that it must cross the blood-brain barrier, the compound is preferably formulated in a pharmaceutical composition that enhances the ability of the compound to cross the blood-brain barrier of the mammal. Such formulations are known in the art and include lipophilic compounds to promote absorption. Uptake of non-lipophilic compounds can be enhanced by combination with a lipophilic substance. Lipophilic substances that can enhance delivery of the compound across the nasal mucus include but are not limited to fatty acids (e.g., palmitic acid), gangliosides (e.g., GM-I), phospholipids (e.g., phosphatidylserine), and emulsifiers (e.g., polysorbate 80), bile salts such as sodium deoxycholate, and detergent-like substances including, for example, polysorbate 80 such as Tween™, octoxynol such as Triton™X-100, and sodium tauro-24,25-dihydrofusidate (STDHF), See Lee et al., Biopharm., April 1988 issue: 3037.

In particular embodiments of the invention, the compound is combined with micelles comprised of lipophilic substances. Such micelles can modify the permeability of the nasal membrane to enhance absorption of the compound. Suitable lipophilic micelles include without limitation gangliosides (e.g., GM-I ganglioside), and phospholipids (e.g., phosphatidylserine). Bile salts and their derivatives and detergent-like substances can also be included in the micelle formulation. The compound can be combined with one or several types of micelles, and can further be contained within the micelles or associated with their surface.

Alternatively, the compound can be combined with liposomes (lipid vesicles) to enhance absorption. The compound can be contained or dissolved within the liposome and/or associated with its surface. Suitable liposomes include phospholipids (e.g., phosphatidylserine) and/or gangliosides (e.g., GM-1). For methods to make phospholipid vesicles, see for example, U.S. Pat. No. 4,921,706 to Roberts et al., and U.S. Pat. No. 4,895,452 to Yiournas et al. Bile salts and their derivatives and detergent-like substances can also be included in the liposome formulation.

The invention is further directed to methods of inhibiting prostaglandin transporter (PGT) activity in a mammal. The methods comprise administering a compound to the mammal effective to inhibit PGT activity. In these methods, the compound is

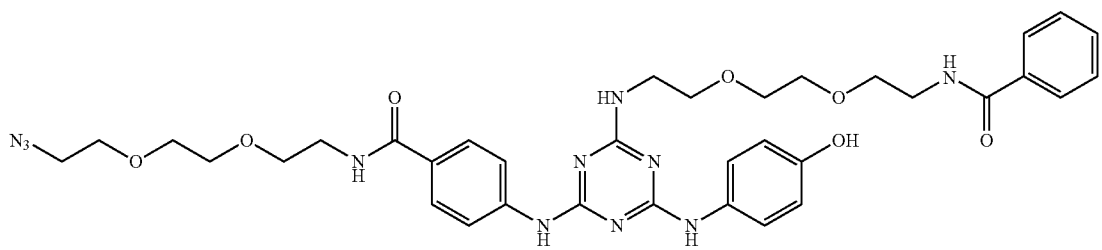

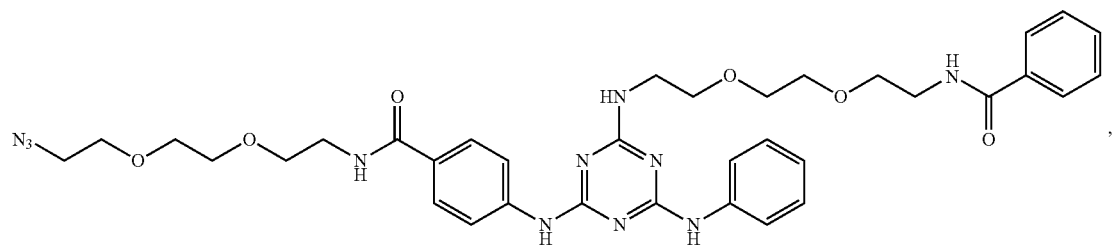,
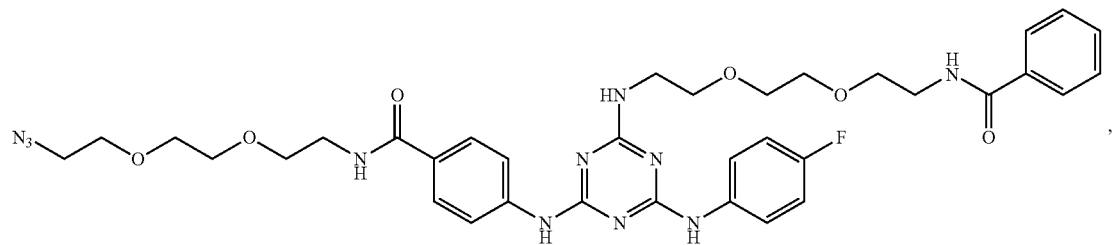,
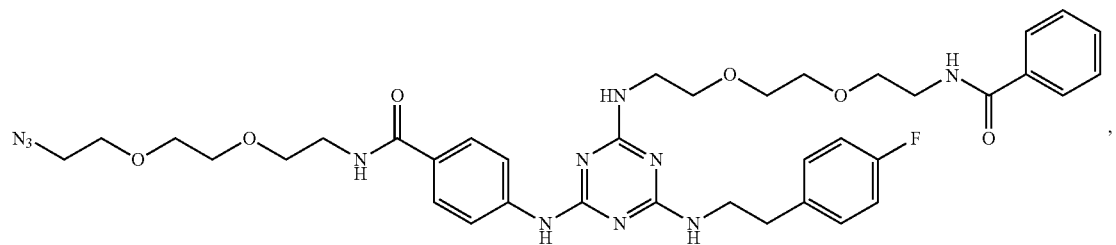,
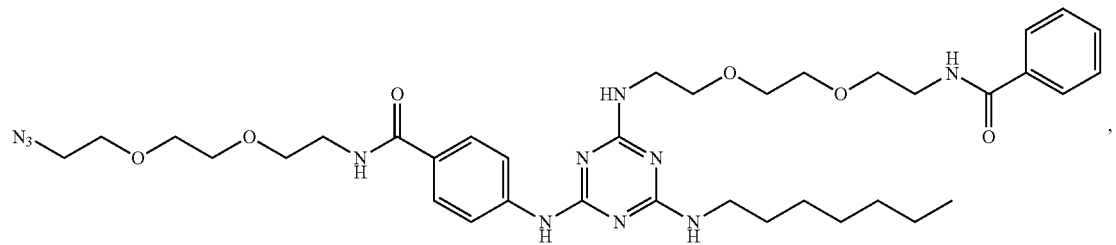,
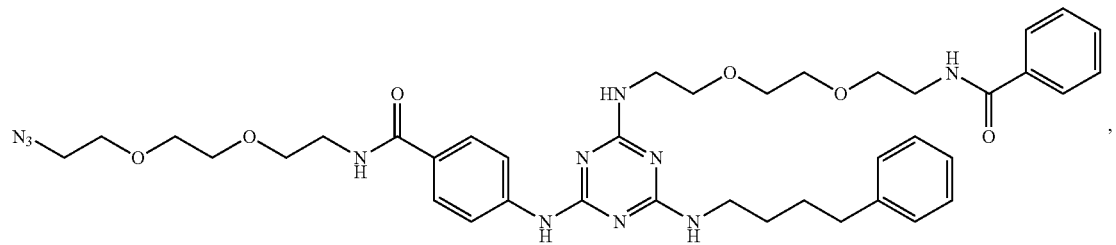,
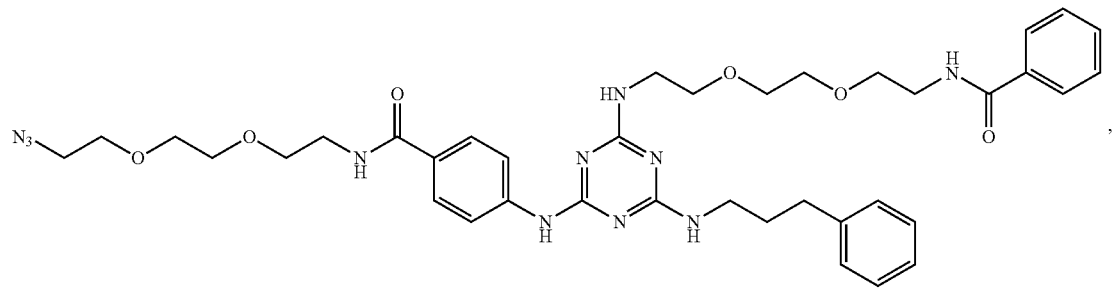,

-continued
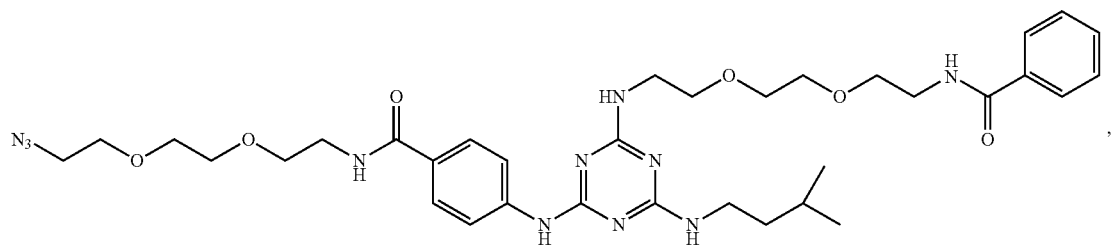
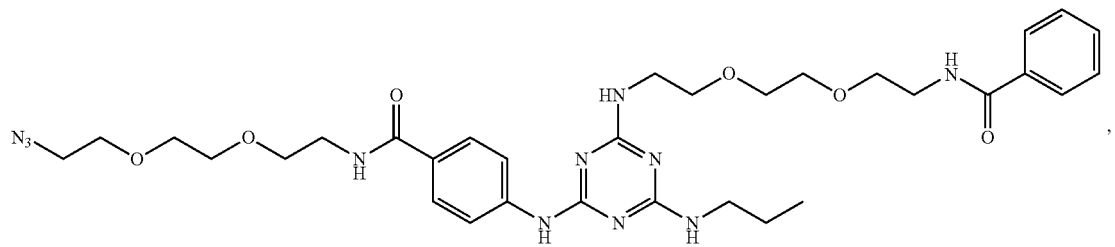
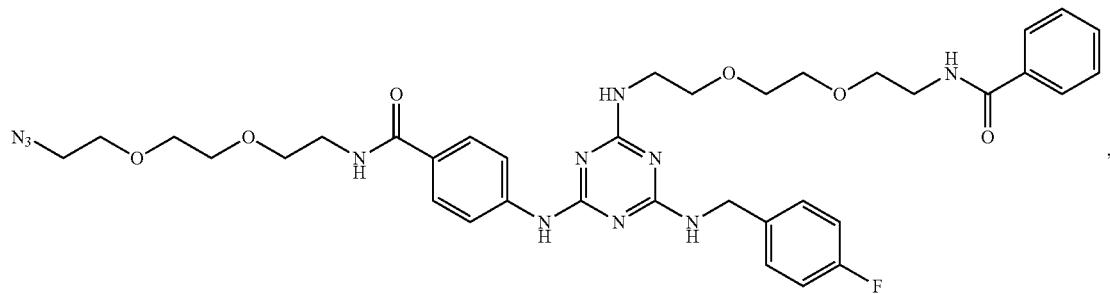
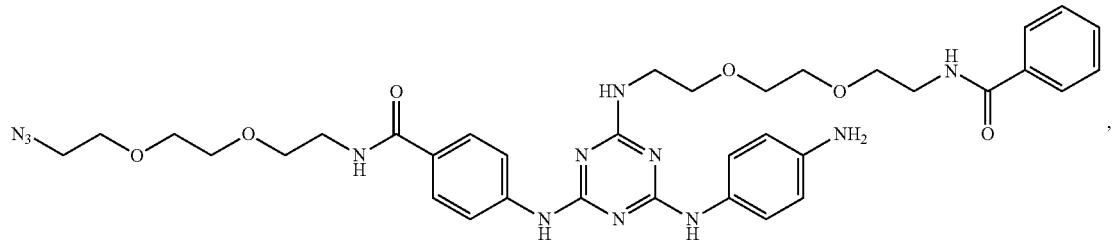
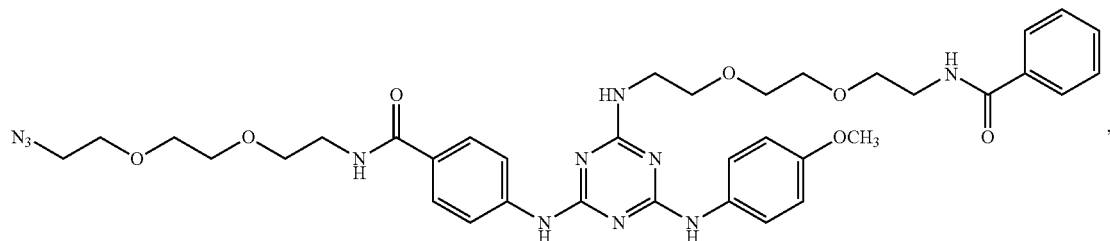
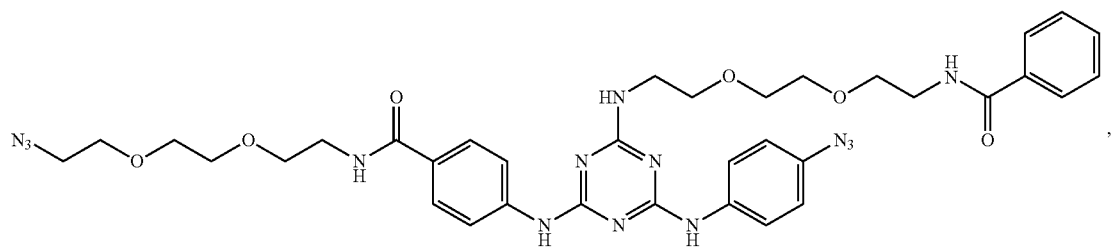

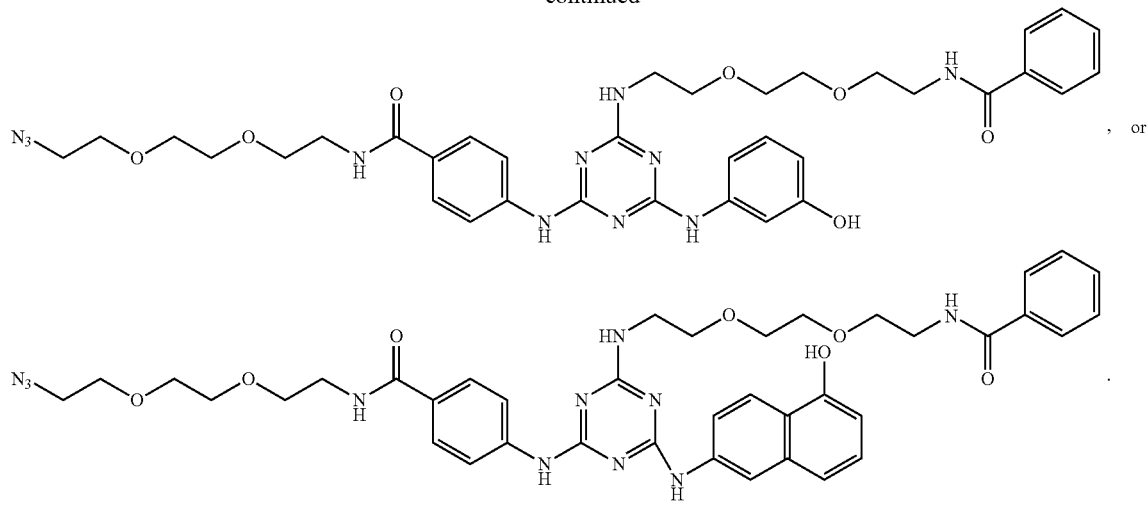

, or

Preferably, the mammal is a human suffering from a disease or disorder at least partially mediated by a cyclooxygenase-2. More preferably, the disease or disorder involves pain and/or inflammation. Non-limiting examples of diseases or disorders at least partially mediated by a cyclooxygenase-2 are arthritis, fever, common cold, hypertension, glaucoma, slow wound healing, slow initiation of labor, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer, tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis, aortic aneurysm, periarteritis nodosa, congestive heart failure, myocardial infarction, stroke, cerebral ischemia, head trauma, spinal cord injury, neuralgia, neuro-degenerative disorders, autoimmune disorders, Huntington's disease, Parkinson's disease, migraine, depression, peripheral neuropathy, pain, gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders, myasthenia gravis, polymyositis, myositis, bursitis, burns, diabetes, tumor invasion, tumor growth, tumor metastasis, corneal scarring, scleritis, immunodeficiency diseases, sepsis, premature labor, hyporothrombinemia, hemophilia, thyroiditis, sarcoidosis, Behcet's syndrome, hypersensitivity, kidney disease, rickettsial infections, protozoan diseases, reproductive disorders or septic shock.

Additionally, the invention is directed to methods of determining whether a test compound is an inhibitor of a prostaglandin transporter. The methods comprise contacting the test compound with the prostaglandin transporter, then determining whether the prostaglandin transporter has less transporter activity when contacted with the test compound than when no so contacted. In these methods, the test compound is

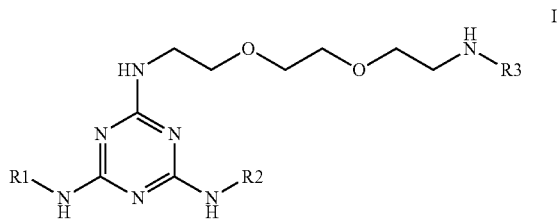

or a pharmaceutically acceptable salt, ester, or tautomer thereof, wherein R1, R2 and R3 are independently a $C_1$-$C_{15}$ straight or branched alkyl, a substituted alkyl, a cycloalkyl, a carboxyalkyl, a substituted cycloalkyl, a $C_1$-$C_{15}$ straight or branched alkenyl, a substituted alkenyl, a cycloalkenyl, a substituted cycloalkenyl, a $C_1$-$C_{15}$ straight or branched alkinyl, a substituted alkinyl, a cycloalkinyl, a substituted cycloalkinyl, a $C_1$-$C_{10}$ straight or branched ether, a substituted ether, a cycloether, an ester, an amide, an acetyl, an aminal, an anhydride, an aryl, a substituted aryl, a heteroaryl, a substituted heteroaryl, a carboxyaryl, a heterocyclic group, a substituted heterocyclic group, a fused cycloalkyl, a substituted fused cycloalkyl, a fused heterocyclic group, a substituted fused heterocyclic group, a fused aryl, a substituted fused aryl, a fused heteroaryl, a substituted fused heteroaryl ring, or any combination thereof, optionally further comprising a hydroxy, an alkoxy, an aryloxy, an oxo, an ester, an ether, an amine, an azo, an azido, a nitro, an imine, an isothionate, a carbonyl, a peroxide, a halogen, a formyl, an acyl, a carboxy, an amido, a carbamoyl, a guanidino, a ureido, a amidino, a thiol, a mercapto, a sulfinyl, a sulfonyl and/or a sulfonamide, and wherein R3 is not

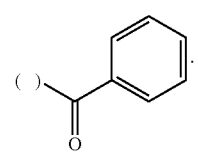

Preferably in these methods, R3 is
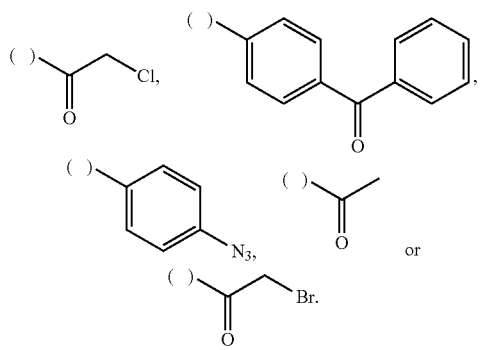
Preferred R1 moieties are
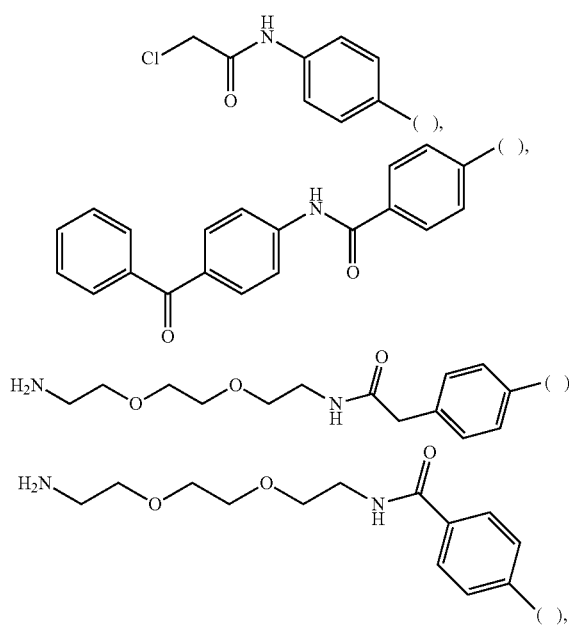
Additionally, preferred R2 moieties are
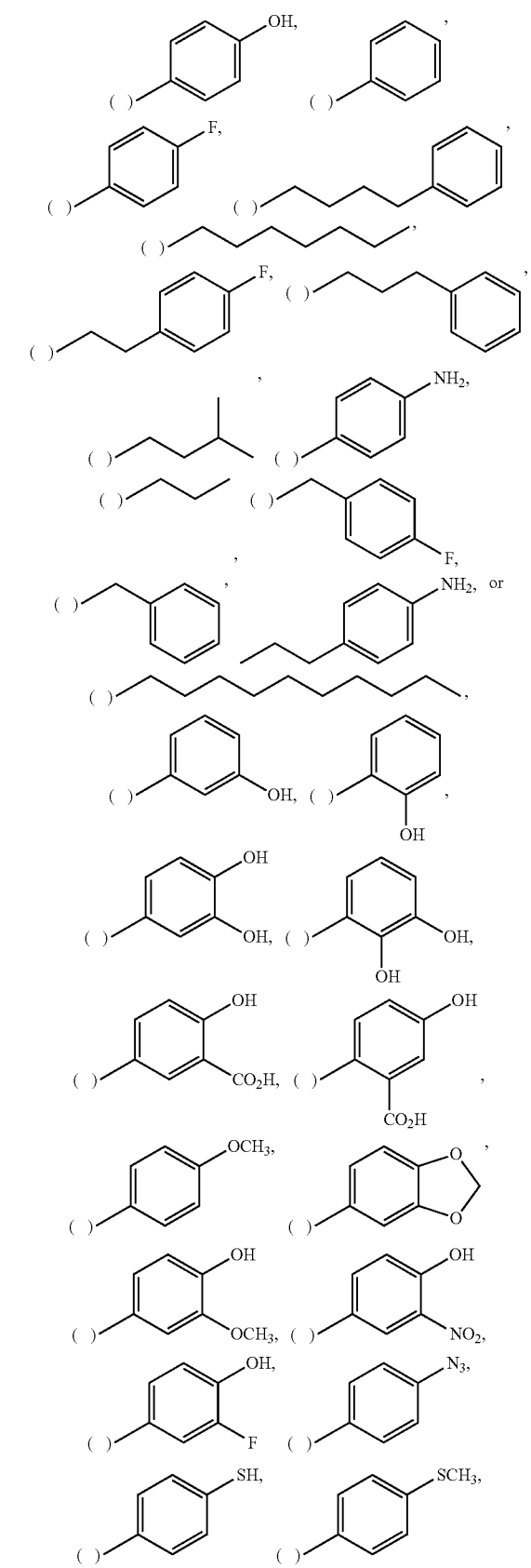

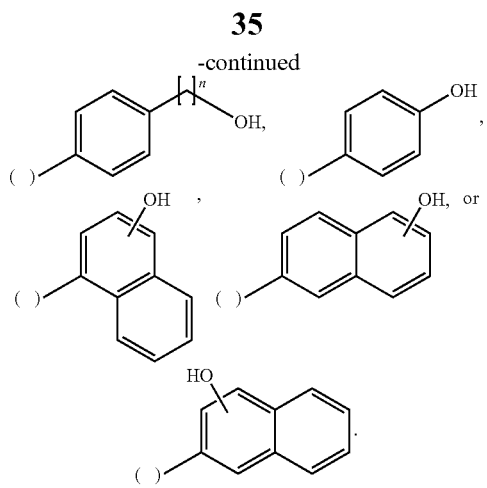

The invention is also directed to other methods of determining whether a test compound is an inhibitor of a prostaglandin transporter. These methods comprise contacting the test compound with the prostaglandin transporter, then determining whether the prostaglandin transporter has less transporter activity when contacted with the test compound than when not so contacted. Here, the test compound is

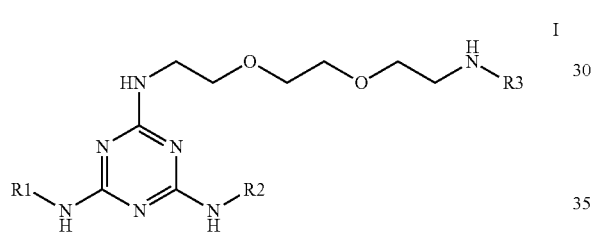

or a pharmaceutically acceptable salt, ester, or tautomer thereof, wherein R1 and R3 are independently a $C_1$-$C_{15}$ straight or branched alkyl, a substituted alkyl, a cycloalkyl, a carboxyalkyl, a substituted cycloalkyl, a $C_1$-$C_{15}$ straight or branched alkenyl, a substituted alkenyl, a cycloalkenyl, a substituted cycloalkenyl, a $C_1$-$C_{15}$ straight or branched alkinyl, a substituted alkinyl, a cycloalkinyl, a substituted cycloalkinyl, a $C_1$-$C_{10}$ straight or branched ether, a substituted ether, a cycloether, an ester, an amide, an acetyl, an aminal, an anhydride, an aryl, a substituted aryl, a heteroaryl, a substituted heteroaryl, a carboxyaryl, a heterocyclic group, a substituted heterocyclic group, a fused cycloalkyl, a substituted fused cycloalkyl, a fused heterocyclic group, a substituted fused heterocyclic group, a fused aryl, a substituted fused aryl, a fused heteroaryl, a substituted fused heteroaryl ring, or any combination thereof, optionally further comprising a hydroxy, an alkoxy, an aryloxy, an oxo, an ester, an ether, an amine, an azo, an azido, a nitro, an imine, an isothionate, a carbonyl, a peroxide, a halogen, a formyl, an acyl, a carboxy, an amido, a carbamoyl, a guanidino, a ureido, a amidino, a thiol, a mercapto, a sulfinyl, a sulfonyl and/or a sulfonamide, and wherein R2 is

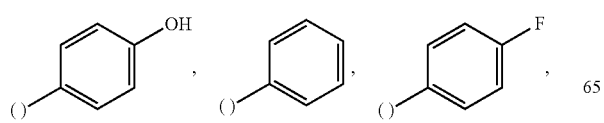

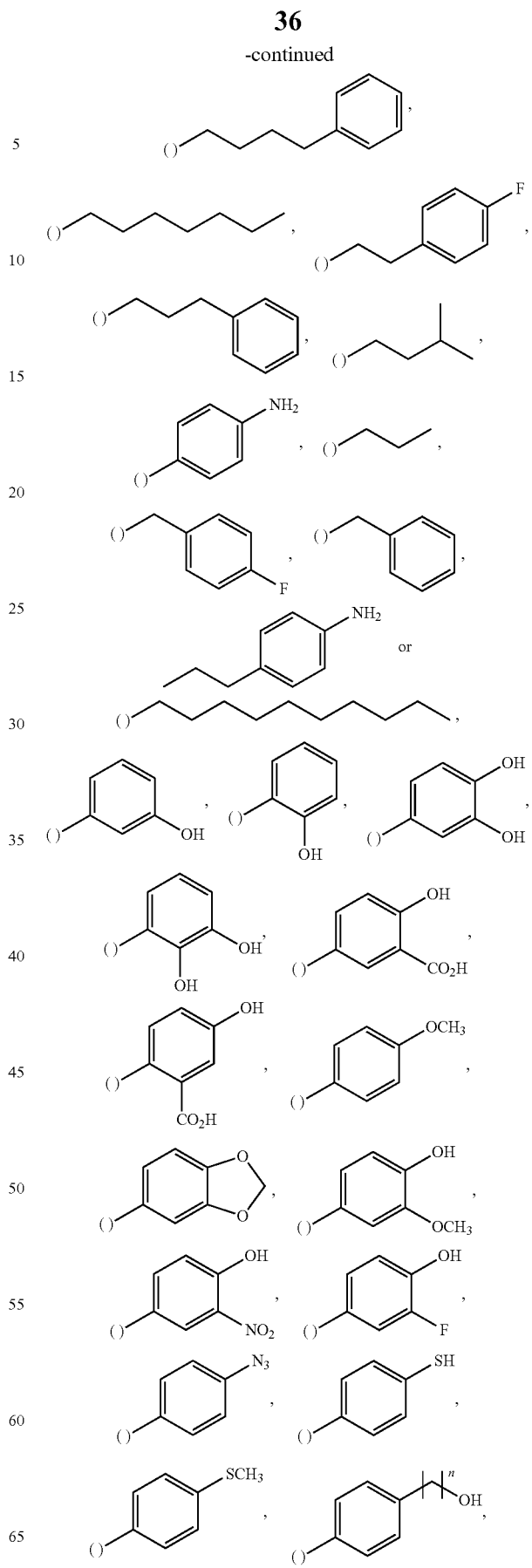

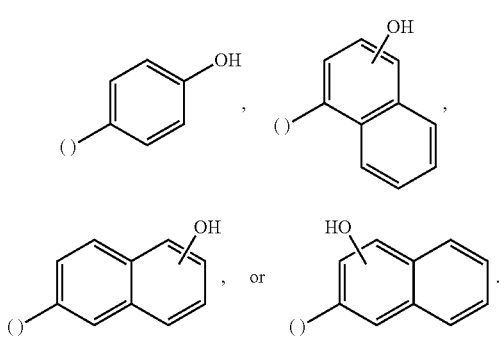

Examples of preferred R3 moieties are

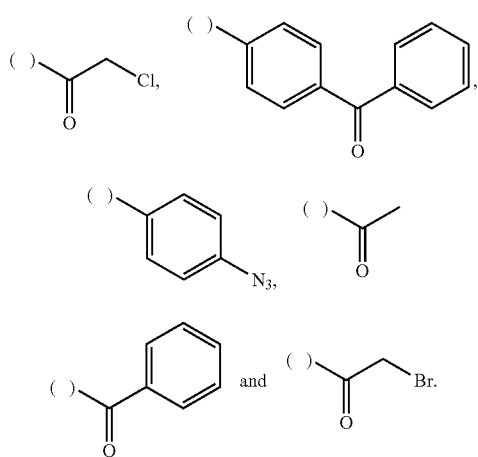

Examples of preferred R1 moieties are

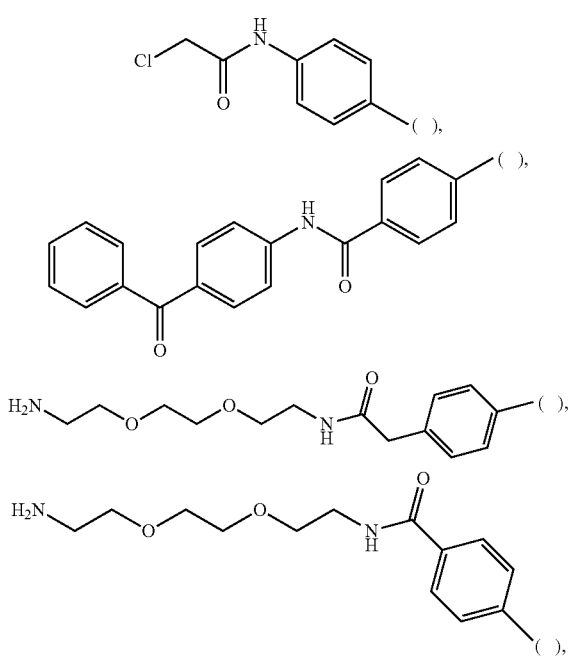

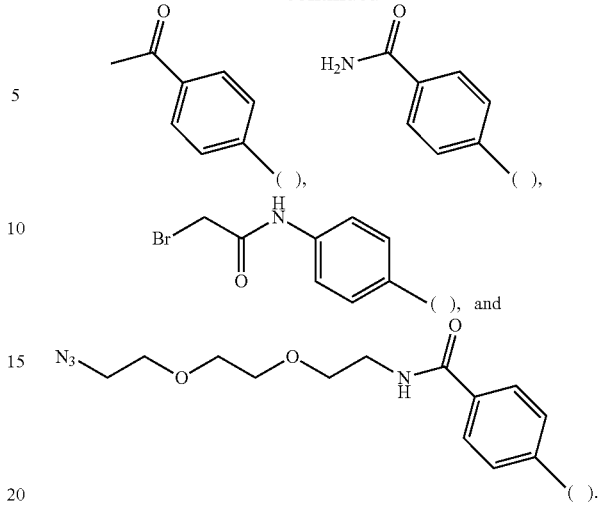

The inventors have also discovered that inhibition of PGT causes a reduction in cyclooxygenase-2 (COX-2) mRNA production, function, and protein (Example 2). Thus, the invention is additionally directed to methods of inhibiting COX-2 in a mammal. The methods comprise administering an inhibitor of prostaglandin transporter activity to the mammal.

The inhibitor of prostaglandin transporter activity in these methods can be any compound that inhibits expression or transporter activity of the PGT. Thus, for these methods, the inhibitor can prevent translation of the protein. Examples of such inhibitors are antisense nucleic acids, ribozymes or siRNA, where the antisense nucleic acid, the ribozyme or the siRNA is specific for the mRNA of the prostaglandin transporter. The skilled artisan could design and produce such inhibitors without undue experimentation.

The inhibitor in these methods can also be an antibody or aptamer that specifically inhibits the prostaglandin transporter. Production of these inhibitors is also within the skill of the art.

Preferably in these methods, the inhibitor is a compound having Formula 1:

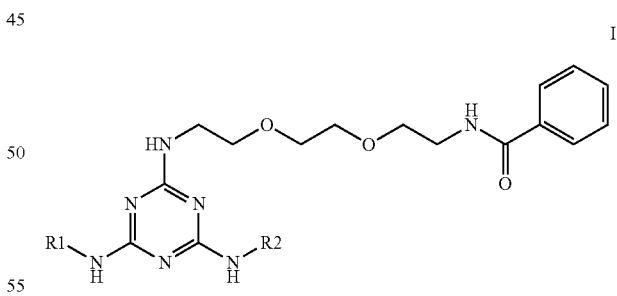

I or a pharmaceutically acceptable salt, ester, or tautomer thereof, wherein R1 and R2 are independently a $C_1$-$C_{15}$ straight or branched alkyl, a substituted alkyl, a cycloalkyl, a carboxyalkyl, a substituted cycloalkyl, a $C_1$-$C_{15}$ straight or branched alkenyl, a substituted alkenyl, a cycloalkenyl, a substituted cycloalkenyl, a $C_1$-$C_{15}$ straight or branched alkinyl, a substituted alkinyl, a cycloalkinyl, a substituted cycloalkinyl, a $C_1$-$C_{10}$ straight or branched ether, a substituted ether, a cycloether, an ester, an amide, an acetyl, an aminal, an anhydride, an aryl, a substituted aryl, a heteroaryl, a substituted heteroaryl, a carboxyaryl, a heterocyclic group, a substituted heterocyclic group, a fused cycloalkyl, a substituted fused cycloalkyl, a fused heterocyclic group, a substituted fused heterocyclic group, a fused aryl, a substituted fused aryl, a fused heteroaryl, a substituted fused heteroaryl ring, or any combination thereof, optionally further comprising a hydroxy, an alkoxy, an aryloxy, an oxo, an ester, an ether, an amine, an azo, an azido, a nitro, an imine, an isothionate, a carbonyl, a peroxide, a halogen, a formyl, an acyl, a carboxy, an amido, a carbamoyl, a guanidino, a ureido, a amidino, a thiol, a mercapto, a sulfinyl, a sulfonyl and/or a sulfonamide.

More preferably, R1 is

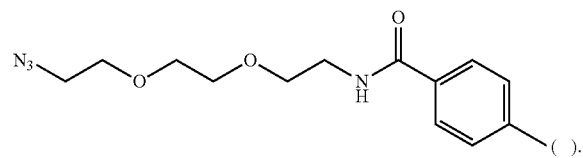

Preferably, R2 comprises a carboxyl or phenol group. More preferably, R2 is a $C_1$-$C_{10}$ straight or branched alkyl, a phenyl, a fused aryl, a fused heteroaryl, or any combination thereof, optionally substituted with a halogen, a carboxyl, an amino, a nitro, a $SCH_3$, a hydroxyl, a $C_1$-$C_3$ alkoxy, $C_1$-$C_3$ straight or branched alkyl, an azido, or a combination thereof. Even more preferably, R2 is a $C_1$-$C_3$ straight or branched alkyl, a phenyl, a fused aryl, or a combination of a $C_1$-$C_5$ straight or branched alkyl and a phenyl, optionally substituted with a halogen, one or more hydroxyls, a methoxy, a nitro, a carboxy, or a combination thereof. Still more preferably, R2 is

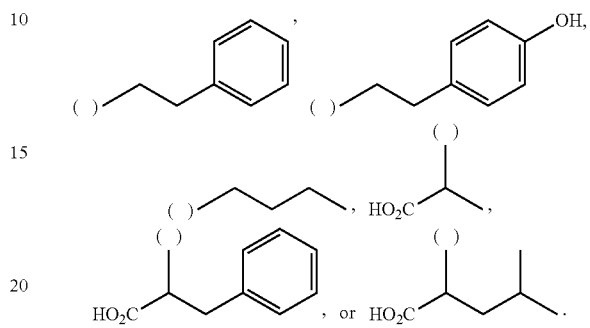

Most preferably, the compound in these methods is

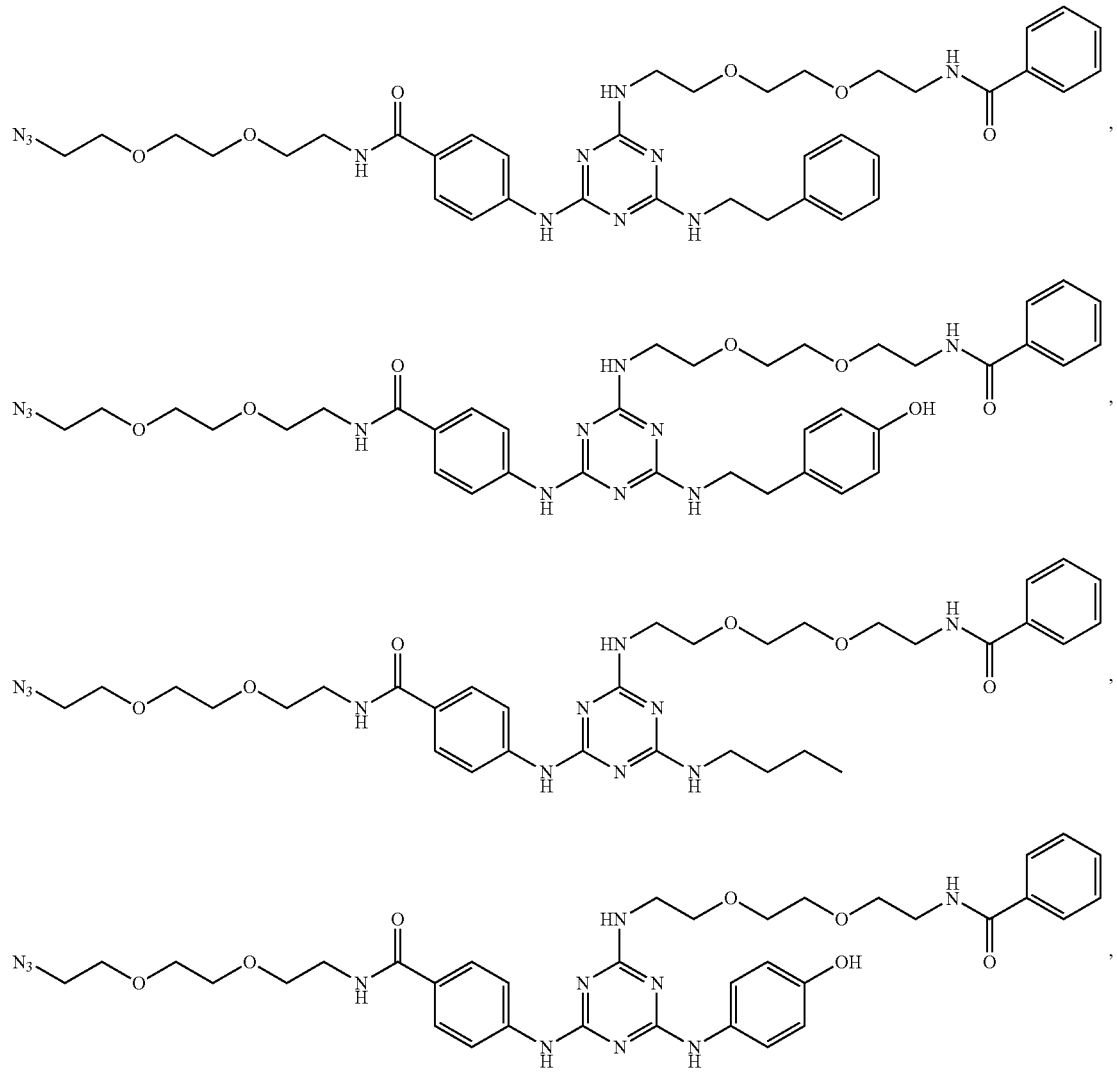

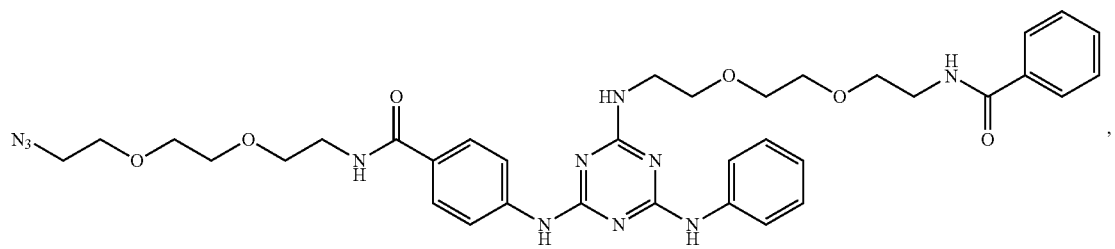
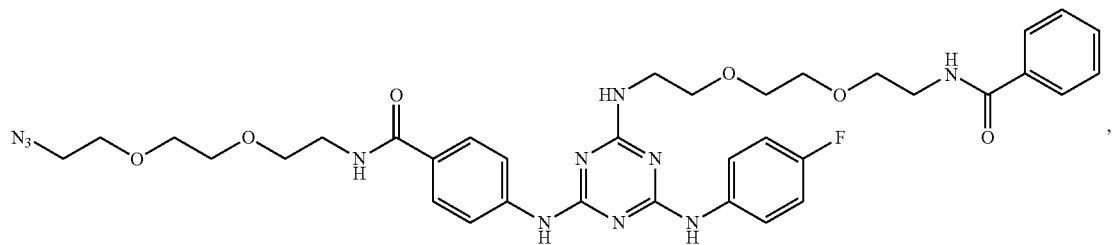
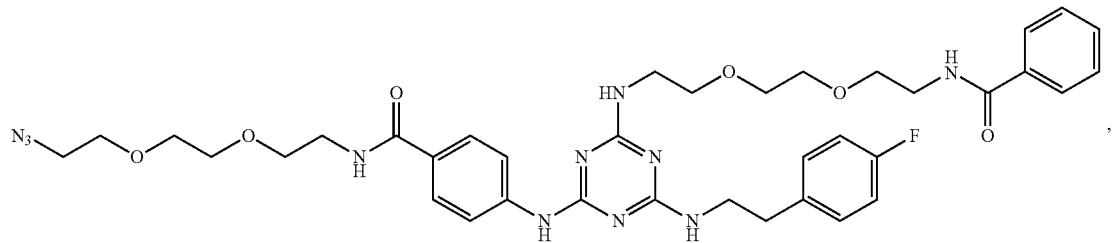
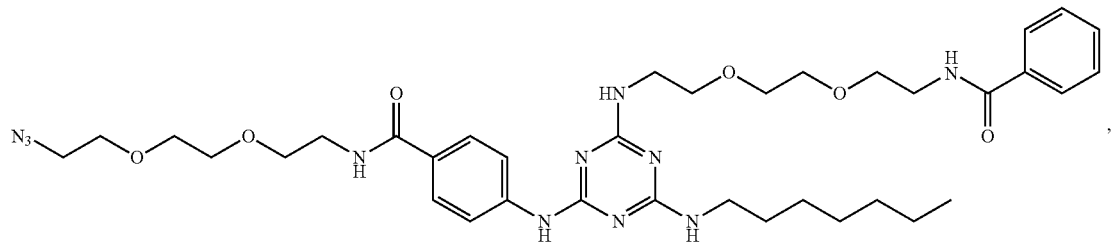
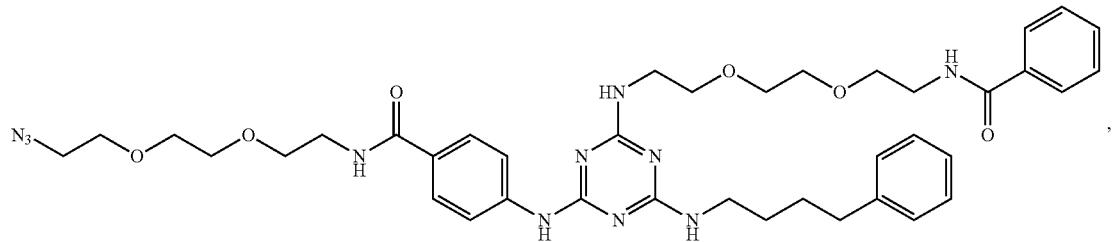
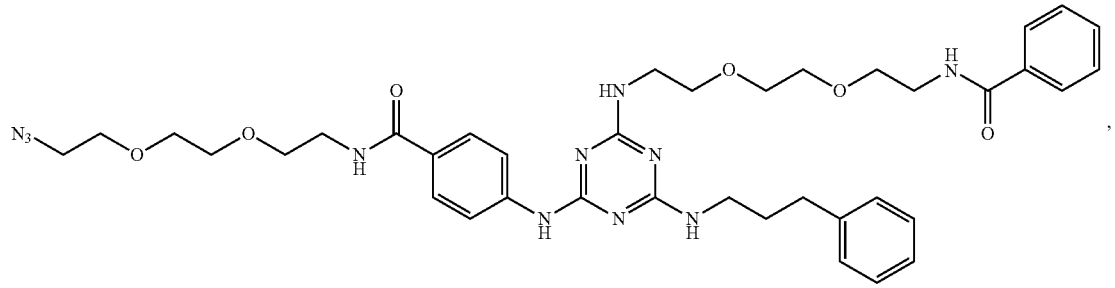

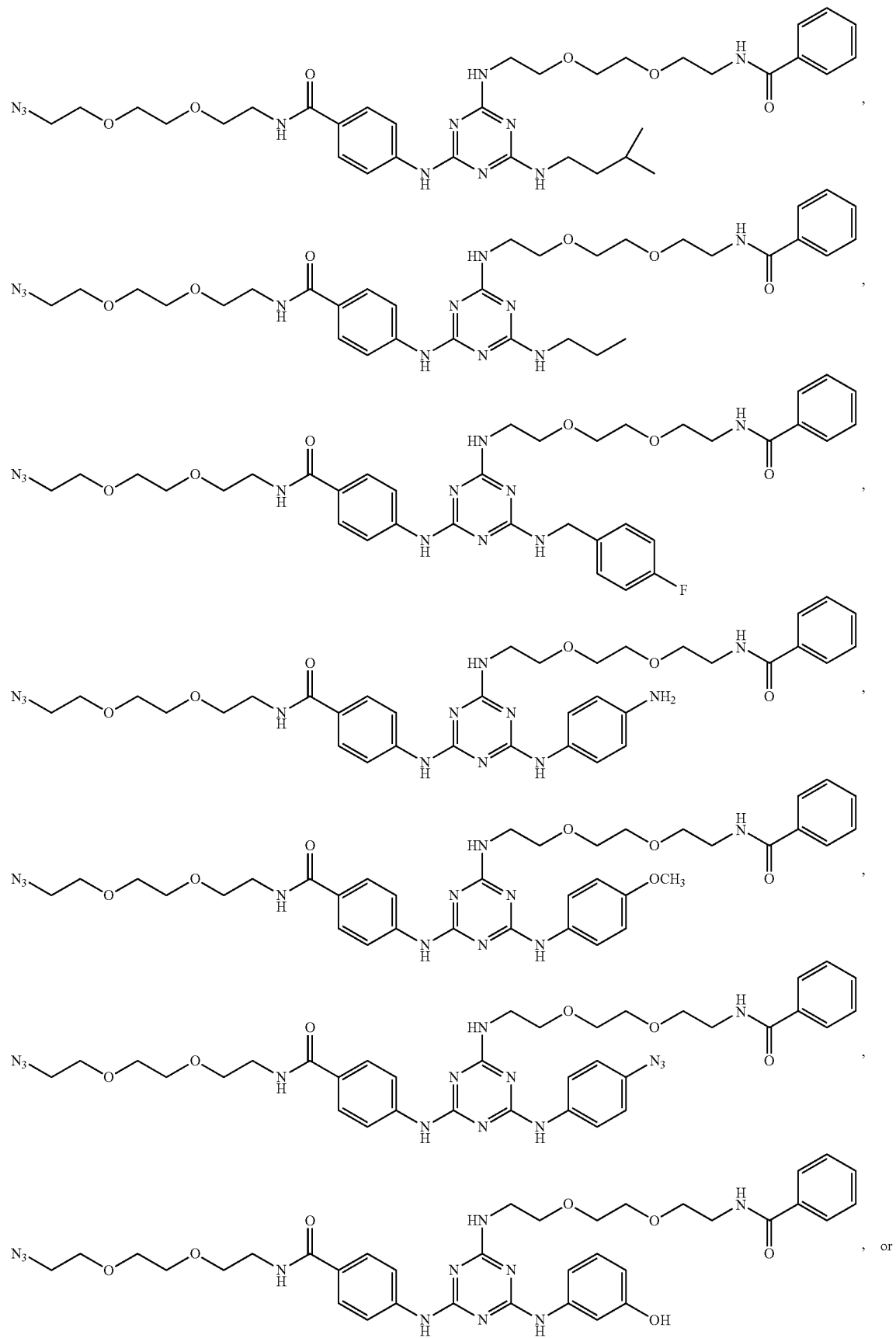

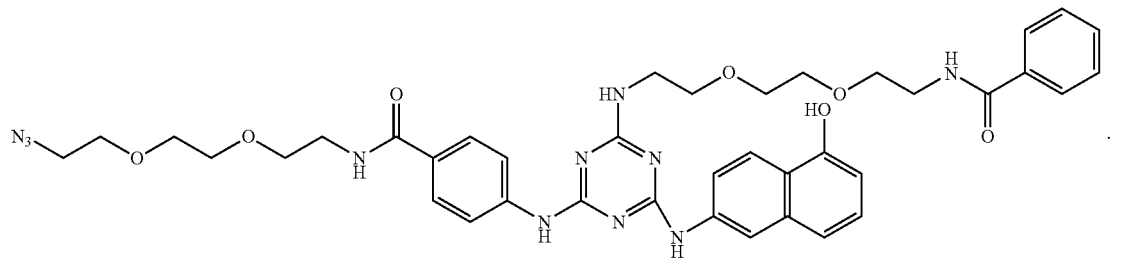

In preferred aspects of these methods, the mammal is a human suffering from a disease or disorder at least partially mediated by a cyclooxygenase-2. More preferably, the disease or disorder involves pain and/or inflammation. Non-limiting examples of diseases or disorders at least partially mediated by a cyclooxygenase-2 are arthritis, fever, common cold, hypertension, glaucoma, slow wound healing, slow initiation of labor, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer, tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis, aortic aneurysm, periarteritis nodosa, congestive heart failure, myocardial infarction, stroke, cerebral ischemia, head trauma, spinal cord injury, neuralgia, neuro-degenerative disorders, autoimmune disorders, Huntington's disease, Parkinson's disease, migraine, depression, peripheral neuropathy, pain, gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders, myasthenia gravis, polymyositis, myositis, bursitis, burns, diabetes, tumor invasion, tumor growth, tumor metastasis, corneal scarring, scleritis, immunodeficiency diseases, sepsis, premature labor, hyporothrombinemia, hemophilia, thyroiditis, sarcoidosis, Behcet's syndrome, hypersensitivity, kidney disease, rickettsial infections, protozoan diseases, reproductive disorders or septic shock.

The present invention is further directed to methods of treating pain or inflammation in a mammal. The methods comprise administering an inhibitor of prostaglandin transporter activity to the mammal. Since PGT inhibition also inhibits COX-2, and inhibition of COX-2 is a recognized treatment of pain or inflammation, PGT inhibitors are useful for treating pain or inflammation. As used herein, unless otherwise specified, "pain or inflammation" is equivalent to "pain or inflammation or both" and "pain and/or inflammation".

In these methods, the inhibitor of PGT activity can function by inhibiting production of PGT, e.g., through the use of antisense nucleic acids, ribozymes, or siRNA (Example 2) that are specific for the mRNA of the prostaglandin transporter. Methods of making and testing such compounds are within the skill of the art.

The inhibitor of PGT activity can also function by inhibiting the function of the PGT, preferably by binding to the PGT, making the substrate-interacting site inaccessible to the substrate. Examples of such inhibitors are antibodies or aptamers that specifically inhibit the prostaglandin transporter. Preferably, the inhibitor is a compound having Formula 1:

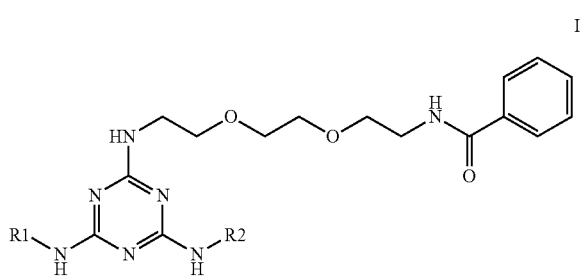

or a pharmaceutically acceptable salt, ester, or tautomer thereof, wherein R1 and R2 are independently a $C_1$-$C_{15}$ straight or branched alkyl, a substituted alkyl, a cycloalkyl, a carboxyalkyl, a substituted cycloalkyl, a $C_1$-$C_{15}$ straight or branched alkenyl, a substituted alkenyl, a cycloalkenyl, a substituted cycloalkenyl, a $C_1$-$C_{15}$ straight or branched alkinyl, a substituted alkinyl, a cycloalkinyl, a substituted cycloalkinyl, a $C_1$-$C_{10}$ straight or branched ether, a substituted ether, a cycloether, an ester, an amide, an acetyl, an aminal, an anhydride, an aryl, a substituted aryl, a heteroaryl, a substituted heteroaryl, a carboxyaryl, a heterocyclic group, a substituted heterocyclic group, a fused cycloalkyl, a substituted fused cycloalkyl, a fused heterocyclic group, a substituted fused heterocyclic group, a fused aryl, a substituted fused aryl, a fused heteroaryl, a substituted fused heteroaryl ring, or any combination thereof, optionally further comprising a hydroxy, an alkoxy, an aryloxy, an oxo, an ester, an ether, an amine, an azo, an azido, a nitro, an imine, an isothionate, a carbonyl, a peroxide, a halogen, a formyl, an acyl, a carboxy, an amido, a carbamoyl, a guanidino, a ureido, a amidino, a thiol, a mercapto, a sulfinyl, a sulfonyl and/or a sulfonamide.

Preferably in these methods, the R1 of Formula 1 is

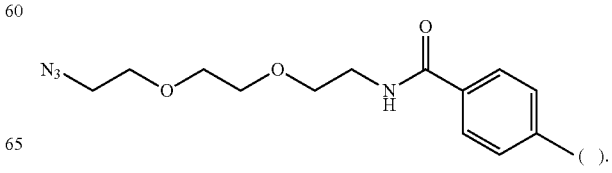

Most preferably, the compound is
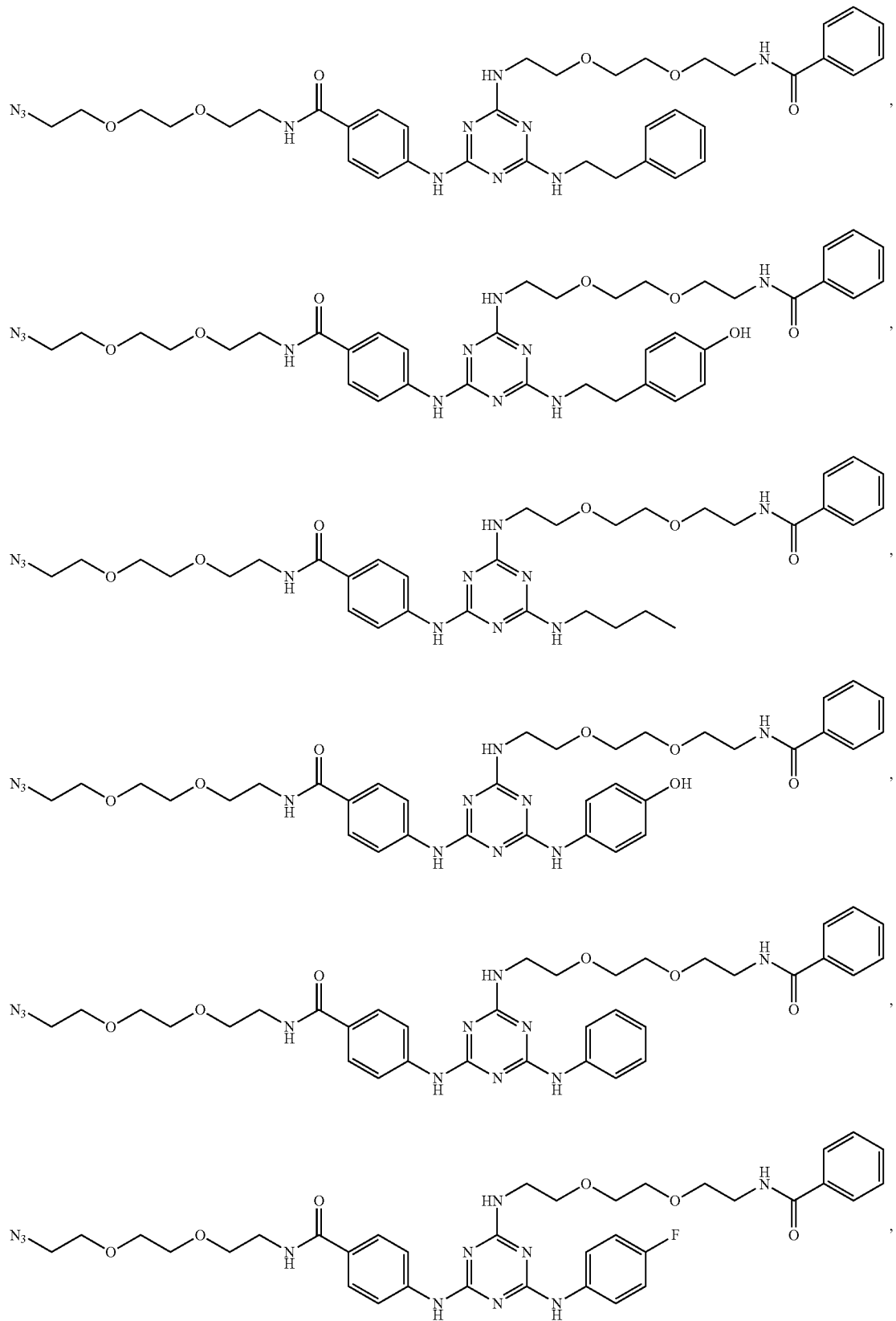

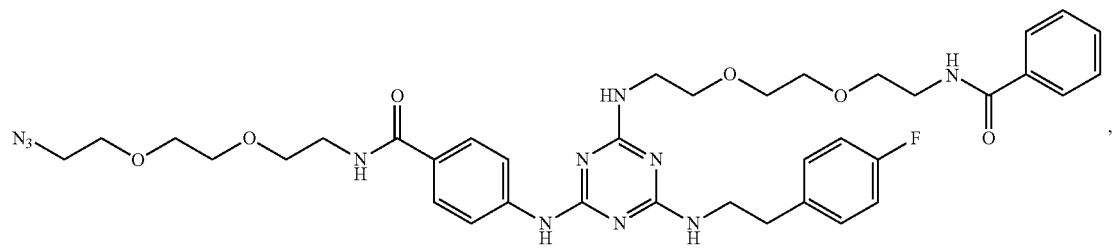
,
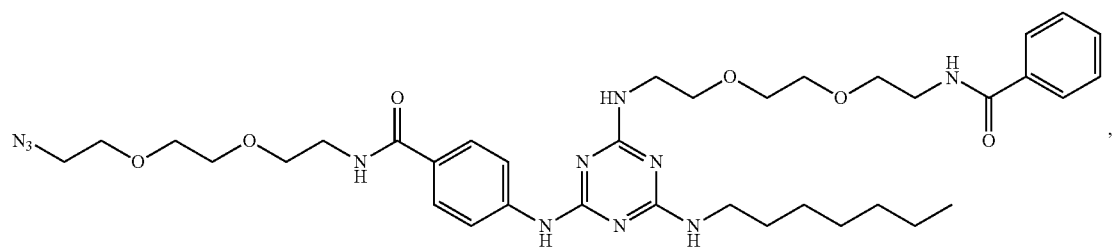
,
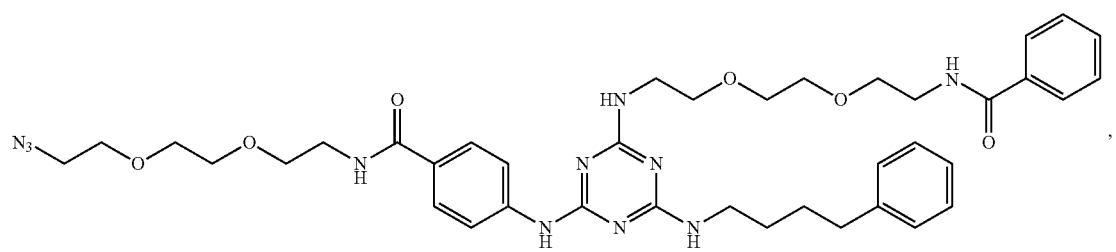
,
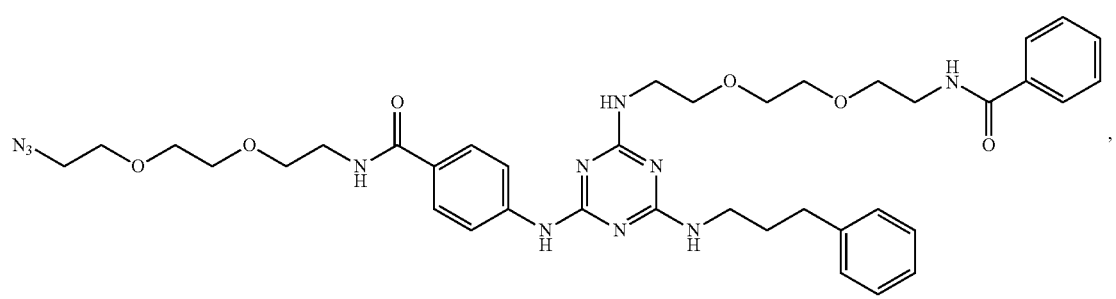
,
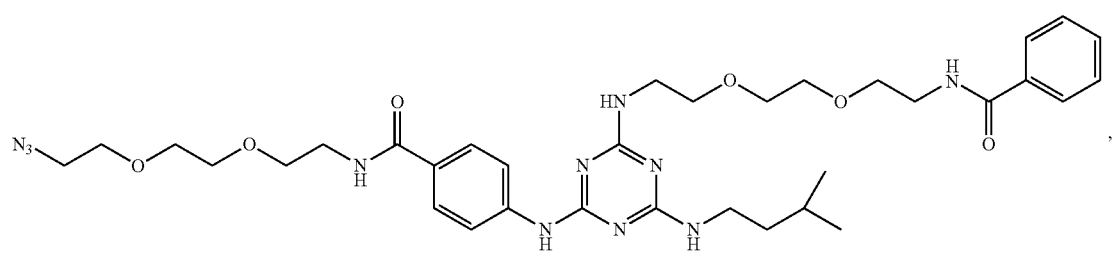
,
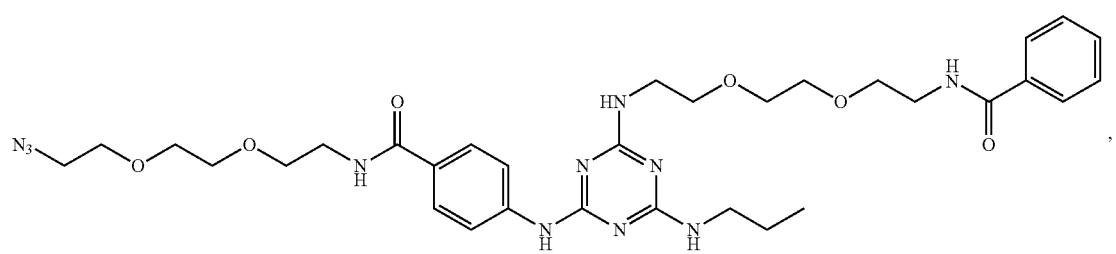
,

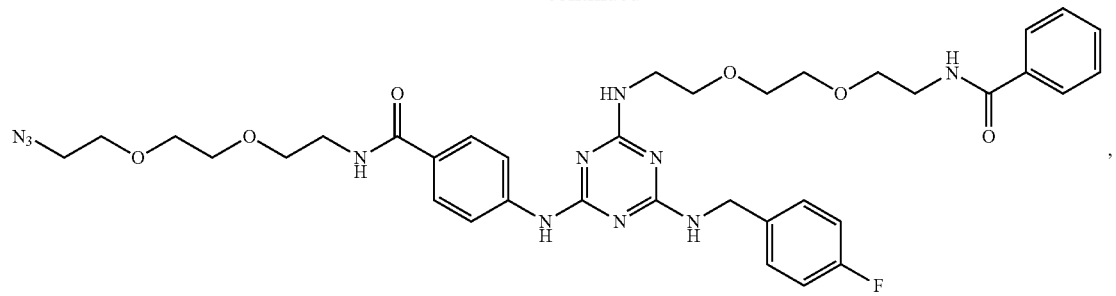
,
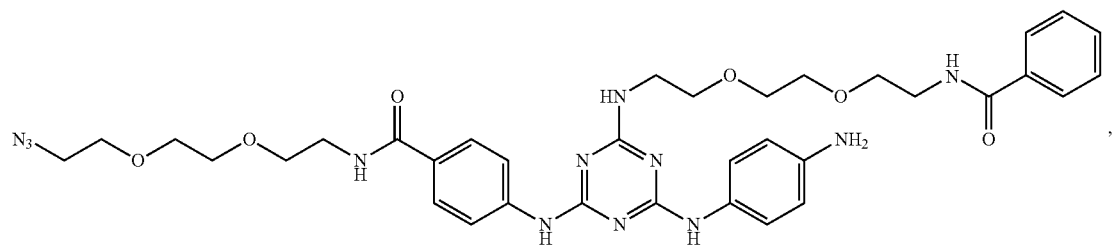
,
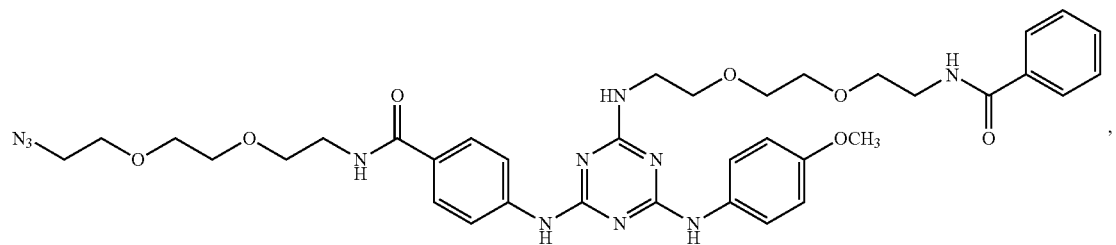
,
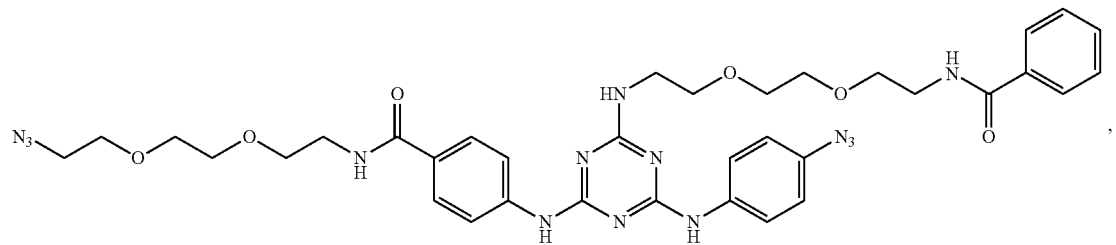
,
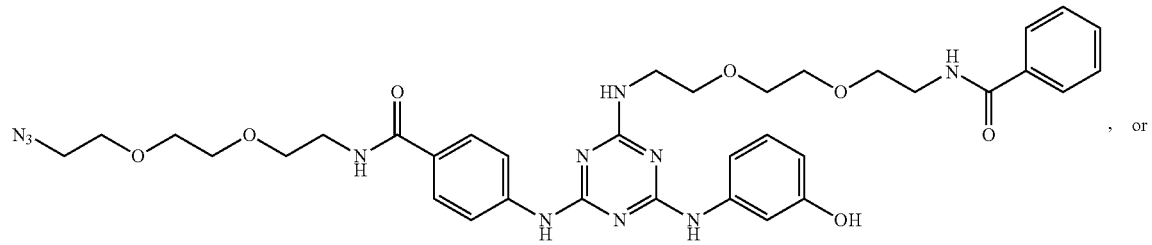
, or
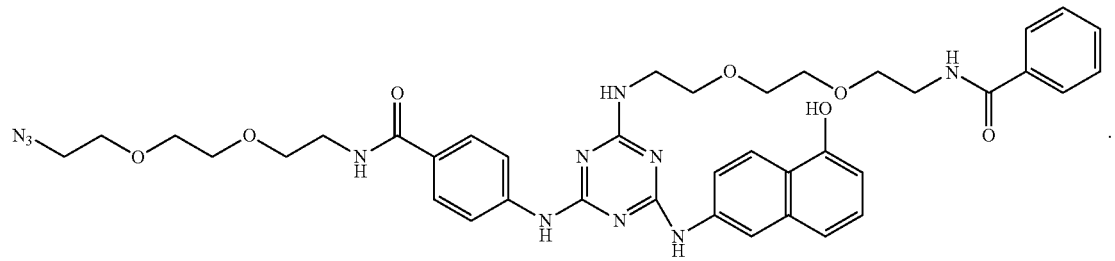
.

The invention is also directed to compounds that inhibit prostaglandin transporter activity, where the compound is
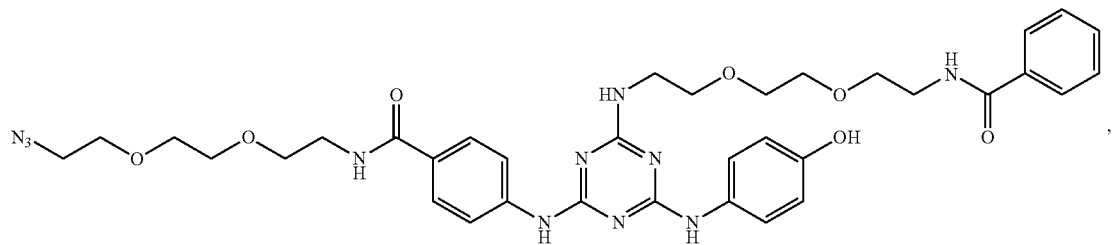
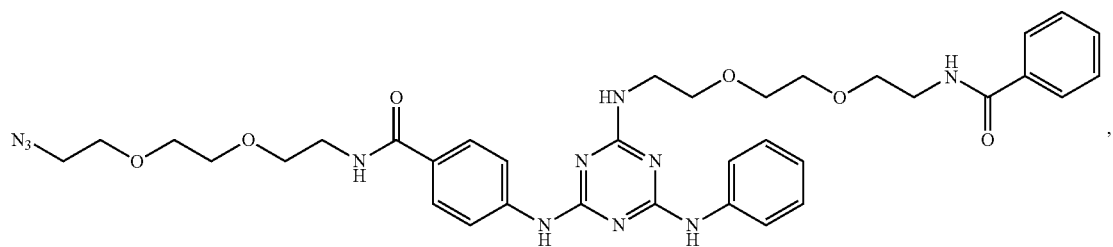
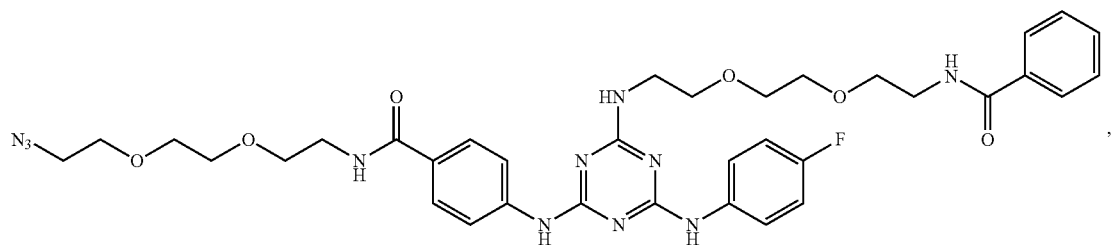
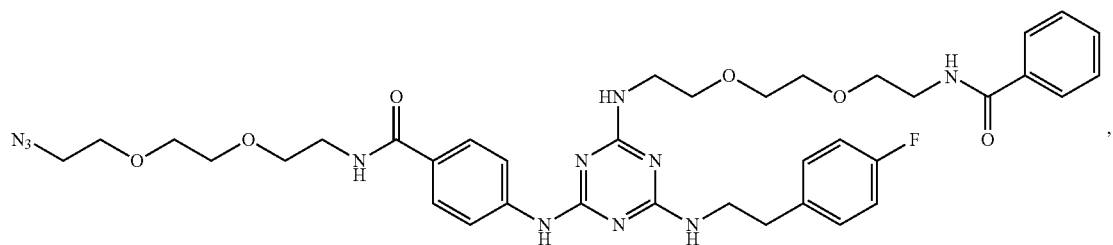
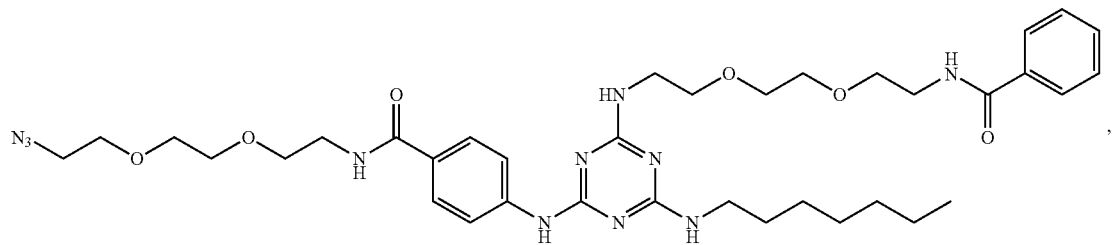
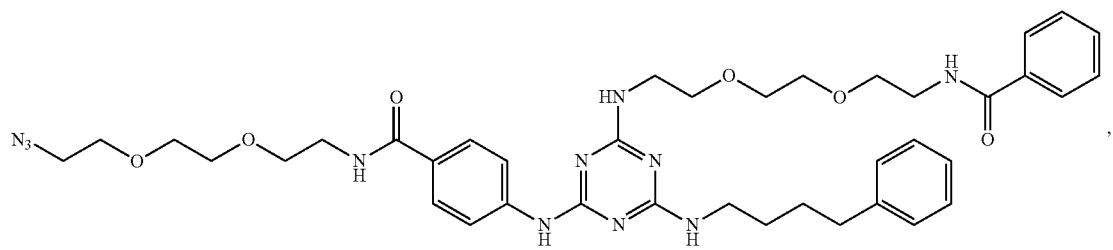

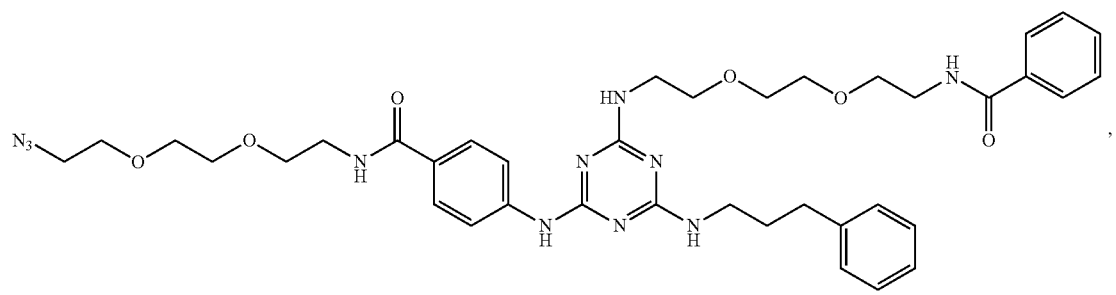,
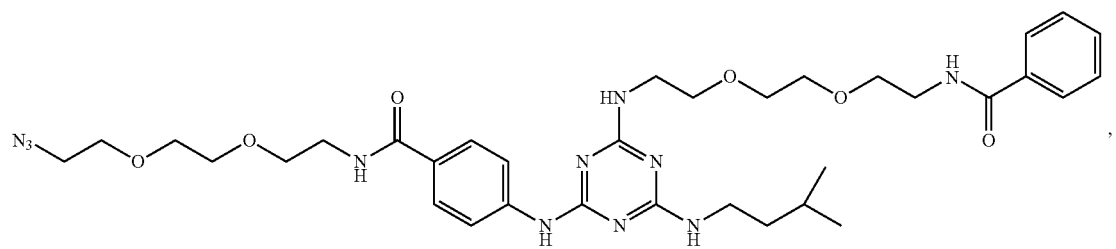,
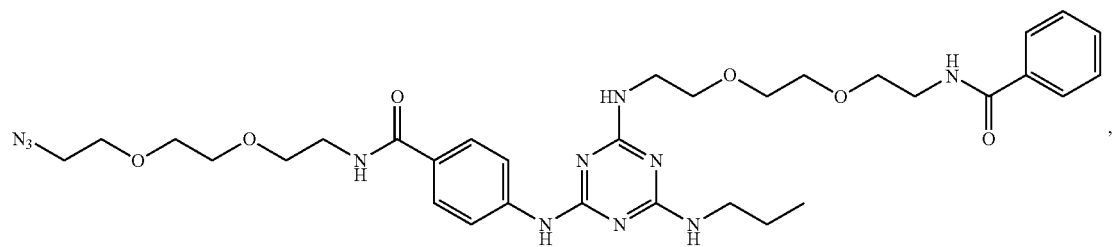,
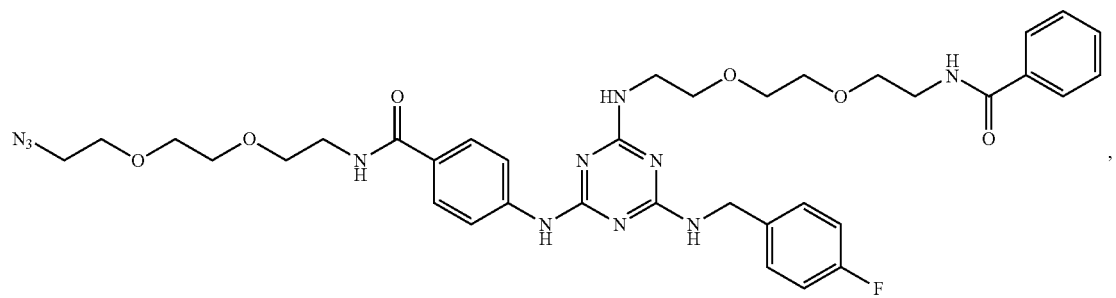,
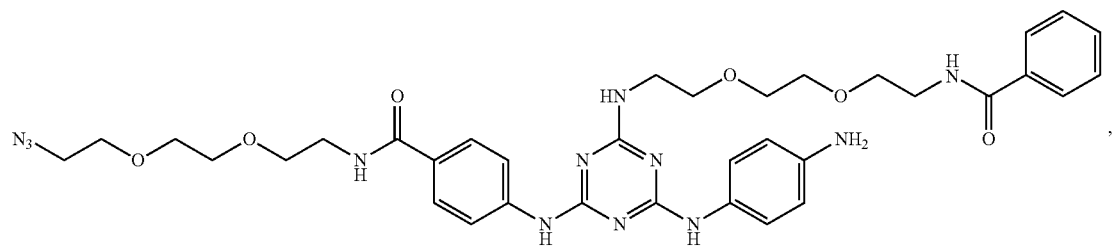,
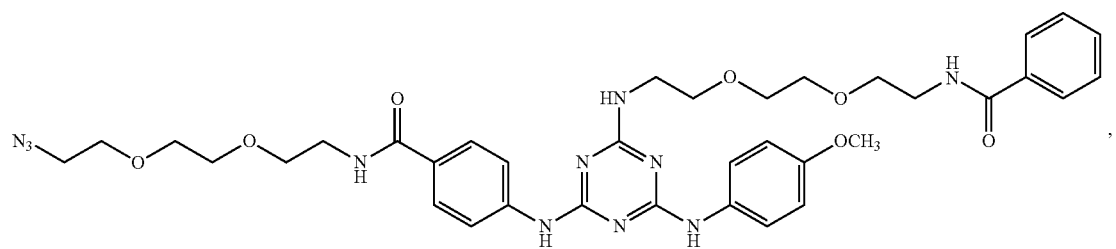,

-continued

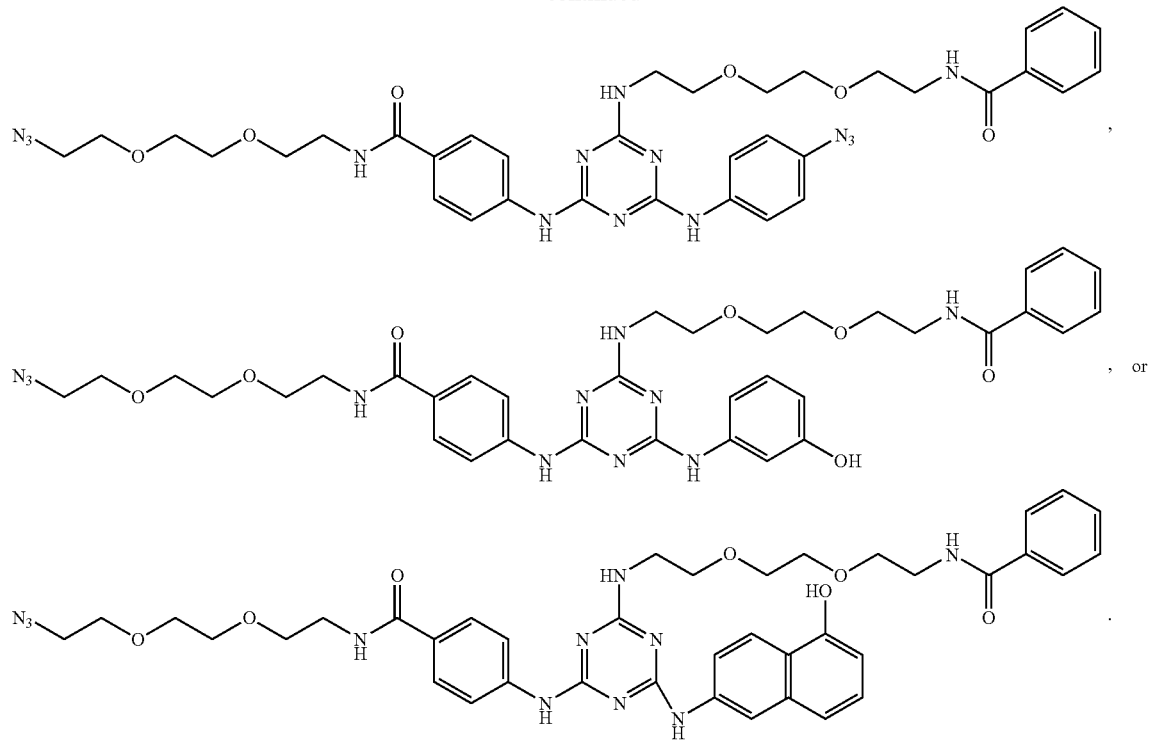

The invention is further directed to pharmaceutical compositions comprising any of the above-described compounds in a pharmaceutically acceptable excipient.

Additionally, the invention is directed to the use of a COX-2-inhibiting effective amount of Compound I, or a pharmaceutically acceptable salt, ester, or tautomer thereof, for the manufacture of a medicament for the treatment of a disorder or condition at least partially mediated by COX-2 in a mammal. Here, Compound I is

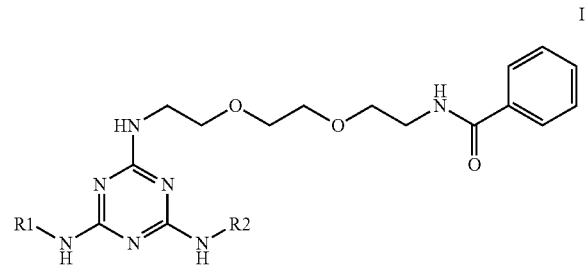

or a pharmaceutically acceptable salt, ester, or tautomer thereof, wherein R1 and R2 are independently a $C_1$-$C_{15}$ straight or branched alkyl, a substituted alkyl, a cycloalkyl, a carboxyalkyl, a substituted cycloalkyl, a $C_1$-$C_{15}$ straight or branched alkenyl, a substituted alkenyl, a cycloalkenyl, a substituted cycloalkenyl, a $C_1$-$C_{15}$ straight or branched alkinyl, a substituted alkinyl, a cycloalkinyl, a substituted cycloalkinyl, a $C_1$-$C_{10}$ straight or branched ether, a substituted ether, a cycloether, an ester, an amide, an acetyl, an aminal, an anhydride, an aryl, a substituted aryl, a heteroaryl, a substituted heteroaryl, a carboxyaryl, a heterocyclic group, a substituted heterocyclic group, a fused cycloalkyl, a substituted fused cycloalkyl, a fused heterocyclic group, a substituted fused heterocyclic group, a fused aryl, a substituted fused aryl, a fused heteroaryl, a substituted fused heteroaryl ring, or any combination thereof, optionally further comprising a hydroxy, an alkoxy, an aryloxy, an oxo, an ester, an ether, an amine, an azo, an azido, a nitro, an imine, an isothionate, a carbonyl, a peroxide, a halogen, a formyl, an acyl, a carboxy, an amido, a carbamoyl, a guanidino, a ureido, a amidino, a thiol, a mercapto, a sulfinyl, a sulfonyl and/or a sulfonamide.

Preferably, R1 is

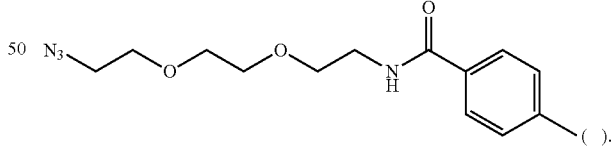

Most preferably, the compound of Formula 1 is

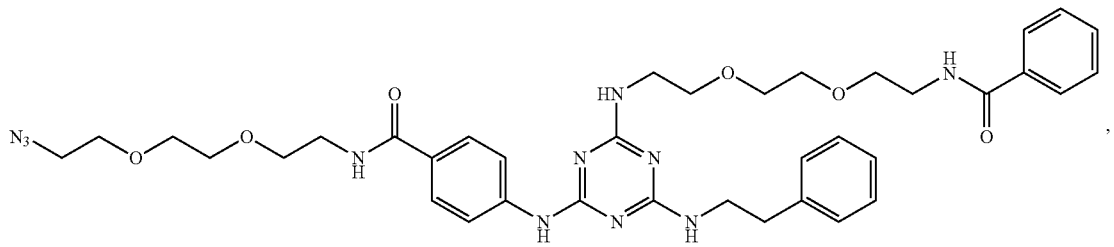

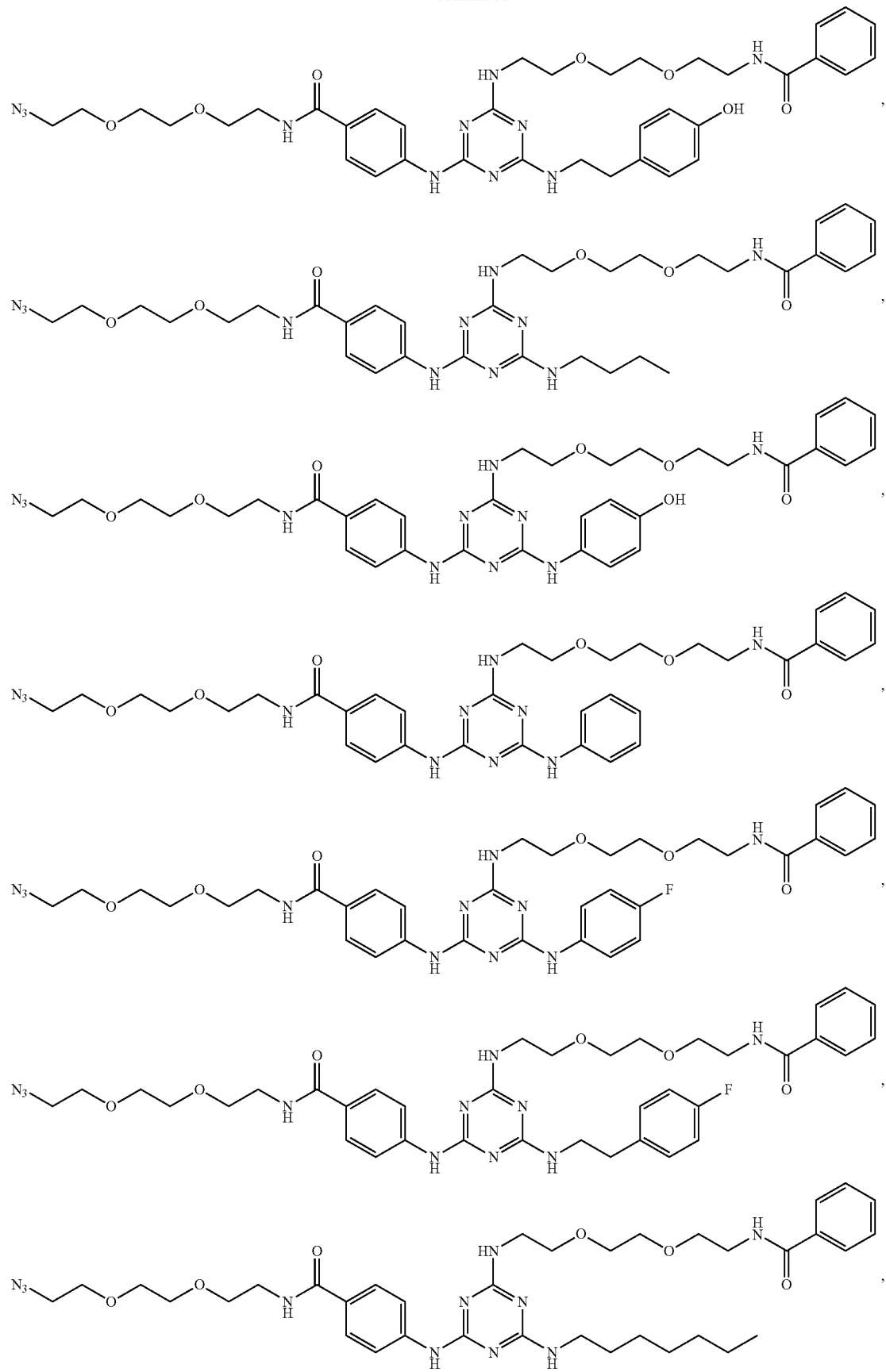

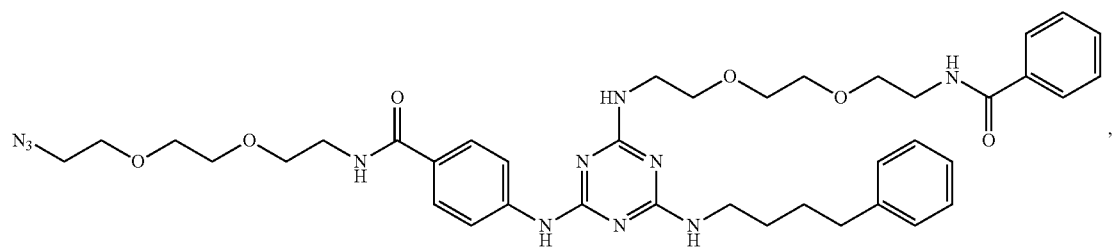,
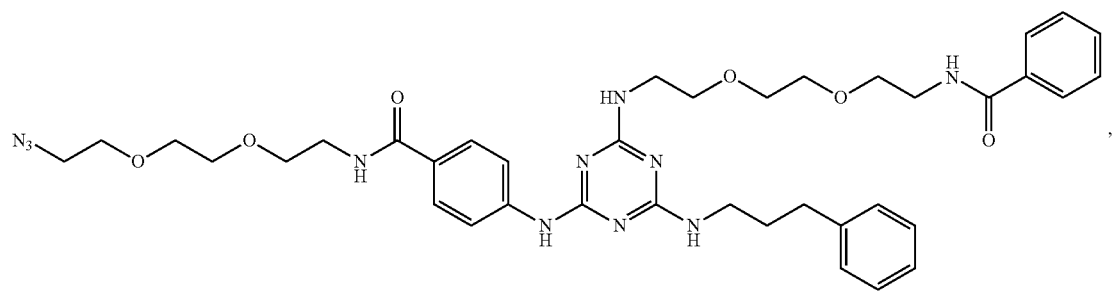,
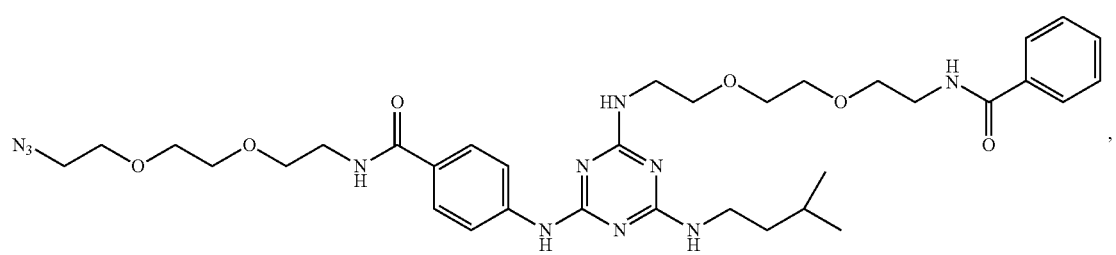,
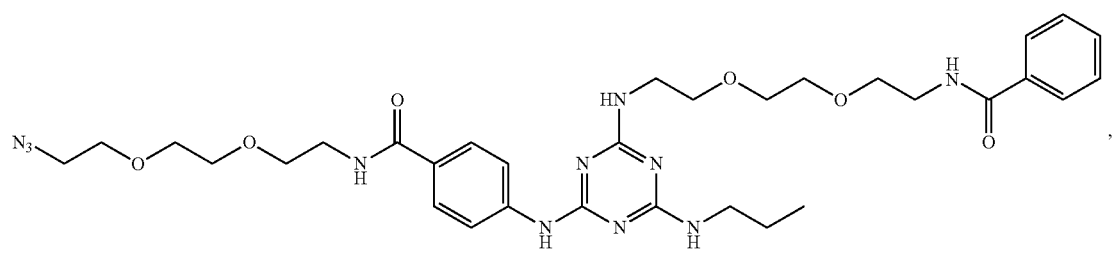,
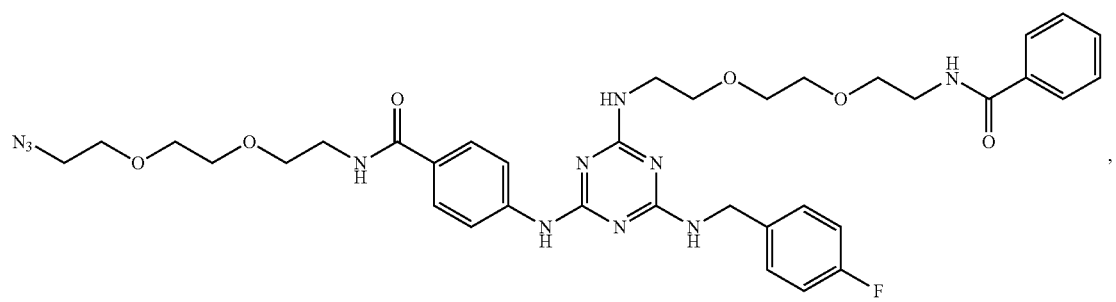,
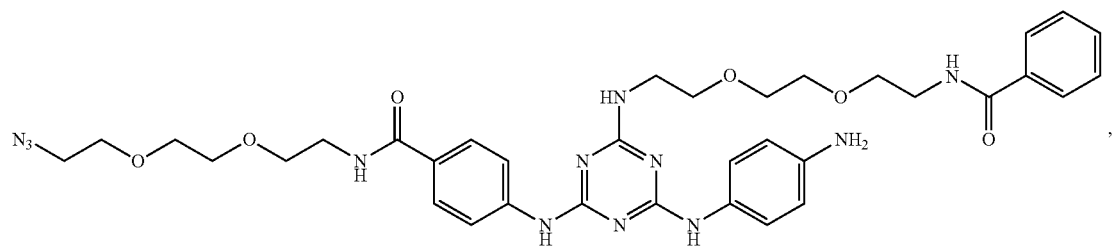,

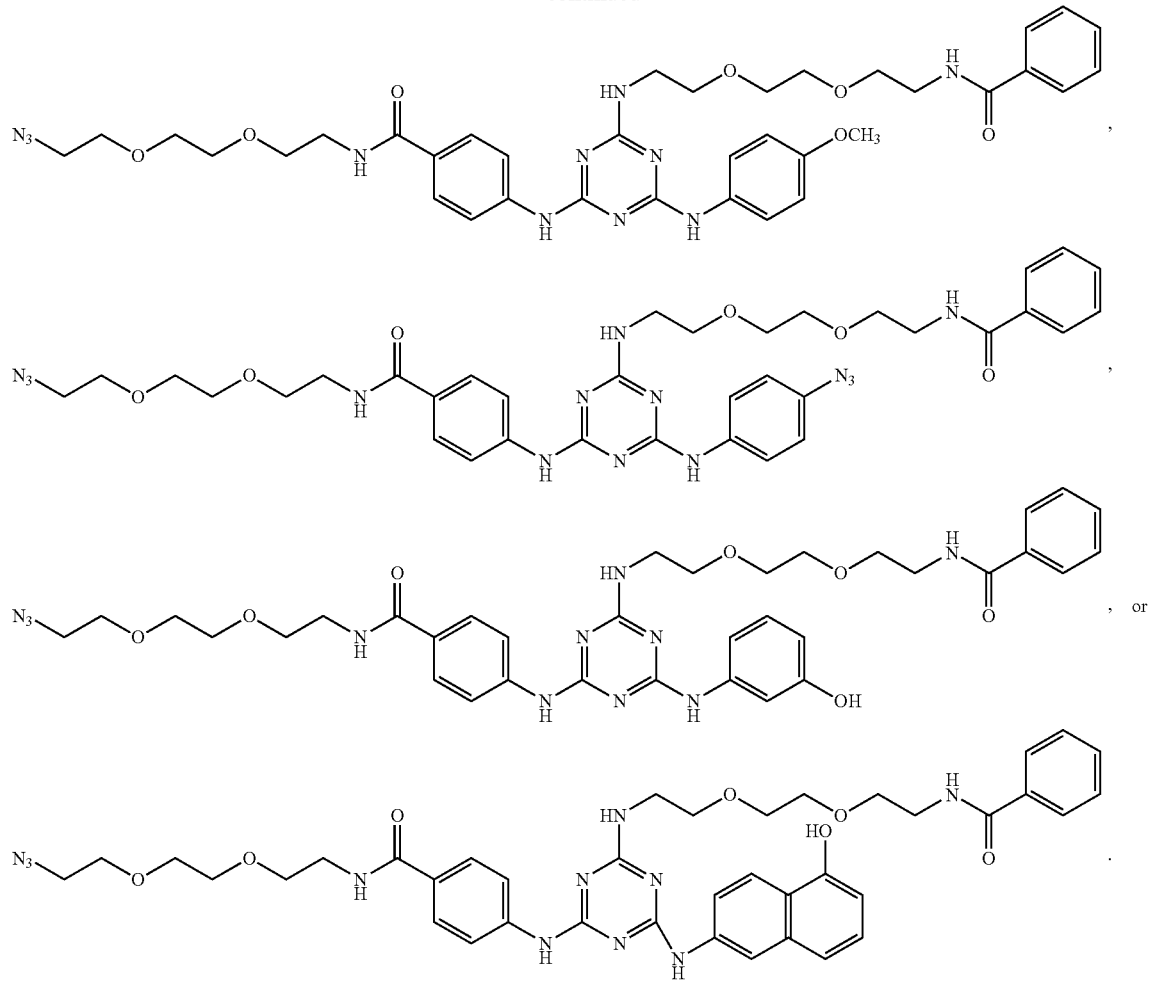

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

Example 1

Identification of a New Class of PGT Inhibitors and Characterization of Their Biological Effects on $PGE_2$ Transport Example Summary Prostaglandins (PGs) are involved in several major signaling pathways. Their effects are terminated when they are transported across cell membranes and oxidized intracellularly. The transport step of PG metabolism is carried out by the prostaglandin transporter (PGT). Inhibition of PGT would therefore be expected to change local or circulating concentrations of prostaglandins, and thus their biological effects. To develop PGT-specific inhibitors with high-affinity, a library of triazine compounds was designed, and 1,842 small molecules were screened by using MDCK cells stably expressing rat PGT. Several effective PGT inhibitors were found. Among them, the most potent inhibitor was TGBz T34, with a $K_i$ of 3.7±0.2 µM. These inhibitors allowed the isolation of the efflux process of $PGE_2$ and the demonstration that PGT does not transport $PGE_2$ outwardly under physiological conditions.

Introduction

Prostaglandins (PGs) are local signaling molecules that trigger pain, fever, and inflammation, among other physiological effects. PG signaling is mediated by cell-surface PG receptors. The PG uptake carrier PGT, which is expressed on the surface of cells that synthesize PGs, removes PGs from the pericellular fluid and thereby determines the set-point of PG receptors at the cell surface.

To develop high-affinity, PGT-specific inhibitors, compounds from a triazine library were screened. Using Madin Darby Canine Kidney (MDCK) cells stably expressing PGT (Endo et al., 2002), screening of 1,842 small molecules yielded several effective inhibitors. The most potent inhibitor in this group of compounds, TGBz T34, has a $K_i$ of 3.7±0.2 µM. This compound also permitted isolation of the efflux process of $PGE_2$ transport and the demonstration that $PGE_2$ influx and efflux are mediated by separate processes.

Methods

Materials.

The cell lines used in this study were 3T3 cells that express endogenous PGT, and MDCK cells stably transfected with the GFP-tagged PGT (Endo et al., 2002). Tritium labeled PGE$_2$ ([$^3$H]PGE$_2$) was purchased from Perkin Elmer. Unlabeled PGE$_2$ was obtained from Cayman.

Synthesis of 1842 Small Molecule Compounds.

The methods and procedures for synthesis of 1842 compounds were reported elsewhere (Moon et al., 2002; Bork et al., 2003a; Bork et al., 2003b; Khersonsky et al., 2003; Uttamchandani et al., 2004).

PGE$_2$ Transport Measurement.

MDCK or 3T3 cells were seeded at 15-20% confluence on 24-well plates. The day on which the cells were seeded was considered day 1. PGE$_2$ uptake experiments were conducted on day 4. All of the PGE$_2$ uptake experiments were conducted at room temperature. On day 4, cells were washed twice with Waymouth buffer (135 mM NaCl, 13 mM H-Hepes, 13 mM Na-Hepes, 2.5 mM CaCl$_2$, 1.2 mM MgCl$_2$, 0.8 mM MgSO$_4$, 5 mM KCl, and 28 mM D-glucose). Then 200 μL of Waymouth buffer containing [$^3$H]PGE$_2$ was added to each well. At the designated time, the uptake of [$^3$H]PGE$_2$ was stopped by aspiration of uptake buffer; this was followed by immediate washing twice with 500 μL of chilled Waymouth buffer. Cells were then lysed with 100 μL lysis buffer containing 0.25% SDS and 0.05 N NaOH. 1.5 mL of scintillation solution was added to each well, and intracellular [$^3$H]PGE$_2$ was counted by MicroBeta Counter.

For preliminary screening of the compounds, 25 μL of Waymouth buffer containing small organic compounds were added to each well; this was immediately followed by the addition of 175 μL of Waymouth buffer containing [$^3$H]PGE$_2$. In each well, the total volume of uptake medium was 200 μL. Organic compounds were first dissolved in DMSO and then diluted in Waymouth buffer. The percent inhibition of [$^3$H]PGE$_2$ uptake by compounds was calculated as [(uptake$_{vehicle}$−uptake$_{inhibitor}$)÷(uptake$_{vehicle}$)]×100.

Measurements of K$_i$ Values.

The initial velocities at various initial extracellular concentrations of PGE$_2$ were determined from the PGE$_2$ uptake in the first 2 minutes; these were linear over the time course of PGE$_2$ uptake. K$_i$ values were obtained by curve fitting the reciprocal of initial velocities of PGE$_2$ uptake versus the reciprocal of extracellular PGE$_2$ concentrations at various concentrations of the inhibitors. At low PGE$_2$ concentrations, the extracellular concentrations were taken as $^3$H labeled PGE$_2$, which has a specific activity of 500 μCi/mol. At high concentrations of PGE$_2$, a mixture of $^3$H labeled and unlabeled PGE$_2$ was made to a final specific activity of 25 μCi/mol.

Results.

Screening of Small Molecules for Inhibition of PGE$_2$ Uptake.

Figure 1:
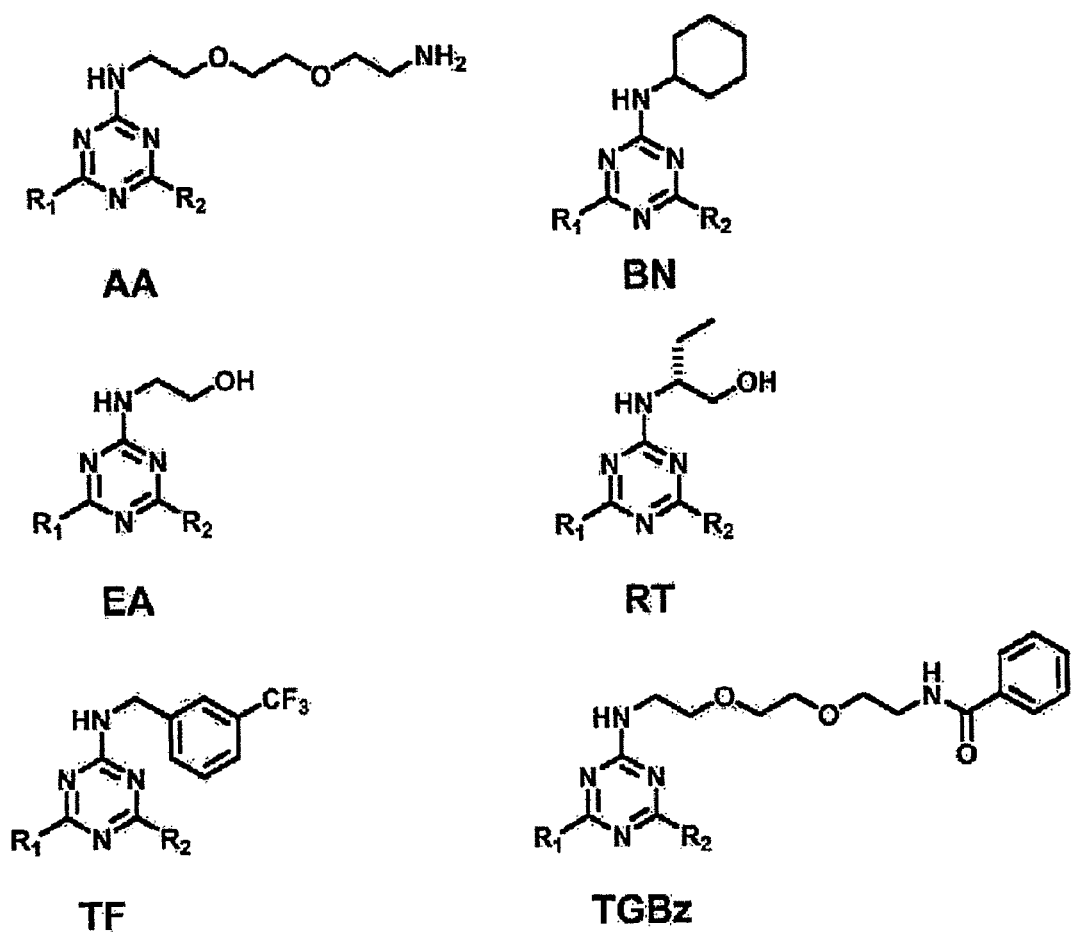
FIG. 1 shows the chemical structures of the main scaffolds used to identify prostaglandin transporter inhibitors.
Figure 5:
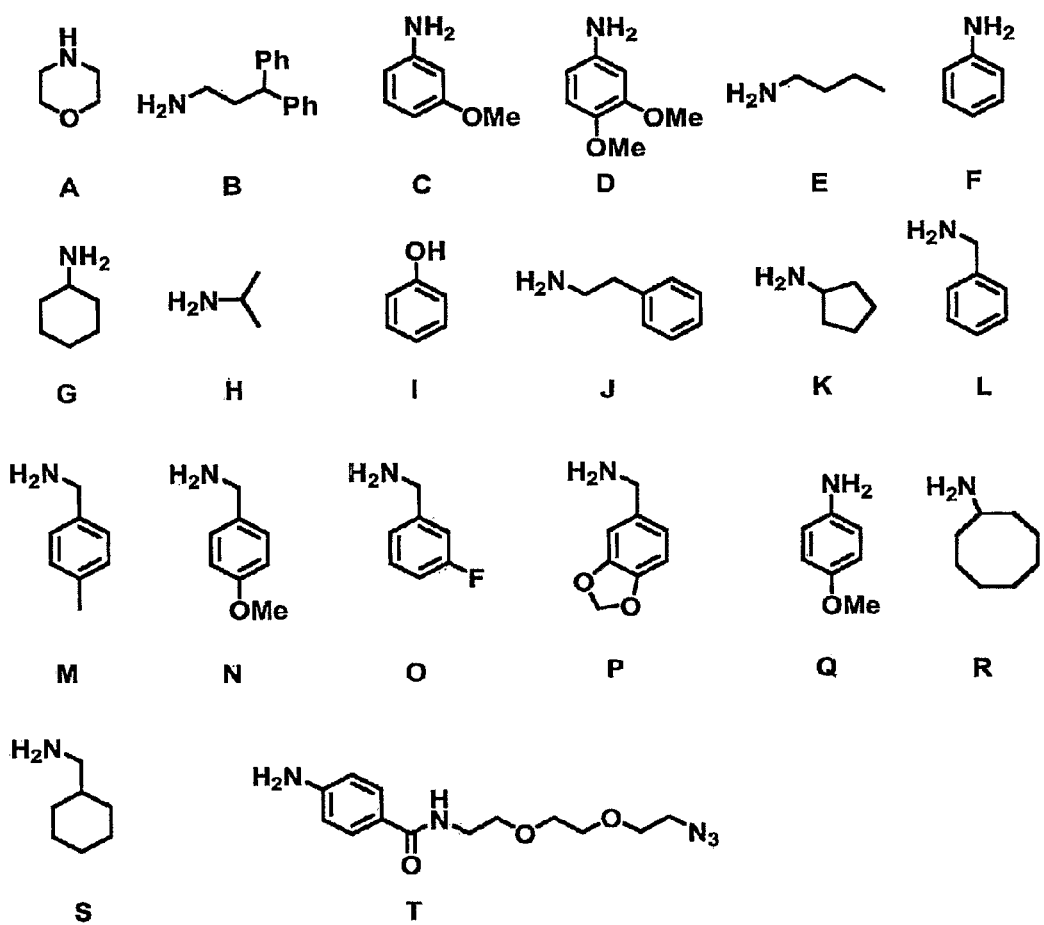
FIG. 5 shows the full set of R1 structures utilized in the library.
Figure 6:
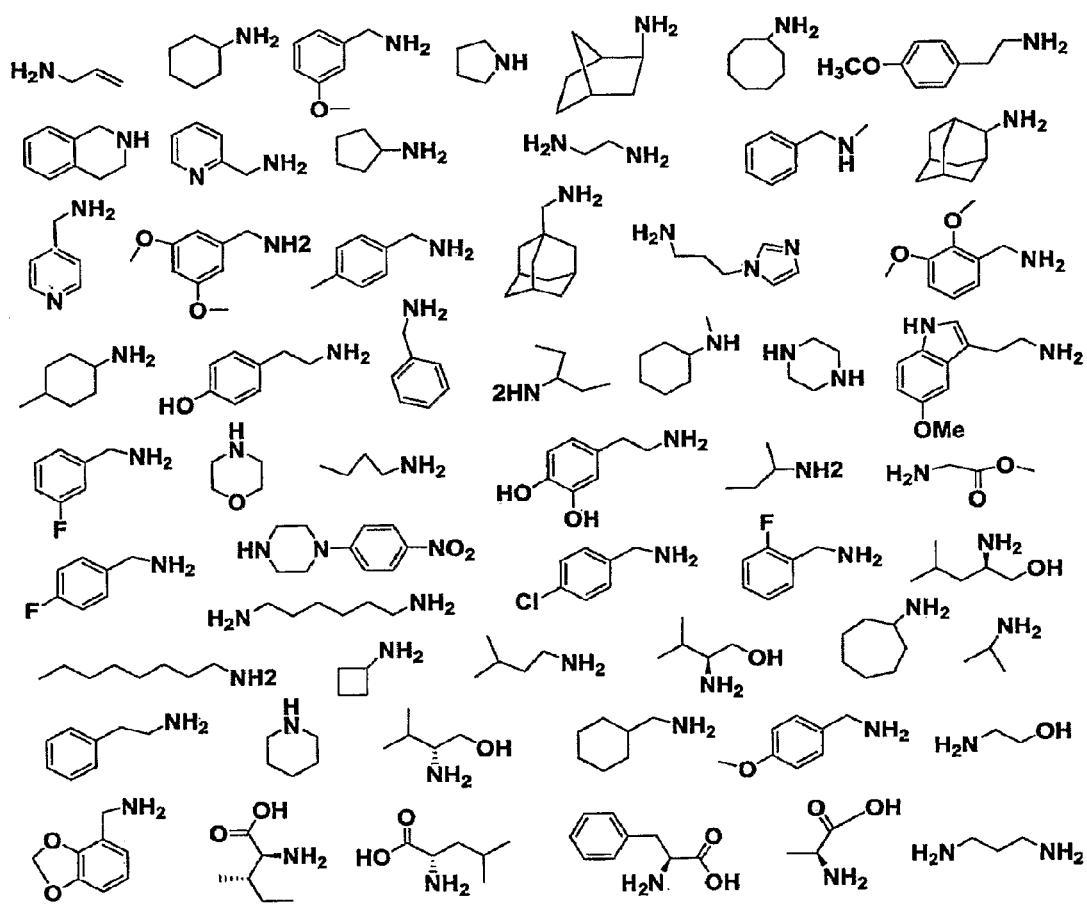
FIG. 6 shows the full set of R2 structures utilized in the library.

The small molecule triazine library compounds (1,842 members) were synthesized following reported procedures (Moon et al., 2002; Bork et al., 2003a; Bork et al., 2003b; Khersonsky et al., 2003; Uttamchandani et al., 2004). The main scaffolds of the compounds are depicted in FIG. 1 with codes of AA, BN, EA, RT, TF, and TGBz. The full structural information on R1 and R2 groups is provided in FIGS. 5 and 6. Among the 1,842 compounds tested, the six compounds with the highest inhibitory activities were all from the TGBz scaffold. The T substituent at the R1 position and an acidic group (COOH or phenol) at the R2 position constitute important motifs for activity.

Determination of K$_i$ Values of Inhibitors and Their Modes of Inhibition.

Figure 2:
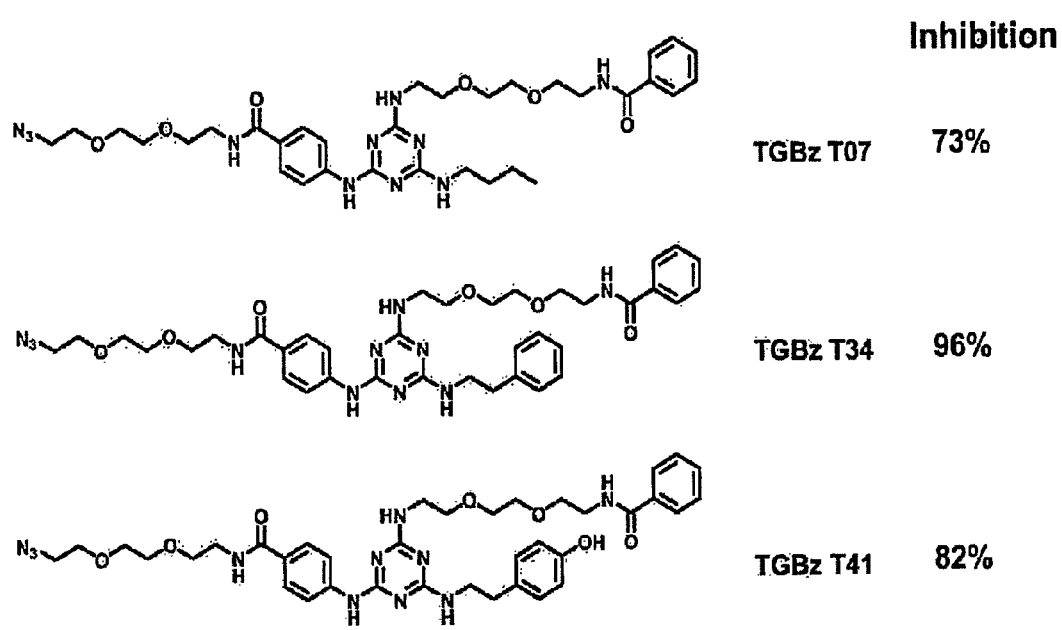
FIG. 2 shows the structures of the three most potent TGBz compounds and their degree of PGT inhibition at 25 µM.
Figure 3:
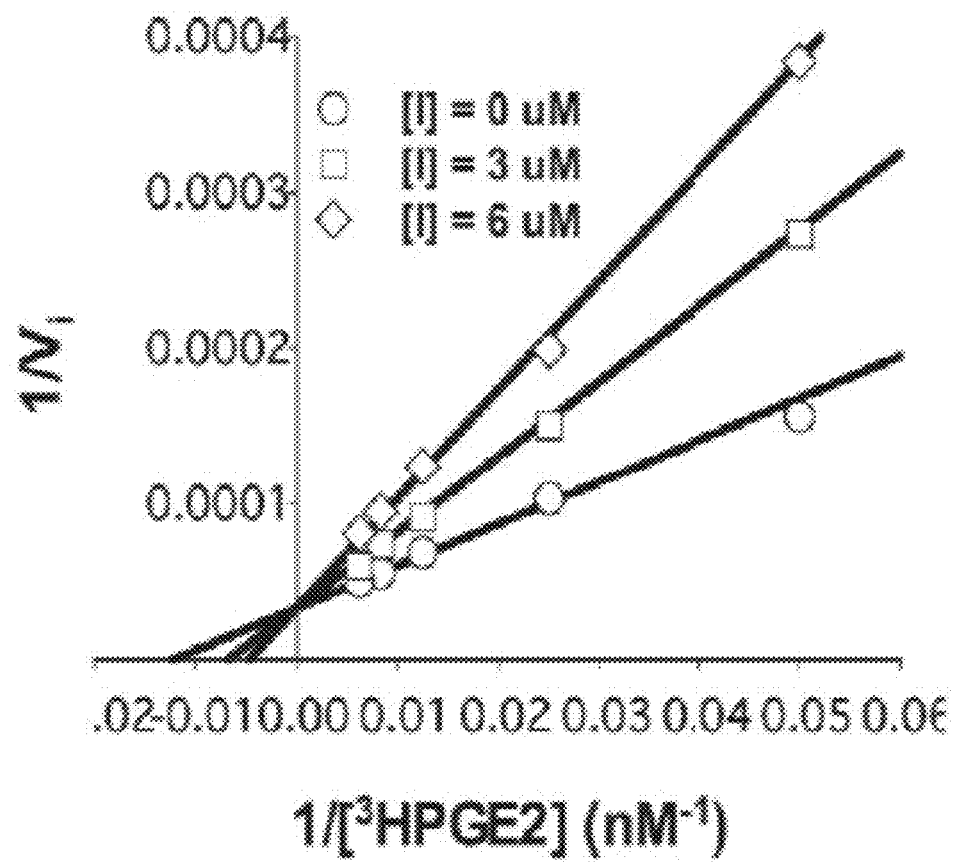
FIG. 3 is a graph of results of a kinetic study to determine the inhibitory effect of TGBz T34 on PGT-mediated $PGE_2$ uptake. The TGBz T34 inhibition constant and its mode of inhibition were determined by varying $PGE_2$ concentration at fixed levels of TGBz T34 equal to 0 µM (circle), 3 µM (square), and 6 µM (diamond). Double-reciprocal plots for TGBz T34 inhibition demonstrate that TGBz T34 is a competitive inhibitor of PGT with a $K_i$ value of 3.7±0.2 µM.
Figure 7:
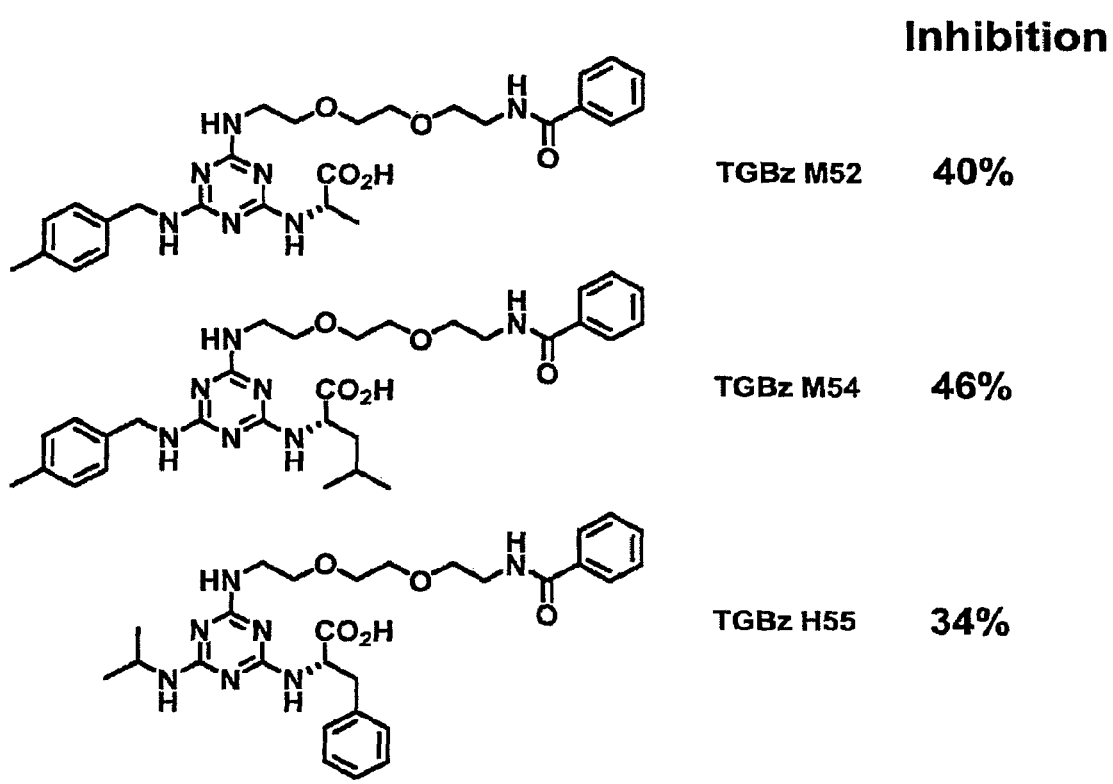
FIG. 7 shows the three of the six initial compounds that were not initially chosen for further study.

Of the six initial compounds, TGBz T34, T07, and T41 (FIG. 2) were chosen to further determine their inhibition kinetic parameters. Structures of the other three compounds are given in FIG. 7. The inhibition constant of TGBz T34 and its mode of inhibition, as determined by varying the PGE$_2$ concentrations at fixed levels of TGBz T34, are shown in FIG. 3. The pattern was characteristic for competitive inhibition. The same experiments were conducted for TGBz T41 and T07; the K$_i$ values are listed in Table 1. All of these compounds are competitive inhibitors of PGT. TGBz T34 is the most potent inhibitor with a K$_i$ of 37±0.2 μM. In separate experiments, when cells were pre-incubated in TGBz T34 for 10 or 20 minutes, the K$_i$ was not significantly different from that obtained by adding TGBz T34 simultaneously with PGE$_2$ (0 min pre-incubation K$_i$=1.22 μM; 10 min pre-incubation K$_i$=1.63 μM; 20 min pre-incubation K$_i$=1.41 μM, NS to each other). These data suggest that there is no significant time dependency of binding of the inhibitor to PGT.

TABLE 1

K$_i$ Values of TGBz Inhibitors of PGT

| Compounds | K$_i$ (μM) |
|---|---|
| T34 | 3.7 ± 0.2 |
| T41 | 6.2 ± 0.7 |
| T07 | 12.5 ± 1.5 |

TGBz T34 Specifically Inhibits PGE$_2$ Uptake by PGT.

Figure 4A:
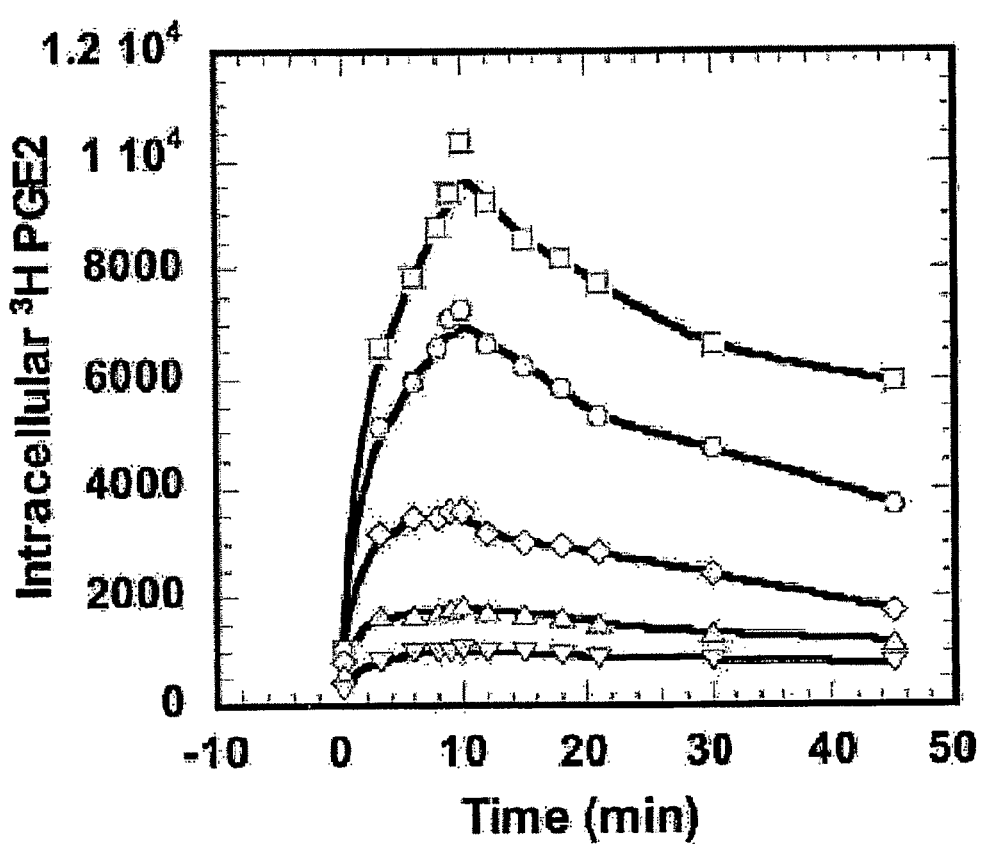
FIG. 4 is graphs and a chart of experimental results showing the time course of $PGE_2$ uptake by of MDCK cells stably expressing PGT. In the experiment of panel A, TGBz T34 was added at various concentrations. TGBz T34 was added at the beginning of each time course at 0 µM (square), 1 µM (circle), 4 µM (diamond), 10 µM (up triangle), 25 µM (down triangle). In the experiment of panel B, the cells were without TGBz T34 (open circle) and with 25 µM TGBz T34 added at the time point at which intracellular $PGE_2$ reached its peak level (solid circle). In the experiment of panel C, 25 µM TGBz T34 was added at different time points on the uptake time course: 3 minutes (up triangle), 6 minutes (down triangle), 9 minutes (diamond), 20 minutes (circle), and 35 minutes (square). Panel D shows initial $PGE_2$ efflux velocities ($V_i$) and their corresponding intracellular $PGE_2$ concentrations as obtained from the data of panel C.

A typical time course of PGE$_2$ uptake in the absence of inhibitor is shown in FIG. 4A (squares). In the absence of TGBz T34, intracellular PGE$_2$ rapidly accumulated, reaching a peak within 9 or 10 minutes. After this overshoot, a plateau was obtained, indicating that the rate of uptake equaled the rate of efflux. These data are similar to those previously published (Chan et al., 1998; Chan et al., 2002).

To further test the inhibition effect of TGBz T34, the time course of PGE$_2$ uptake was measured in the presence of various concentrations of TGBz T34 added at the beginning of uptake. As shown in FIG. 4A, as the concentration of TGBz T34 increased, the peak level of intracellular PGE$_2$ accumulation decreased and the time point for reaching the peak PGE$_2$ level shifted, such that it took a shorter time for intracellular PGE$_2$ to reach its peak level at higher concentrations of TGBz T34. Also, as the concentration of TGBz T34 increased, the overshoot phenomenon diminished. When the concentration of TGBz T34 was 25 μM, i.e. 8 fold higher than its K$_i$, the overshoot phenomenon completely disappeared. The residual uptake reflects PGE$_2$ entry by diffusion; it is similar to the curve of PGE$_2$ uptake by wild-type MDCK cells before they were transfected with PGT (Endo et al., 2002). Similar overshoot data and inhibition by TGBz T34 were obtained in Swiss 3T3 cells expressing endogenous PGT (data not shown).

PGT does not export PGE$_2$.

Figure 4B:
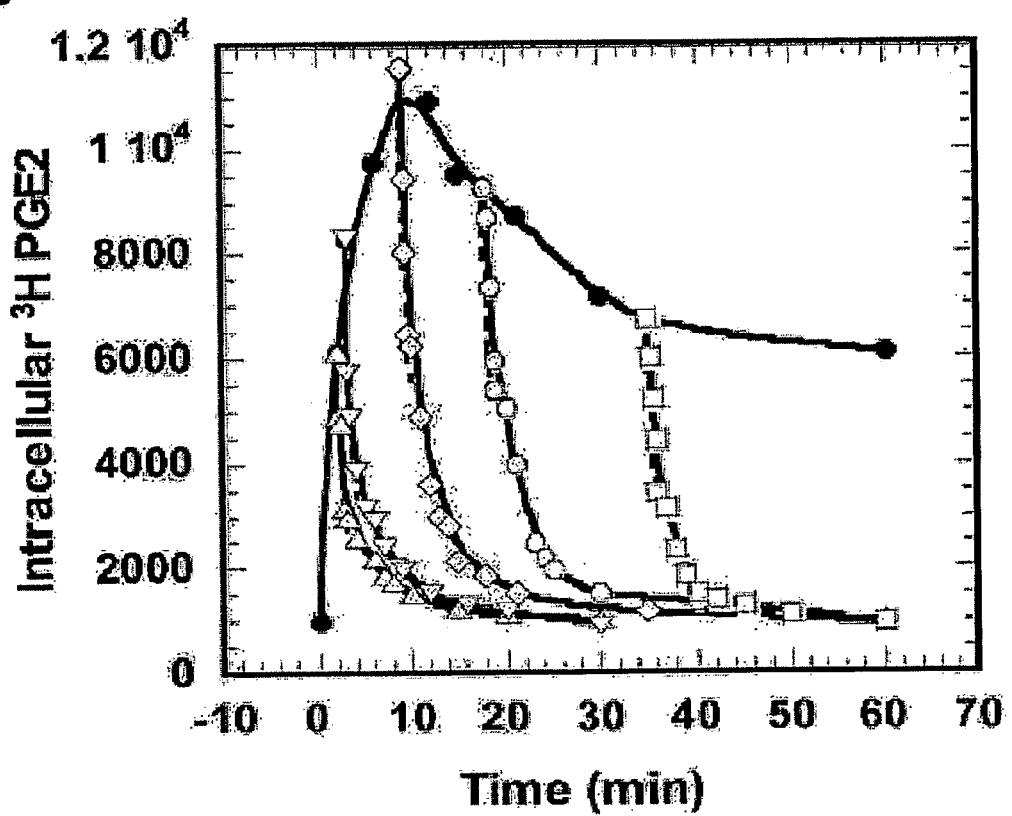

Since the discovery of PGT, the issue of whether it transports PGs in both directions has been unsettled (Chan, et al., 1998; Schuster, 2002; Banu et al., 2003). To resolve this issue, TGBz T134 was applied after loading intracellular PGE$_2$ to a peak level (9 minutes) so as to block all PGE$_2$ transport by PGT, and then the efflux of PGE$_2$ was monitored. As shown in FIG. 4B, addition of TGBz T34 at 25 μM induced a rapid depletion of intracellular PGE$_2$. Intracellular PGE$_2$ fell to baseline within 5 minutes and remained at that level for the rest of the time course. When there was no addition of T34, intracellular PGE$_2$ stayed at a much higher level. This result strongly suggests that PGT does not participate in PGE$_2$ efflux. Instead, efflux occurs by either simple diffusion or by a combination of diffusion and another very low-affinity carrier.

PGE$_2$ Efflux Occurs by Simple Diffusion.

Figure 4C:
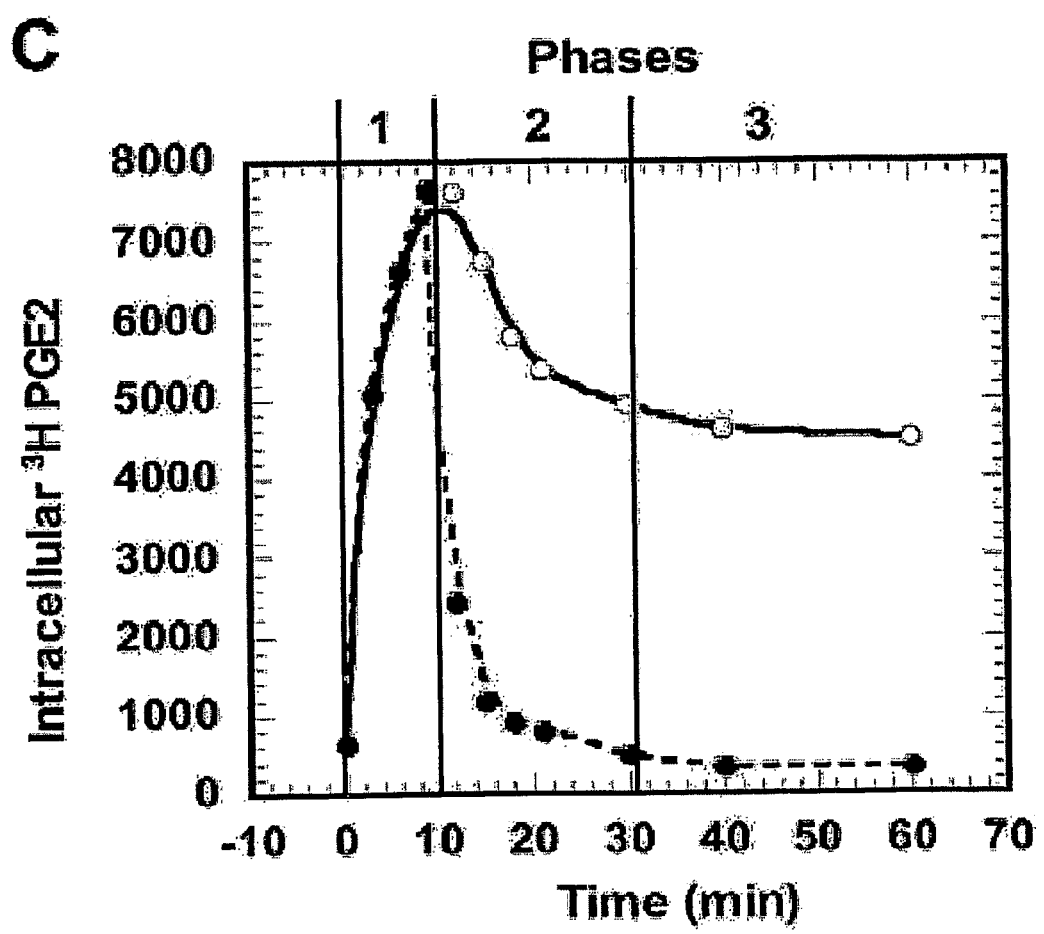

We used TGBz T34 to further isolate the efflux process of PGE$_2$. As shown in FIG. 4C, we allowed PGE$_2$ uptake to proceed to different time points (3, 6, 9, 20, and 35 minutes) and then added 25 μM T34 to stop the accumulation. The intracellular concentrations of $PGE_2$ at different time points were calculated by dividing the total amount of intracellular $PGE_2$ on the dish by the total volume of cells, based on cell number counts and published individual cell volume (Schneider et al., 2000; Hill et al., 2004). Since the addition of inhibitor involved removing extracellular tracer $PGE_2$, the intracellular $PGE_2$ concentration at the point of inhibitor addition approximates the outwardly-directed $PGE_2$ gradient. Initial $PGE_2$ efflux rates at various $PGE_2$ outward gradients are shown in FIG. 4D.

Initial $PGE_2$ efflux rates from FIGS. 4C and 4D were linear as a function of the outwardly-directed $PGE_2$ gradients over the range of 0 to 30 nM, with a "y" intercept not significantly different from zero (efflux rate=[(0.0106)(gradient)]+0.048, $r^2$=0.98, p<0.05). This linearity held true even when the intracellular $PGE_2$ concentration was extended to almost 800 nM, i.e. 10 fold the $K_m$ of PGT for $PGE_2$ (data not shown). From the slope of the relationship, we generated a range of permeability coefficients for $PGE_2$ efflux of 1.2 to $5.3\times10^{-6}$ cm/sec, based on the range of MDCK cell volumes reported in the literature (Schneider et al., 2000; Hill et al., 2004). Using wild-type MDCK cells that do not express PGT, a permeability coefficient for $PGE_2$ influx (by simple diffusion) of $0.45\times10^{-6}$ cm/sec was obtained (data not shown). The ratio of the influx-to-efflux permeability coefficients was thus in the range 2.7 to 117.

Discussion

Organic dyes and nonsteroidal anti-inflammatory drugs have been known to inhibit PGT for some time (Kanai et al., 1995). This is the first report of a new class of PGT inhibitors developed by screening small molecules. The compound library was built by solid-phase combinatorial chemistry and screened by MicroBeta scintillation counting on multi-well plates. This strategy led to the discovery of a PGT inhibitor, TGBz T34, with a $K_i$ of 3.7±0.2 µM, after screening fewer than 2000 compounds. At 25 µM, TGBz T34 exerted full inhibition of $PGE_2$ transport by PGT. Double reciprocal analysis revealed that T34 is a competitive inhibitor of PGT. Because T34 eliminated PGT transport activity rapidly, it probably inhibits PGT directly rather than indirectly via metabolic effects.

The $K_i$ of TGBz T34 is similar to that of bromcresol green (Kanai et al., 1995). TGBz T34 has the potential to be improved because there are three moieties around the scaffold that can be modified. Native substrates of PGT all possess a COOH group and are negatively charged at physiological pH (Schuster, 1998). The carboxylic group at carbon 1 is critical for PG binding to PGT (Eling et al., 1977; Schuster et al., 2000), which is probably why group B (FIG. 7) was associated with inhibition.

Figures 1, 20:
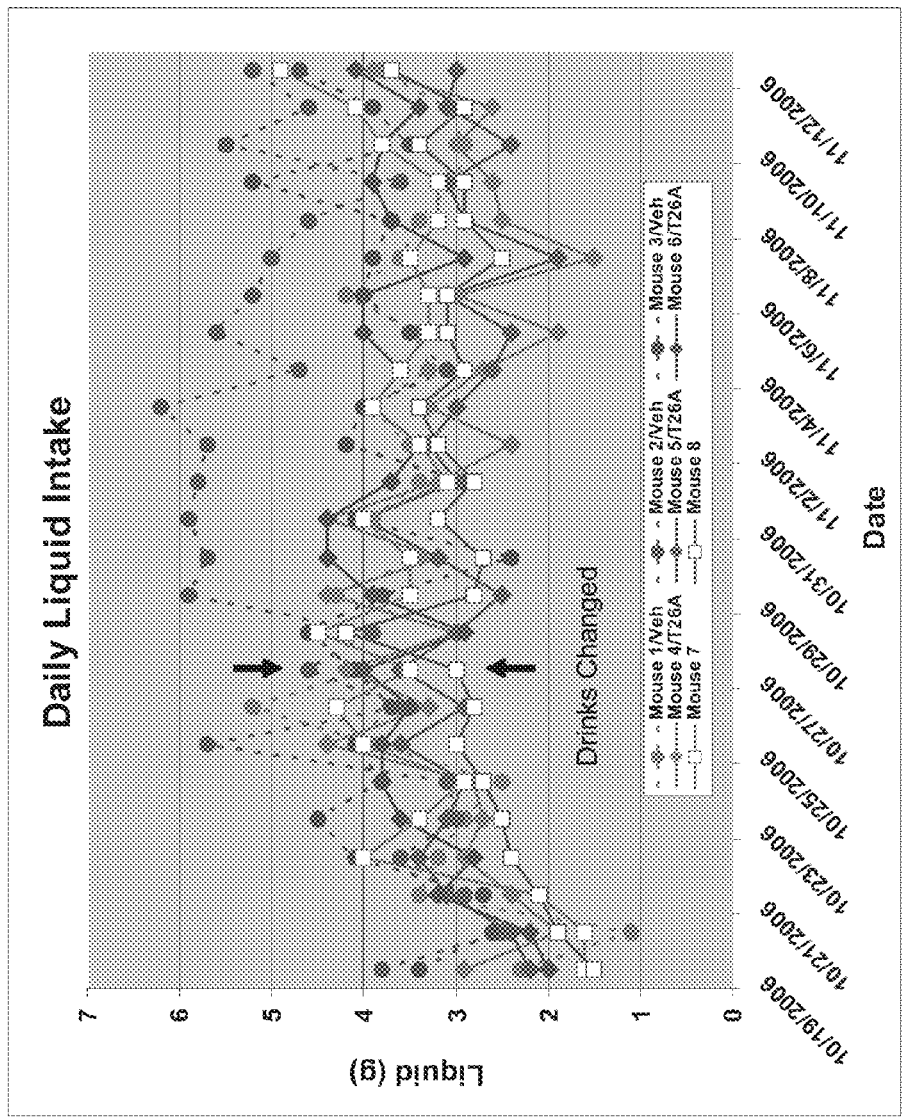
FIG. 20 is four graphs showing that chronic oral administration of T26A does not have any apparent effects on water and food intake, body weight or daily urine volume.
Figures 2, 20:
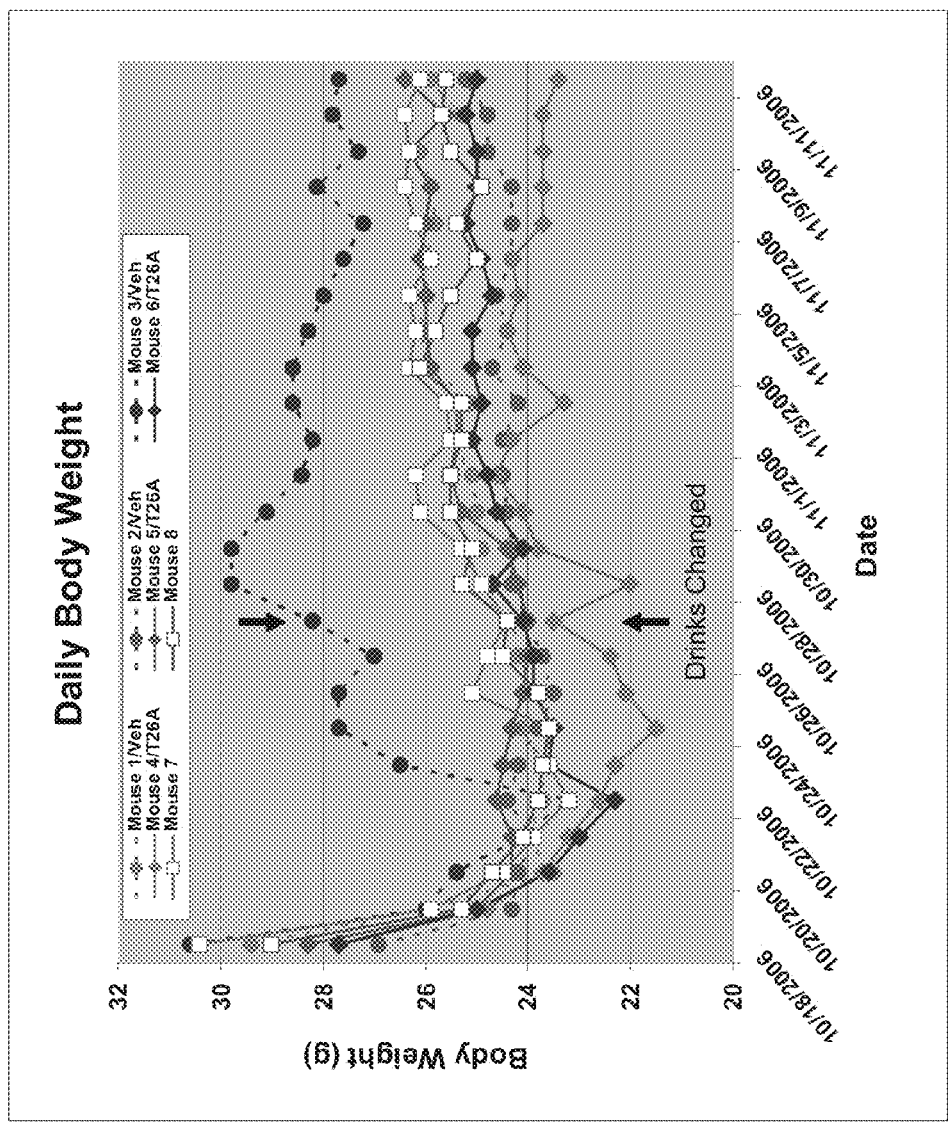
Figures 3, 20:
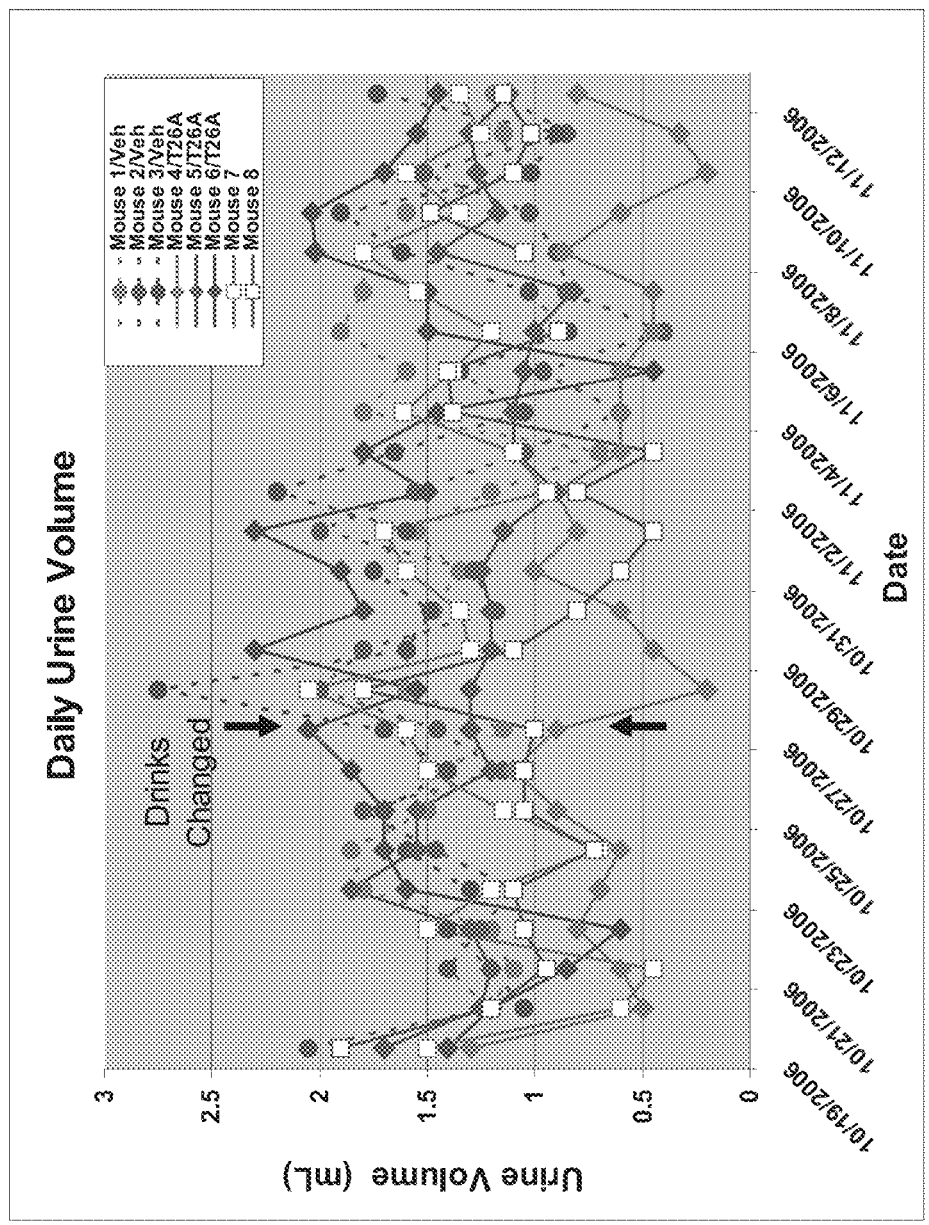
Figures 4, 20:
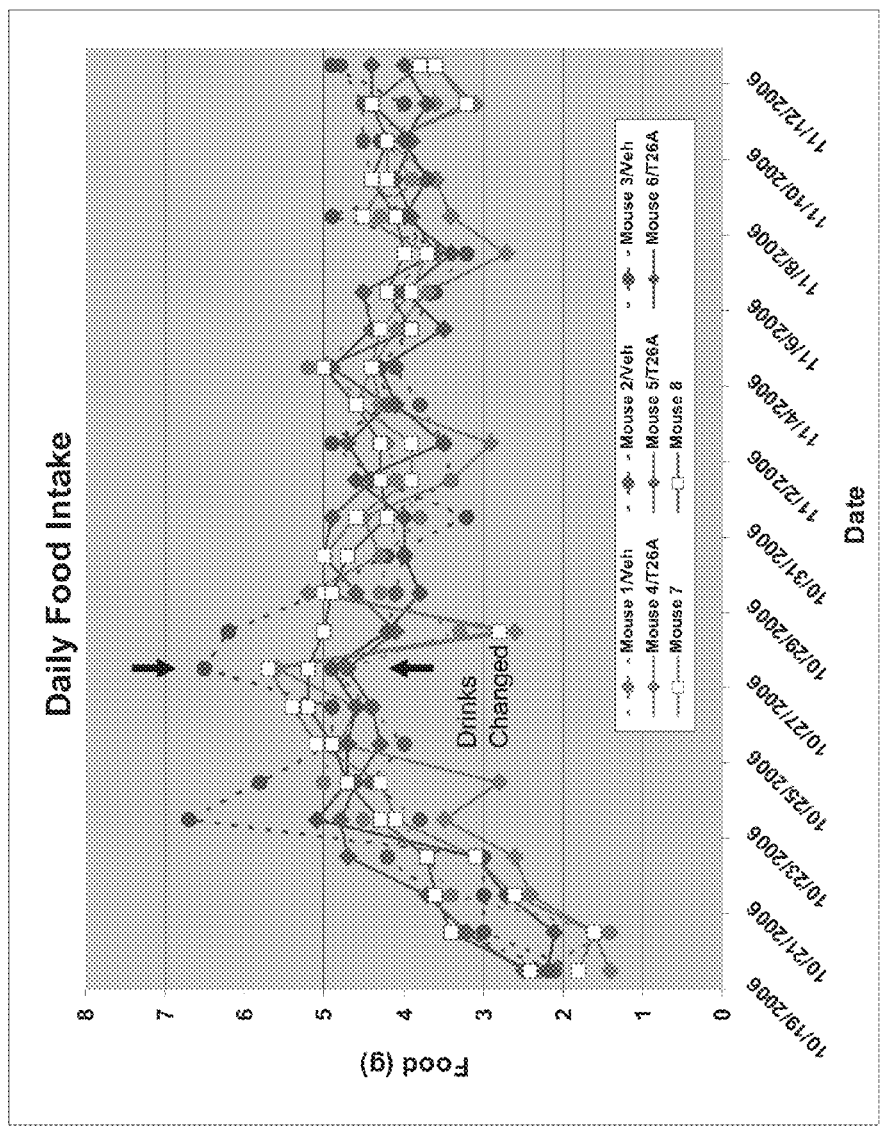

Some investigators have hypothesized that PGT represents the mechanism by which PGs efflux from cells (Funk, 2001; Banu et al., 2003), whereas others have invoked active pumps such as MRP4 (Reid et al., 2003). Identification of these inhibitors enabled an investigation into the mechanism of $PGE_2$ transport in a more refined way. As reported previously (Chan et al., 1998; Schuster, 2002) and in the present study, a normal time course of $PGE_2$ transport is divided into three phases (FIG. 4). Phase 1 is rapid uptake, phase 2 is overshoot, and phase 3 is an equilibrium phase. Addition of T34 at the point of peak intracellular $PGE_2$ accumulation demonstrated that $PGE_2$ efflux is ongoing during PGT-mediated uptake (FIG. 4) i.e. the accumulation of intracellular $PGE_2$ in phase 1, and the maintenance of the equilibrium in phase 3, are due to the active pumping of $PGE_2$ into the cells by PGT against a background efflux.

Using TGBz T34 the isolation of the components of $PGE_2$ efflux was possible. After loading cells with $PGE_2$ and blocking PGT-mediated uptake with T34, the $PGE_2$ efflux rate was linear as a function of the estimated outwardly-directed PG gradient, even at high concentrations. These data indicate that $PGE_2$ efflux, at least from the compartment loaded by PGT, most likely occurred by simple diffusion.

The hypothesis that $PGE_2$ efflux occurs by simple diffusion is further supported by our calculated permeability coefficients. At physiological pH, PGs are negatively charged. Because the cell interior is electrically negative, the electrical driving force for simple diffusion is in favor of $PGE_2$ efflux. The theoretical ratio of the permeability coefficients for diffusional efflux compared to diffusional influx, based on the membrane potential, is in the range of 2-11 (Schuster, 2002). The ratios we generated agree with this range. Taken together, our data support a model of $PGE_2$ transport as a pump (PGT-mediated influx)–leak (diffusional efflux) system.

In summary, reported here is the development of a new class of PGT inhibitors by screening a library of small molecules. The most potent of these allowed the clarification of the mechanisms for influx and efflux of $PGE_2$. This compound and others should form the basis for further pharmacological investigation of PG transport and should serve as lead compounds in developing therapeutic agents.

Example 2

Additional PGT Inhibitors and Effect of PGT Inhibition on COX-2 Activity

Structurally agnostic screening was carried out with ~2,000 organic small molecules that were modified from lead compounds T34 and T41, described in Example 1. The most effective, compound TGBZ T26A, competitively inhibits PGT at a Ki=300 nM.

Table 2 provides the PGT inhibitors from this screening that showed greater than 50% inhibition at 5 µl.

TABLE 2

| Code | Structure | % Inhib. at 5 µM | $K_i$ (µM) |
|------|-----------|------------------|------------|
| T34 | 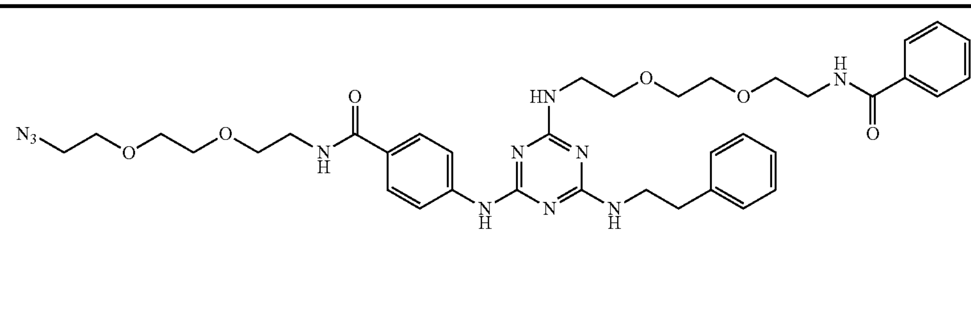 | 84 | 3.7 |

TABLE 2-continued
| Code | Structure | % Inhib. at 5 μM | $K_i$ (μM) |
|---|---|---|---|
| T41 | 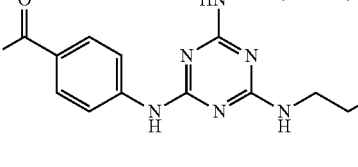 | 65 | 6.2 |
| T26A | 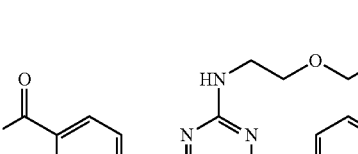 | 92 | 0.38 |
| T28A | 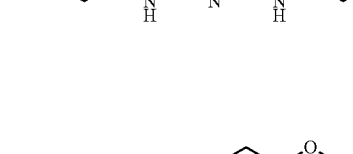 | 84 | 3.6 |
| T25A | 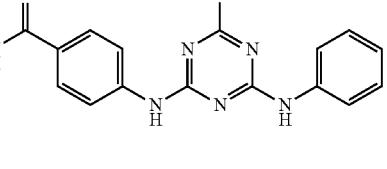 | 82 | 3.9 |
| T18A | 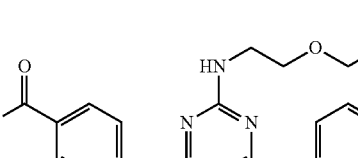 | 76 | |
| T07A | 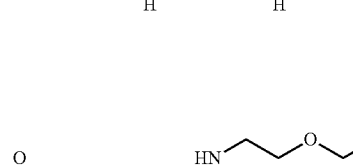 | 74 | |

TABLE 2-continued

| Code | Structure | % Inhib. at 5 µM | $K_i$ (µM) |
|------|-----------|------------------|------------|
| T22A | 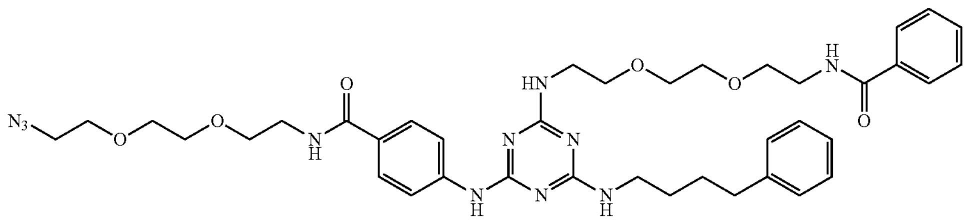 [SMILES: [N-]=[N+]=NCCOCCOCCNC(=O)c1ccc(Nc2nc(NCCCCc3ccccc3)nc(NCCOCCOCCNC(=O)c3ccccc3)n2)cc1] | 72 | |
| T21A | 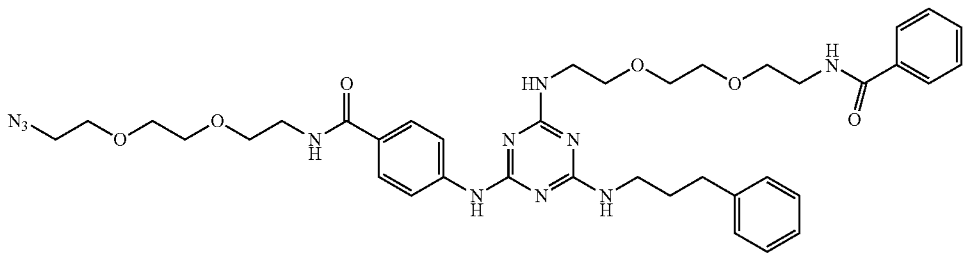 [SMILES: [N-]=[N+]=NCCOCCOCCNC(=O)c1ccc(Nc2nc(NCCCc3ccccc3)nc(NCCOCCOCCNC(=O)c3ccccc3)n2)cc1] | 72 | |
| T08A | 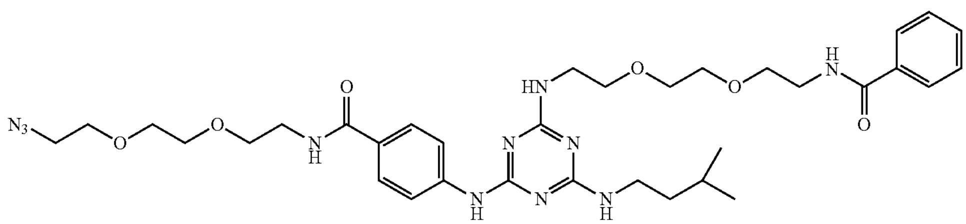 [SMILES: CC(C)CCNc1nc(NCCOCCOCCNC(=O)c2ccccc2)nc(Nc2ccc(C(=O)NCCOCCOCCN=[N+]=[N-])cc2)n1] | 64 | |
| T14A | 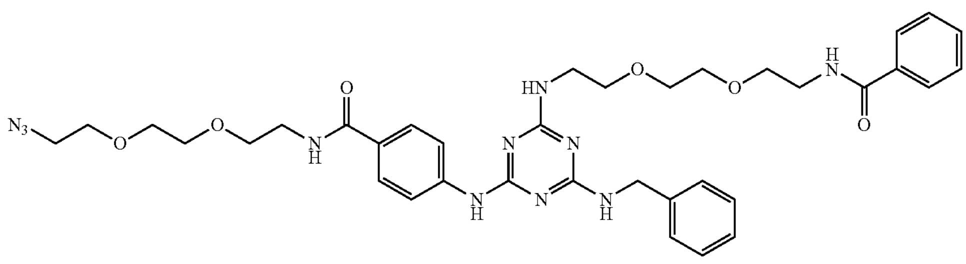 [SMILES: [N-]=[N+]=NCCOCCOCCNC(=O)c1ccc(Nc2nc(NCCOCCOCCNC(=O)c3ccccc3)nc(NCc3ccccc3)n2)cc1] | 56 | |
| T03A | 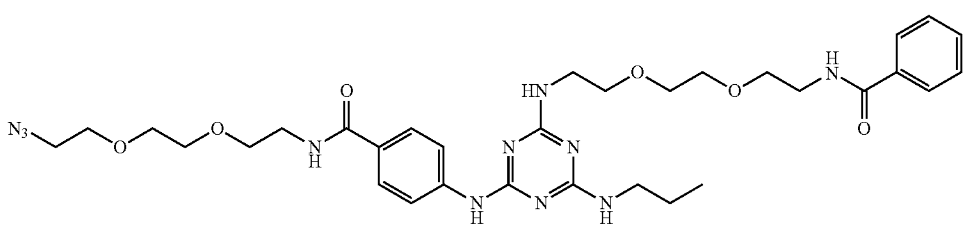 [SMILES: CCCNc1nc(NCCOCCOCCNC(=O)c2ccccc2)nc(Nc2ccc(C(=O)NCCOCCOCCN=[N+]=[N-])cc2)n1] | 54 | |

Data is provided below that shows that a PGT inhibitor down-regulates PG receptor cell surface expression which, in turn, down-regulates Cox-2, the enzyme synthesizing those PGs that mediate fever, pain, and inflammation.

The inventors have formulated a model for PGT regulation of $PGE_2$ receptor (EP) expression. A diagram of the model is provided as FIG. 8, in that model, PGT regulates pericellular prostaglandin $E_2$ [$PGE_2$] by internalizing the $PGE_2$, making it unavailable for binding to cell-surface EP receptors. The binding of $PGE_2$ to the EP receptors causes internalization of the receptors, and PGT prevents this binding by internalizing $PGE_2$. This sensitizes the cell to subsequent $PGE_2$ exposure, causing more extensive prostaglandin signaling. Thus, the cell with PGT (FIG. 8 right) is sensitized to $PGE_2$ whereas the cell without PGT or with PGT inhibited (FIG. 8 left) is desensitized to $PGE_2$. The experiments shown in FIGS. 9 and 10 support this model.

$EP_4$ expression in MDCK cells that constitutively express PGT was tested by determining $PGE_2$ binding to the cells. Wild type MDCK cells and MDCK cells stably expressing PGT were transiently transfected with human cDNA of $EP_4$ (UMR cNDA Resource Center, www.cdna.org). About 30 hours after transfection, the cells were incubated in Waymouth buffer containing 0 and 20 nM of unlabeled $PGE_2$, and either 4% vehicle (DMSO) or 5 µM T26A, for 10 minutes at 37° C. The cells were then washed with PBS buffer and lysed the cells with lysing buffer containing 10 mM TrisHCl, pH, 7.5, 5 mM EDTA, 100 nM okadaic acid, and 20 µM indomethacin. The cells were then harvested and homogenized using a Potter-Elvehiem homogenizer in an ice cold solution containing 10 mM Tris-HCl, pH. 7.4, 1 mM EDTA, 0, 1 mM phenylmethylsulfonyl fluoride, 20 µM indomethacin, then centrifuged the homogenate at 800 g for 5 minutes. The supernatant was transferred to another tube and centrifuged at 19000 rpm for 45 minutes. The supernatant was then discarded and the pellets washed with buffer A containing 20 mM HEPES-NaOH, pH. 7.4, 1 mM EDTA, 10 mM $MgCl_2$. These are extracted cell membranes for the following binding assay. The membranes were incubated in Buffer A containing 5 nM of $^3H$ $PGE_2$ at 30° C. for 1 hour. EP4 bound to $^3H$-$PGE_2$ were quantified as described by Negishi et al., 1987. Nonspecific binding was determined by using 1000-fold excess of unlabeled $PGE_2$ in the incubation mixture. The specific binding was calculated by subtracting the nonspecific bind value from the total binding value (Nishigaki et al., 1996).

Figure 9:
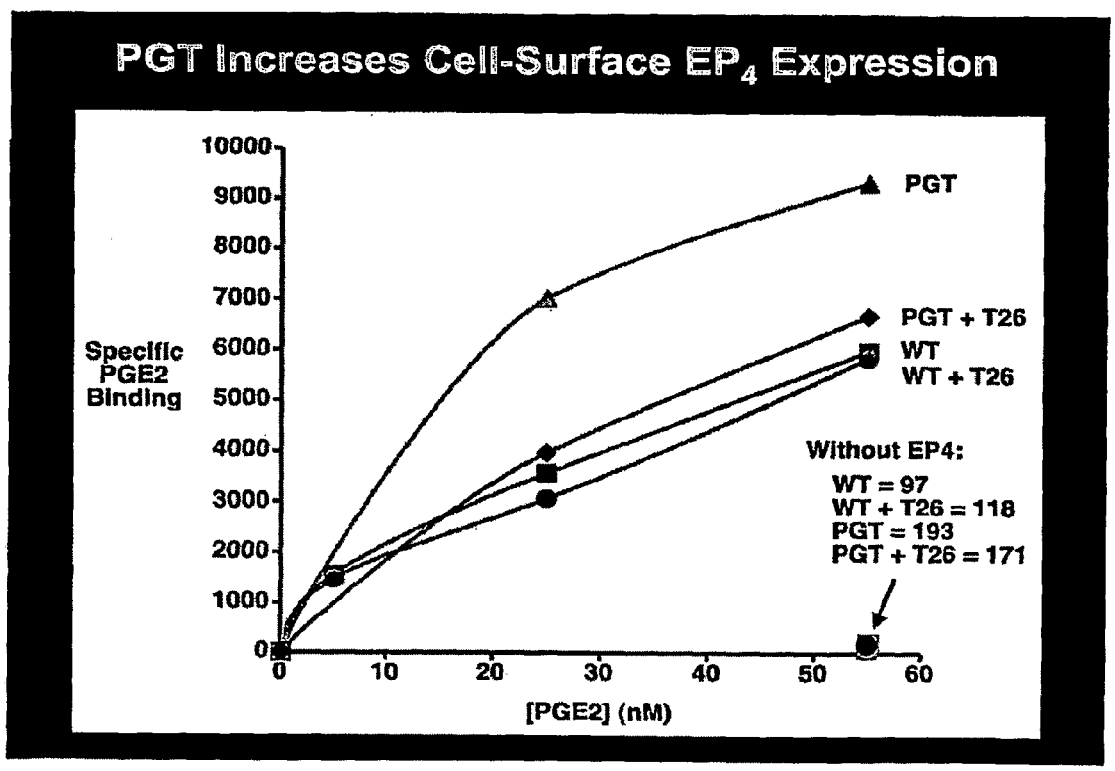
FIG. 9 is a graph of experimental results showing the modulation of high-affinity $EP_4$ binding sites by PGT in MDCK cells. In each analysis, non-specific $PGE_2$ binding has been subtracted out.

The results are provided in FIG. 9. The cluster of overlapping data points at lower right (at [$PGE_2$]=55 nM) indicates lack of significant $PGE_2$ binding in the absence of $EP_4$ transfection. The upper curves show that inducing PGT expression increases $PGE_2$ binding to $EP_4$ compared to WT without PGT, and that inhibition of PGT transport function with T26 abrogates this effect.

Figure 10:
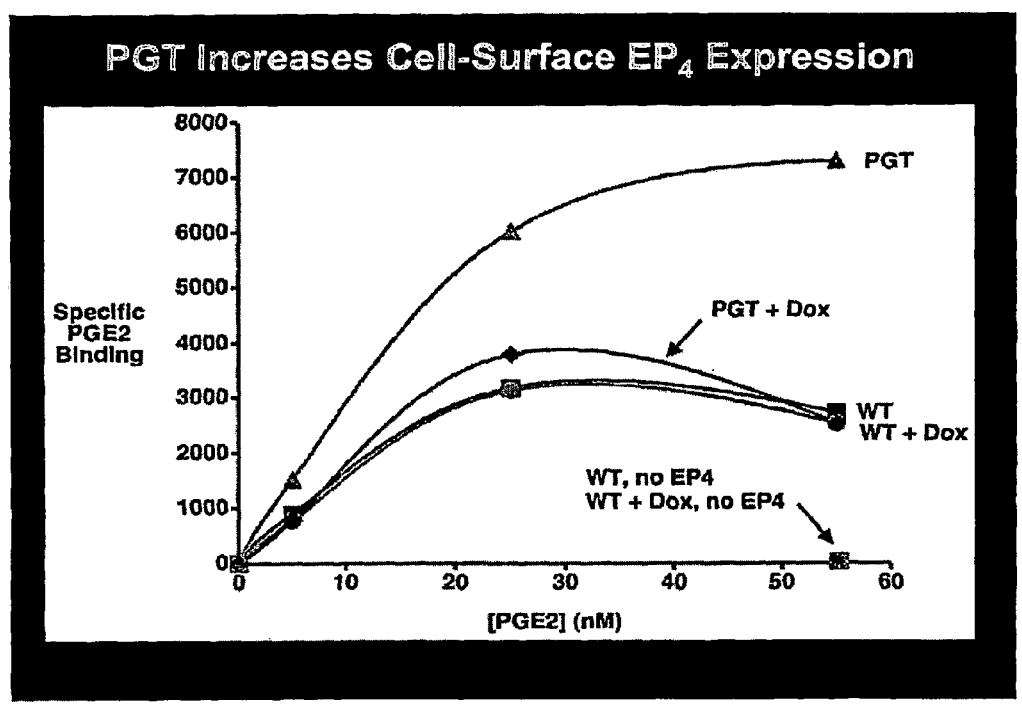
FIG. 10 is a graph of experimental results also showing the modulation of high-affinity $EP_4$ binding sites by PGT in MDCK cells. This is a similar study to that of FIG. 9, except that in this case PGT expression is either permitted, or is suppressed with doxycycline (Dox). Data points on the x-axis at [PGE$_2$]=55 nM indicate absence of PGE$_2$ binding without EP$_4$ transfection.

In the similar studies shown in FIG. 10, expression of PGT expression was either permitted, or is suppressed with doxycycline (Dox). The upper curves show that expressing PGT increases $PGE_2$ binding to $EP_4$, whereas suppressing PGT expression (+Dox) reduces $PGE_2$ binding down to the level of WT cells.

Figure 11:
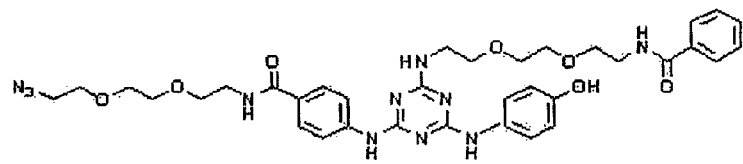
FIG. 11 shows the structure of TGBZ T26, the most potent PGT inhibitor identified in this study.
Figure 12:
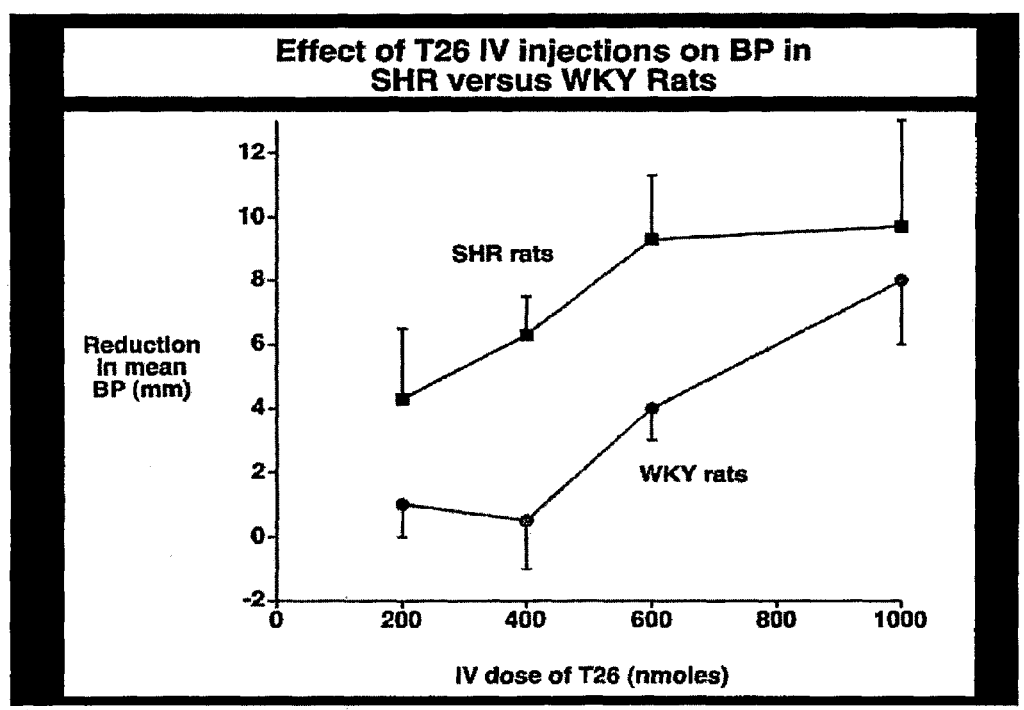
FIG. 12 is a graph of experimental results showing a dose response of T26 IV injections on systemic BP in anesthetized rats of the control strain (WKY) and the Spontaneously Hypertensive Rat (SHR) strain.

Of the PGT inhibitors described above, the most potent PGT inhibitor is TGBZ T26 (FIG. 11—called T26A in Table 2). The effect of T26 IV injections on systemic BP in anesthetized rats of a control strain (WKY) and the Spontaneously Hypertensive Rat (SHR) strain was evaluated. As shown in FIG. 12, T26 reduced the blood pressure of both rats.

Figure 13:
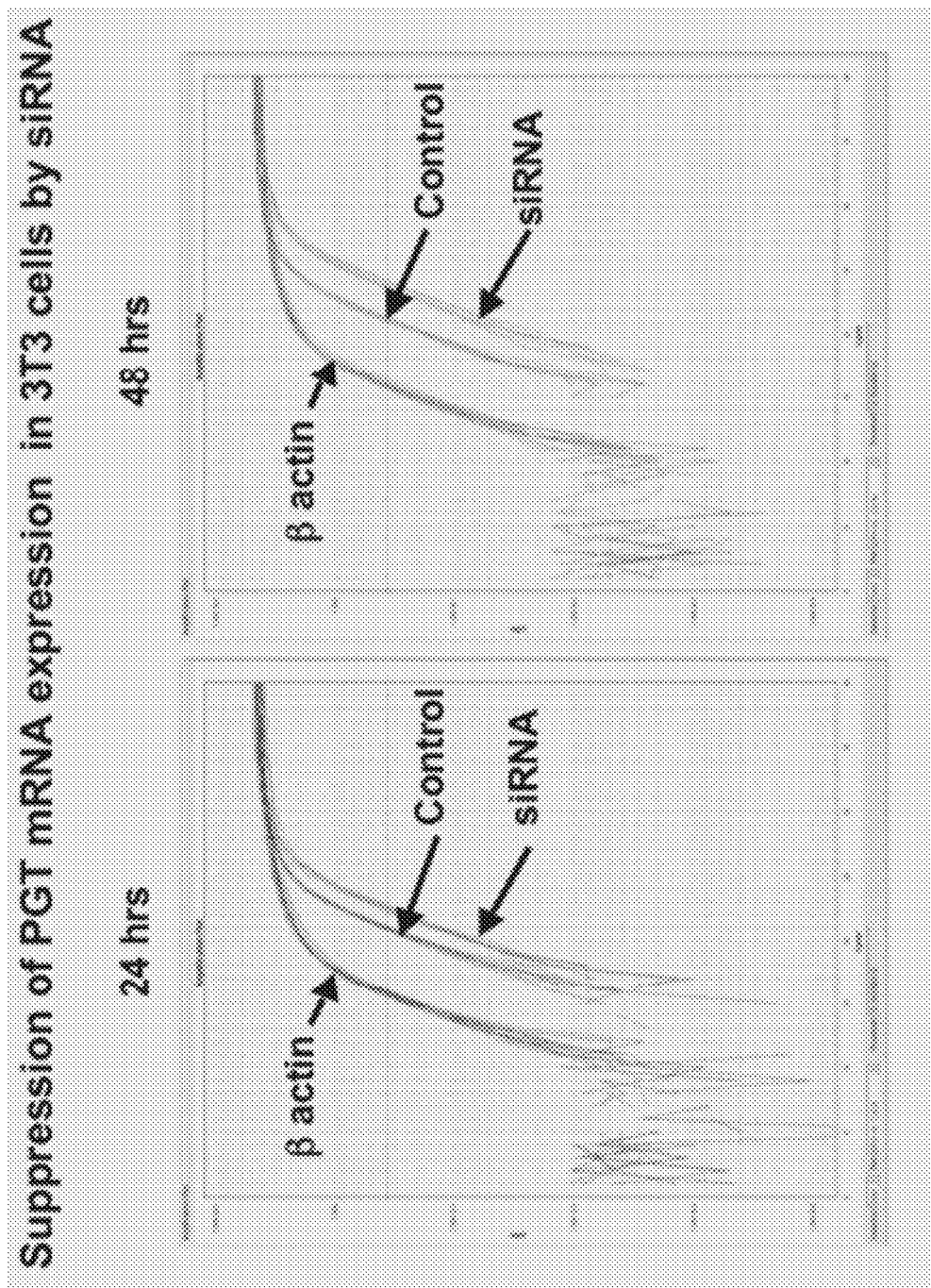
FIG. 13 shows the knock-down of PGT mRNA expression in Swiss 3T3 fibroblasts. At each of the two time points, the left curve depicts amplification of β-actin in both control and mPGT siRNA transfected cells; the middle curves represent amplification of PGT mPGT mRNA in control cells; and the right curves represent amplification of PGT mPGT mRNA derived from siRNA-transfected cells. A shift to the right in a curve means that a higher number of PCR cycles is required for amplification, indicating a lower starting concentration of template (i.e. PGT mRNA).

The utility of siRNA for reducing PGT mRNA expression was also evaluated. Cells were transfected with Qiagen siRNA oligonucleotides directed against PGT or against no known gene sequence (manufacturer's control). Total RNA was extracted 24 or 48 hrs later and subjected to Quantitative (Real Time) PCR. As shown in FIG. 13, the siRNA was effective in reducing PCT mRNA expression.

Figure 14:
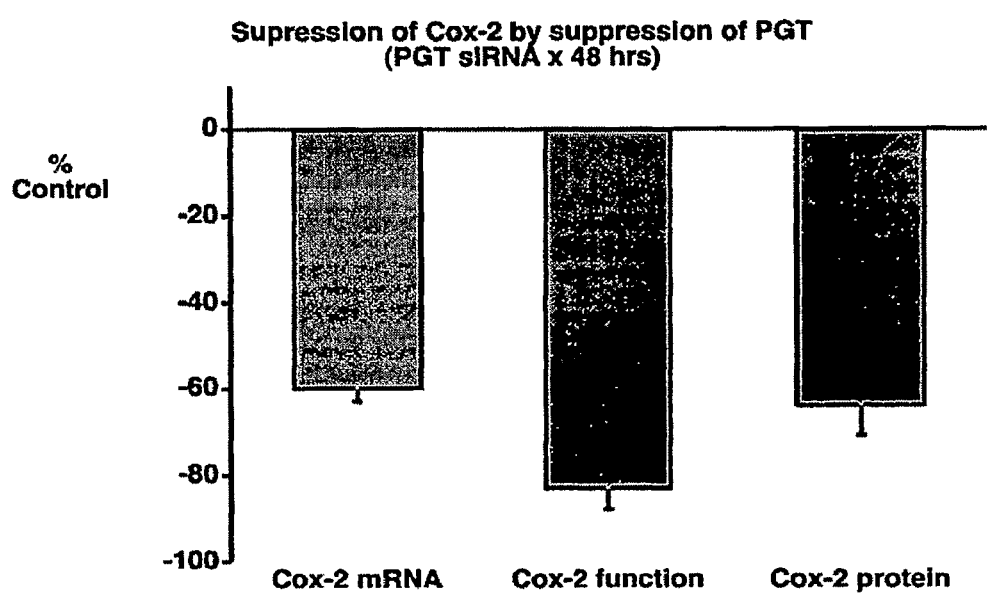
FIG. 14 is a graph of experimental results showing the inhibition of Cox-2 in Swiss 3T3 cells by suppression of PGT.

Further studies evaluated the effect of PGT inhibition on Cox-2 expression. Cells were treated with siRNA to PGT as in FIG. 13 and were harvested at 48 hrs. Cox-2 mRNA was quantified by Quantitative (Real Time) PCR (left). Cox-2 function was determined by stimulating PGE2 release with the calcium ionophore A23187±the nonselective inhibitor indomethacin or the Cox-2 selective inhibitor NS 398. Cox-2 protein was determined by immunoblotting using a polyclonal antibody (Cayman Chemicak, Inc.). As shown in FIG. 14, inhibition of PGT led to suppression of Cox-2 expression in these cells.

Example 3

Physiological Studies with PGT Inhibitor T26A

The effects of T26A (see Example 2) on rat physiology was evaluated.

T26A Increases Endogenous $PGE_2$ in Circulating Blood of Rats.

Figure 15:
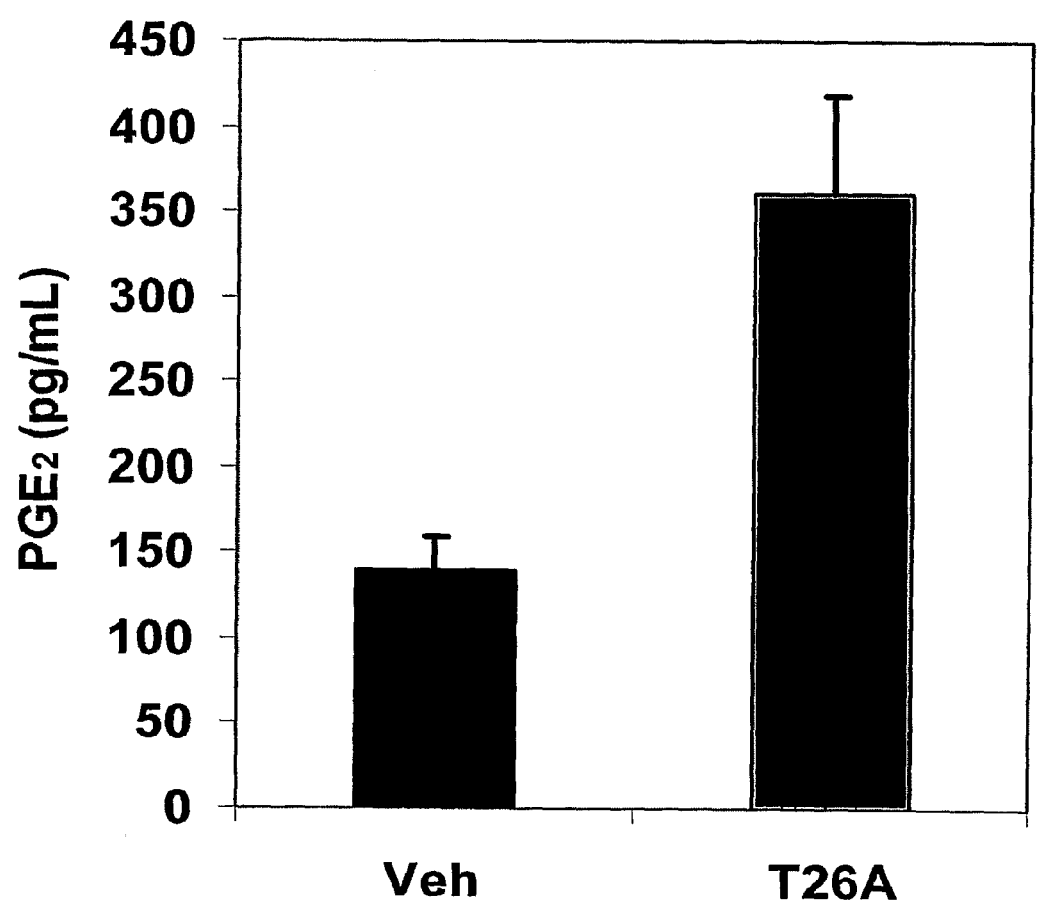
FIG. 15 is a graph showing that T26A increases endogenous PGE$_2$ in circulating blood of rats.

Either 300 µL vehicle (4% DMSO and 4% cremophor in water) or 300 µL of 1 mM T26A was injected into the jugular vein of anesthetized rats (300-325 g weight). One mL of blood was obtained from the carotid artery 10 minutes later, $PGE_2$ in blood samples was measured using $PGE_2$ EIA kit from Caymanchem. FIG. 15 shows the results graphically. The acute administration of T26A (i.e., by injection) caused a greater than two-fold increase in plasma $PGE_2$ concentrations. This finding is consistent with the model advanced in Example 2 (FIG. 8). Since PGT transports $PGE_2$ into the cell, inhibiting PGT would be expected to inhibit removal of $PGE_2$ from blood to be internalized and degraded.

T26A Reduces the Degradation of Exogenously-Administered $PGE_2$.

Figure 16:
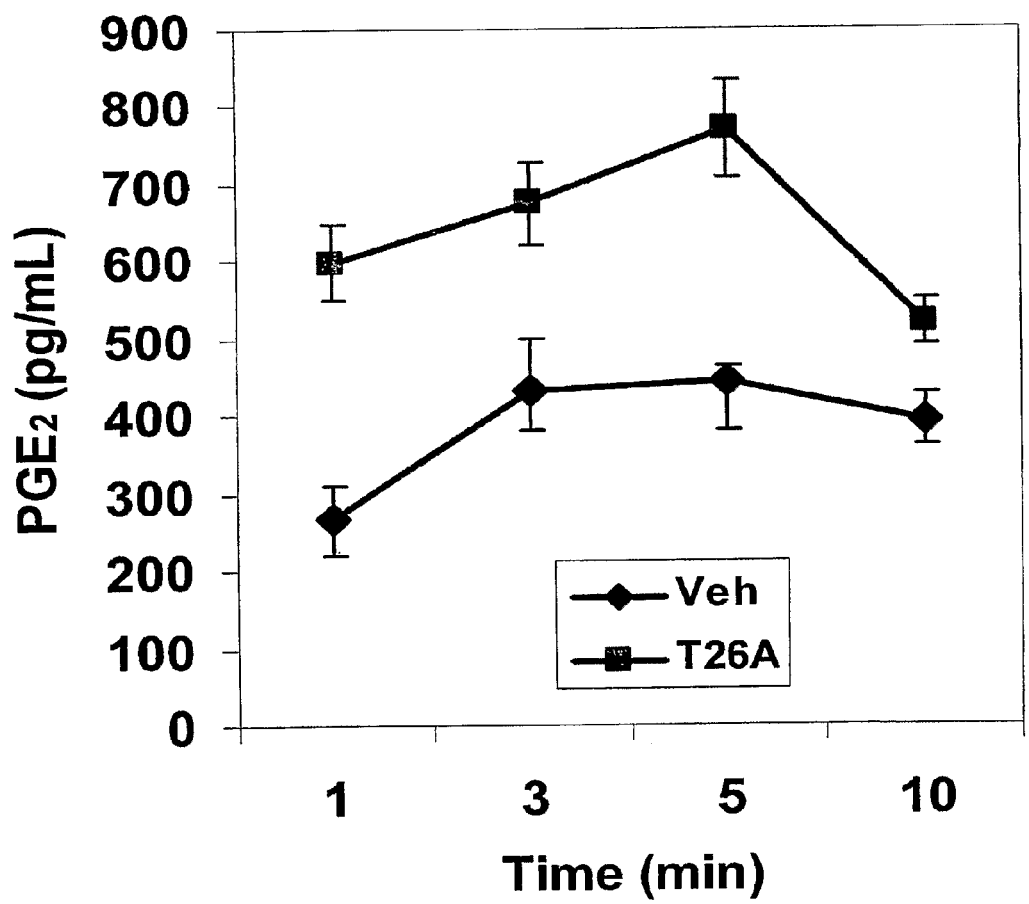
FIG. 16 is a graph showing that T26A reduces the degradation of exogenously-administered PGE$_2$.

Either 300 µL vehicle (4% DMSO and 4% cremophor in water) or 300 µL of 1 mM T26A was injected into the jugular vein of anesthetized rats (300-325 g weight). Ten minutes later 100 µL of 1 ng/µL $PGE_2$ was injected. One mL blood was withdrawn from the carotid artery at 1, 3, 5, and 10 min after $PGE_2$ injection. $PGE_2$ in blood samples was measured using $PGE_2$ EIA kit from Caymanchem. FIG. 16 shows the results graphically. The acute administration of T26A inhibited $PGE_2$ degradation. This is also consistent with the FIG. 8 model. Inhibiting $PGE_2$ transport into the cell reduces its intracellular degradation.

Chronic Oral Administration of T26A Increases Endogenous $PGE_2$ in Whole Blood.

Figure 17:
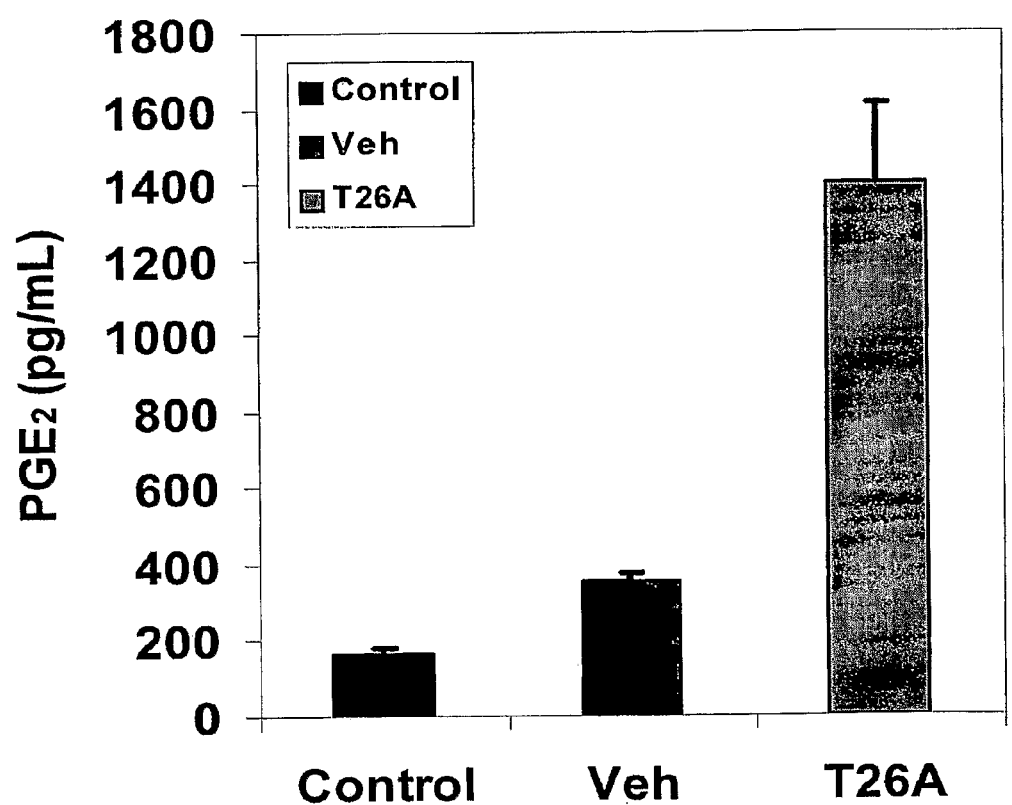
FIG. 17 is a graph showing that chronic oral administration of T26A increases endogenous PGD$_2$ in whole blood.

Regular water, vehicle (2% DMSO and 2% cremophor) in drinking water, or 2 mM T26A in drinking water was administered to 17 week old mice for 16 days. At the end of the experiment, we withdrew blood by cardiac puncture. $PGE_2$ in blood samples was measured by using $PGE_2$ EIA kit from Caymanchem. FIG. 17 shows the results graphically. Chronic oral administration increased plasma $PGE_2$ levels four-fold. This indicates that T26A is effective when administered orally.

Chronic Oral Administration of T26A Increases $PGE_2$ Excretion in Urine.

Figure 18:
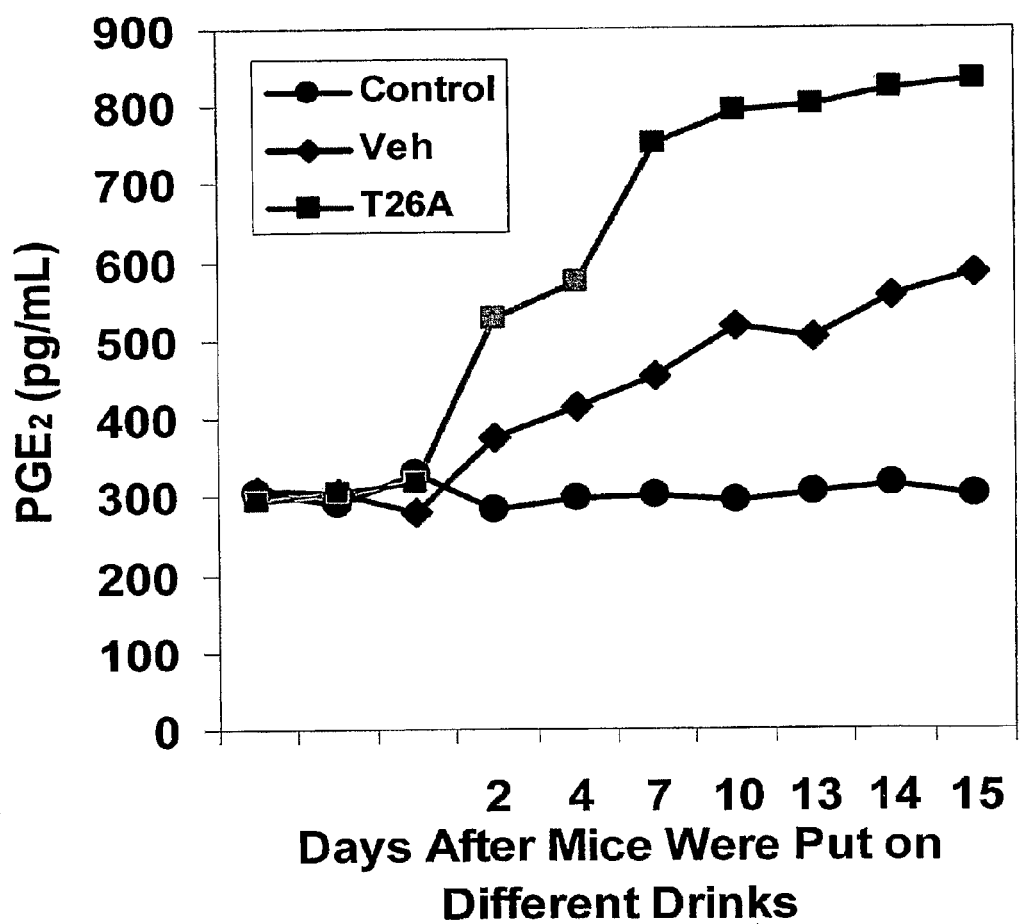
FIG. 18 is a graph showing that chronic oral administration of T26A increases PGE$_2$ excretion in urine.

The mice described above pertaining to FIG. 17 were placed in metabolic cages. Six days after they adjusted to the caged condition (on regular diet and water) regular drinking water, vehicle (2% DMSO and 2% cremophor) in drinking water, or 2 mM T26A in drinking water was administered for 16 days. Urine was collected daily. $PGE_2$ in urine samples was measured using $PGE_2$ EIA kit from Caymanchem. FIG. 18 shows the results graphically. Chronic oral administration of T26A increased urinary excretion of endogenous $PGE_2$. This is also consistent with the FIG. 8 model. Inhibiting $PGE_2$ transport into the cell reduces its intracellular degradation such that more is secreted without intracellular degradation.

Chronic Oral Administration of T26A Increases Bleeding Time.

At the end of the experiment shown in FIGS. 17-18, bleeding time was measured using the tail cut method. About 1 cm tails of restrained mice were cut off; the diameter of the cut was kept the same for all mice. The emerging blood was blotted every 15 seconds without touching the wound. Bleeding time was measured as the point at which bleeding had stopped for 1 minute. Results are shown graphically in FIG. 19. Orally administered T26A increased bleeding time. It is believed that the blockade of endothelial PCT allows intravascular accumulation of PGE2 or prostacyclin, either of which can inhibit platelet aggregation.

T26A Appears to be Well-Tolerated in Mice.

Table 3 shows treatments and data collected for toxicity studies.

TABLE 3

In vivo test of acute T26A toxicity.

| Mouse | Body Weight (g) | Injection | Condition |
|---|---|---|---|
| 1 | 23.3 | 100% DMSO | Rarely moved for the first three hours. |
| 2 | 25.6 | 25 mM T26A, 5% DMSO, 5% Cremophor in water | More active than mice #1, #4 and #5, but moved slowly for the first one hour. Appeared normal after 1 hour. |
| 3 | 24.7 | 25 mM T26A, 5% DMSO, 5% Cremophor in water | More actively than mice #1, #4 and #5, but moved slowly for the first one hour. Appeared normal after 1 hour. |
| 4 | 24.8 | 250 mM T26A in 100% DMSO | Rarely moved for the first three hours. Appeared normal afterwards. |
| 5 | 24.0 | 250 mM T26A in 100% DMSO | Rarely moved for the first three hours. Appeared normal afterwards. |
| 6 | 21.9 | 6 mM T26A, 3% DMSO, 3% Cremophor in water | Appeared normal. |
| 7 | 22.1 | 6 mM T26A, 3% DMSO, 3% Cremophor in water | Appeared normal. |
| 8 | 20.6 | 6 mM T26A, 3% DMSO, 3% Cremophor in water | Appeared normal. |
| 9 | 21.0 | 10% DMSO, 10% Cremophor in water | Appeared normal. |
| 10 | 22.2 | No injection | Normal. |

All mice were male. They received one intraperitoneal injection. The injected volume was 100 uL to all of them, 14 hours after injection, they were all alive, and moved and acted normally.

Figure 19:
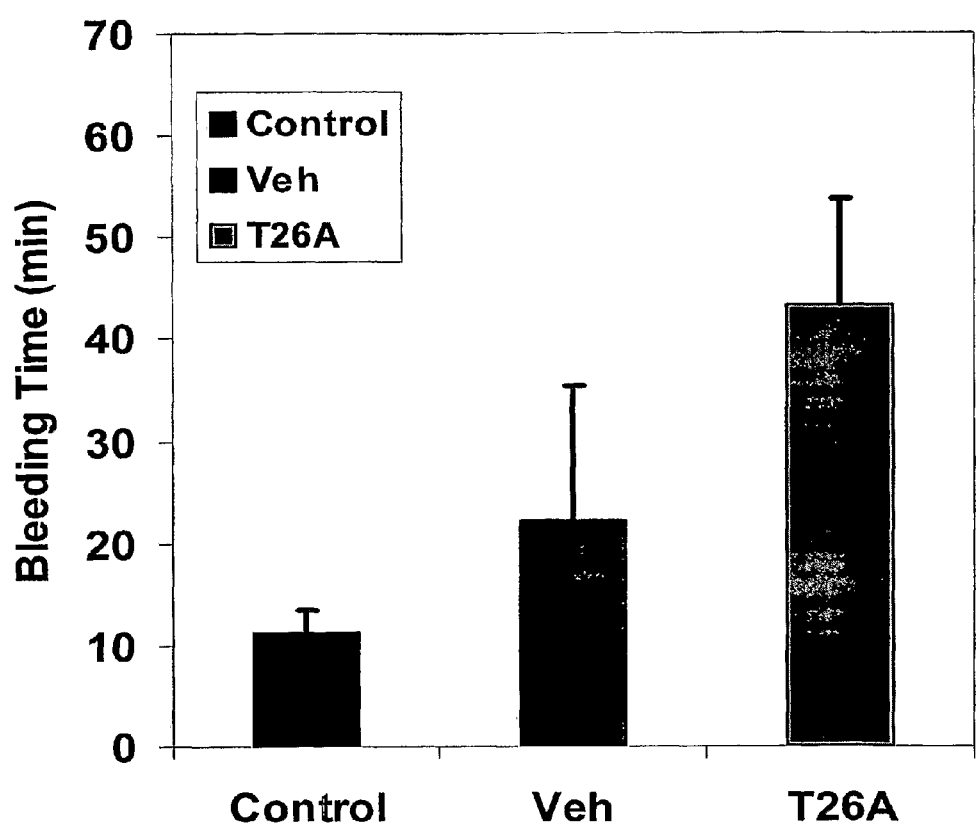
FIG. 19 is a graph showing that chronic oral administration of T26A increases bleeding time.

The mice described in FIGS. 17-19 were studied in metabolic cages. Six days after they adjusted to the caged condition on regular diet and water, regular drinking water, or vehicle (2% DMSO and 2% cremophor) in drinking water, or 2 mM T26A in drinking water was administered for 16 days. Their water and food intake, weight body and urine volume were recorded daily. Results are shown graphically in FIG. 20. Chronic oral administration of T26A did not have any observable effects on water and food intake, body weight, or daily urine volume.

Figure 21:
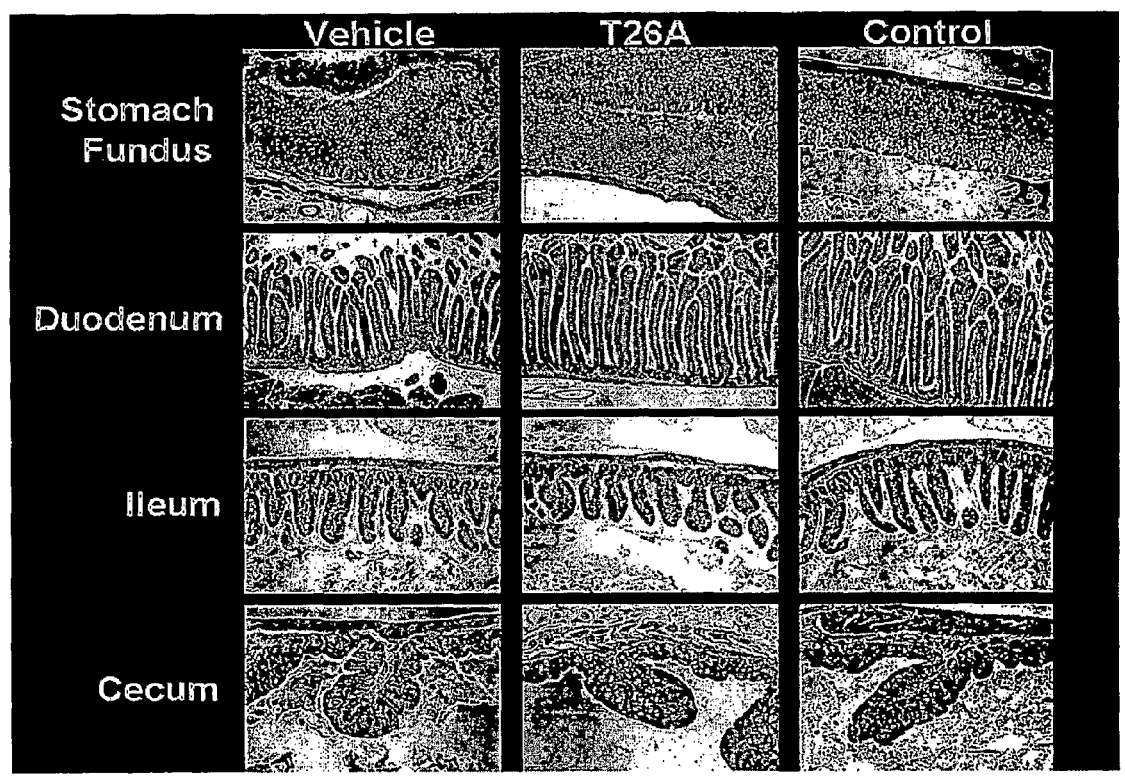
FIG. 21 is micrographs of stained tissue sections showing that chronic oral administration of T26 apparently does not cause any pathological damage to the gastrointestinal tract.

FIG. 21 provides results of post-mortem studies on the mice of FIGS. 17-19 administered either regular drinking water, or vehicle (2% DMSO and 2% cremophor) in drinking water, or 2 mM T26A in drinking water for 16 days. At the end of experiments, we isolated tissues from the mice and made H&E stained slides of tissues and examined the tissues microscopically. Chronic oral administration of T26A did not cause any pathological damage to the gastrointestinal tract.

Conclusion:

T26A appears to be non-toxic when administered on a chronic oral basis in doses sufficient to raise plasma and urinary $PGE_2$ concentrations.

REFERENCES

Alm A (1998) Prostaglandin derivates as ocular hypotensive agents. *Progress in Retinal and Eye Research* 17:291-312.

Banu S K, Arosh J A, Chapdelaine P and Fortier M A (2003) Molecular cloning and spatio-temporal expression of the prostaglandin transporter: a basis for the action of prostaglandins in the bovine reproductive system. *Proc Natl Acad Sci USA* 100:11747-11752.

Bao Y, Pucci M L, Chan B S, Lu R, Ito S and Schuster V L (2002) Prostaglandin transporter PGT is expressed in cell types that synthesize and release prostanoids. *American Journal of Physiology* 282:F11103-1110.

Bito L Z and Salvador E V (1976) Effects of anti-inflammatory agents and some other drugs on prostaglandin biotransport. *J. Pharmacol. Exp. Ther.* 198:481-488.

Blatteis C M and Sehic E (1997) Fever: How may circulating pyrogens signal the brain? *News in Physiological Sciences.* 12:1-9.

Bley K R, Hunter J C, Eglen R M and Smith J A (1998) The role of IP prostanoid receptors in inflammatory pain. *Trends Pharmacol Sci* 19:141-147.

Bark J T, Lee J W, Khersonsky S M, Moon H S and Chang Y T (2003a) Novel orthogonal strategy toward solid-phase synthesis of 1,3,5-substituted triazines. *Org Lett* 5:117-120.

Bork J Y, Lee J W and Chang Y T (2003b) Palladium-catalyzed cross-coupling reaction of resin-bound chlorotriazines, *Tetrahedron Letters* 44:6141-6144.

Bos C L, Richel D J, Ritsema T, Peppelenbosch M P and Versteeg H H (2004) Prostanoids and prostanoid receptors in signal transduction. *Int J Biochem Cell Biol* 36:1187-1205.

Chan B S, Endo S, Kanai N and Schuster V L (2002) Identification of lactate as a driving force for prostanoid transport by prostaglandin transporter PGT. *Am J Physiol* 282: F1097-F1102.

Chan B S, Satriano J A, Pucci M L and Schuster V L (1998) Mechanism of prostaglandin E2 transport across the plasma membrane of HeLa cells and *Xenopus oocytes* expressing the prostaglandin transporter "PGT". *J Biol Chem* 273:6689-6697.

Clyman R I, Mauray F, Roman C and Rudolph A M (1978) PGE2 is a more potent vasodilator of the lamb ductus arteriosus than is either PGI2 or 6 keto PGFIalpha. *Prostaglandins* 16:259-264, Coceani F and Olley P M (1988) The control of cardiovascular shunts in the fetal and perinatal period. *Can J Physiol Pharmacol* 66:1129-1134.

Eling T E, Hawkins H J and Anderson M W (1977) Structural requirements for, and the effects of chemicals on, the rat pulmonary inactivation of prostaglandins. *Prostaglandins* 14:51-60.

Endo S, Nomura T, Chan B S, Lu R, Pucci M L, Bao Y and Schuster V L (2002) Expression of PGT in MDCK cell monolayers: polarized apical localization and induction of active PG transport. *American Journal of Physiology* 282: F618-F622.

Epstein M (1986) *Prostaglandins and the kidney. American journal of medicine*; v. 80, no. IA, 1986. Technical Publishing, New York, N.Y.

Funk C D (2001) Prostaglandins and leukotrienes: advances in eicosanoid biology. *Science* 294: 871-1875.

Helliwell R J, Adams L F and Mitchell M D (2004) Prostaglandin synthases: recent developments and a novel hypothesis. *Prostaglandins Leukotrienes and Essential Fatty Acids* 70:101-113.

Hill D A, Chiosea S, Jamaluddin S, Roy K, Fischer A H, Boyd D D, Nickerson J A and Imbalzano A N (2004) Inducible changes in cell size and attachment area due to expression of a mutant SWI/SNF chromatin remodeling enzyme. *J Cell Sci* 117:5847-5854.

Jacquemin E, Hagenbuch B, Stieger B, Wolkoff A W and Meier P J (1994) Expression cloning of a rat liver Na+-independent organic anion transporter. *Proc Natl Acad Sci USA* 91:133-137.

Kanai N, Lu R, Satriano J A, Bao Y, Wolkoff A W and Schuster V L (1995) Identification and characterization of a prostaglandin transporter. *Science* 268:866-869.

Khersonsky S M, Jung D W, Kang T W, Walsh D P, Moon H S, Jo H, Jacobson E M, Shetty V, Neubert T A and Chang Y T (2003) Facilitated forward chemical genetics using a tagged triazine library and zebrafish embryo screening. *J Am Chem Soc* 125:11804-11805.

Moon H S, Jacobson E M, Khersonsky S M, Luzung M R, Walsh D P, Xiong W, Lee J W, Parikh P B, Lam J C, Kang T W, Rosania G R, Schier A F and Chang Y T (2002) A novel microtubule destabilizing entity from orthogonal synthesis of triazine library and zebrafish embryo screening. *J Am Chem Soc* 124:11608-11609.

Narumiya S, Sugimoto Y and Ushikubi F (1999) Prostanoid receptors: structures, properties, and functions. *Physiological Reviews* 79:1193-1226.

Negishi M, Ito S, Tanaka T, Yokohama H, Hayashi H, Katada T, Ui M, and Hayaishi O (1987) Covalent cross-linking of prostaglandin E receptor from bovine adrenal medulla with a pertussis toxin-insensitive guanine nucleotide-binding protein. *J Biol Chem* 262:12077-12084.

Nishigaki N, Negishi M, and Ichikawa A (1996) Two Gs-coupled prostaglandin E receptor subtypes, EP2 and EP4, differ in desensitization and sensitivity to the metabolic inactivation of the agonist. *Mol Pharmacol* 50:1031-1037.

Nomura T, Lu R, Pucci M L and Schuster V L (2004) The two-step model of prostaglandin signal termination: in vitro reconstitution with the prostaglandin transporter and prostaglandin 15 dehydrogenase. *Mol Pharmacol* 65:973-978.

Reid G, Wieling a P, Zelcer N, van der Heijden I, Kuil A, de Haas M, Wijnholds J and Borst P (2003) The human multidrug resistance protein MRP4 functions as a prostaglandin efflux transporter and is inhibited by nonsteroidal anti inflammatory drugs. *Proc Natl Acad Sci USA* 100:9244-9249.

Samad T A, Sapirstein A and Woolf C J (2002) Prostanoids and pain: unraveling mechanisms and revealing therapeutic targets. *Trends Mol Med* 8:390-396.

Schneider S W, Pagel P, Rotsch C, Danker T, Oberleithner H, Radmacher M and Schwab A (2000) Volume dynamics in migrating epithelial cells measured with atomic force microscopy. *Pflugers Arch* 439:297-303.

Schuster V L (1998) Molecular mechanisms of prostaglandin transport. *Ann Review of Physiology* 60:221-242.

Schuster V L (2002) Prostaglandin Transport. *Prostaglandins and Other Lipid Mediators* 68-69:633-647.

Schuster V L, Itoh S, Andrews S W, Burk R M, Chen J, Kedzie K M, Gil D W and Woodward D F (2000) Synthetic modification of prostaglandin f(2alpha) indicates different structural determinants for binding to the prostaglandin f receptor versus the prostaglandin transporter. *Molecular Pharmacology* 58:1511-1516.

Smith G C S, Coleman R A and McGrath J C (1994) Characterization of dilator prostanoid receptors in the fetal rabbit ductus arteriosus. *Journal of Pharmacology & Experimental Therapeutics* 271:390-396.

Stjernschantz J (1995) Prostaglandins as ocular hypotensive agents; development of an analogue for glaucoma treatment. *Advances in Prostaglandin Thromboxane and Leukotriene Research* 23:63-68.

Stjernschantz J (2004) Studies on ocular inflammation and development of a prostaglandin analogue for glaucoma treatment. *Experimental Eye Research* 78:759-766.

Susanna R, Jr., Chew P and Kitazawa Y (2002) Current status of prostaglandin therapy: latanoprost and unoprostone. *Survey in Ophthalmology* 47 Suppl 1:S97-104.

Sweet D H, Wolff N A and Pritchard J B (1997) Expression cloning and characterization of ROAT1. The basolateral organic anion transporter in rat kidney. *J. Biol. Chem.* 272:30088-30095.

Ulmann A, Silvestre L, Chemama L, Rezvani Y, Renault M, Aguiliaume C J. and Baulieu E E (1992) Medical termination of early pregnancy with mifepristone (RU 486) followed by a prostaglandin analogue. Study in 16,369 women. *Acta Obstet. Gynec. Scand.* 71:278-283.

Uttamchandani M, Walsh D P, Khersonsky S M, Huang X, Yao S Q and Chang V T (2004) Microarrays of tagged combinatorial triazine libraries in the discovery of small-molecule ligands of human IgG. *J Comb Chem* 6:862-868.

Vanegas H and Schaible H G (2001) Prostaglandins and cyclooxygenases [correction of cycloxygenases] in the spinal cord. *Prog Neurobiol* 64:327-363.

Wang J L, Cheng H F, Zhang M Z, McKanna J A and Harris R C (1998) Selective increase of cyclooxygenase-2 expression in a model of renal ablation. *Am. J. Physiol.* 275:F613-F622.

Yokoyama C, Yabuki T, Shimonishi M, Wada M, Hatae T, Ohkawara S, Takeda J, Kinoshita T, Okabe M and Tanabe T (2002) Prostacyclin-deficient mice develop ischemic renal disorders, including nephrosclerosis and renal infarction. *Circulation* 106:2397-2403.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A compound having the structure:

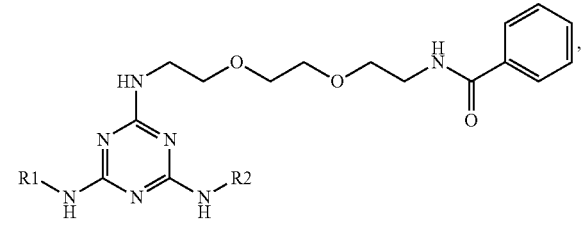

wherein R1 is:

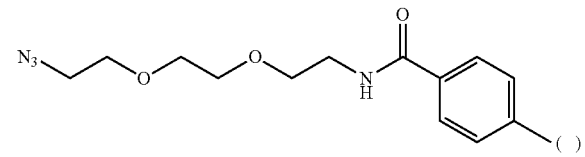

and wherein R2 is:

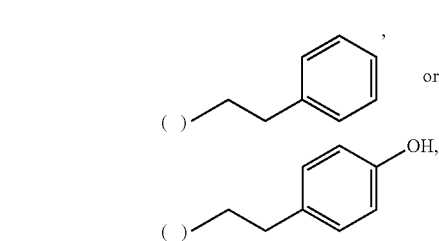

or a pharmaceutically acceptable salt, ester or tautomer thereof.

2. The compound of claim 1 having the structure:
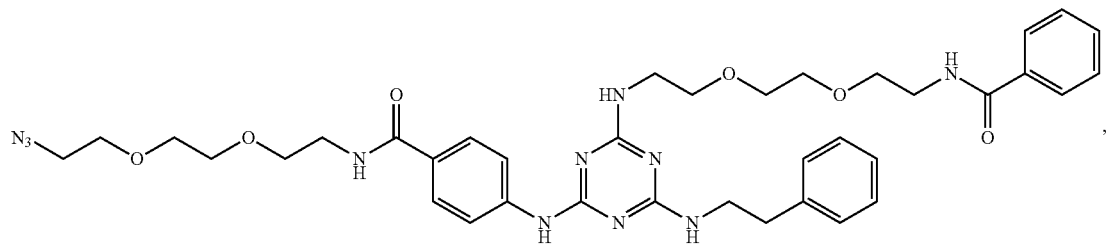 [SMILES: [N-]=[N+]=NCCOCCOCCNC(=O)c1ccc(Nc2nc(NCCOCCOCCNC(=O)c3ccccc3)nc(NCCc3ccccc3)n2)cc1]
or a pharmaceutically acceptable salt thereof.
3. The compound of claim 1 having the structure:
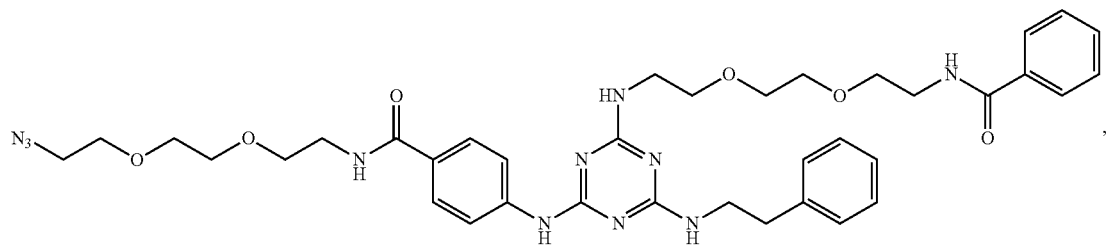 [SMILES: [N-]=[N+]=NCCOCCOCCNC(=O)c1ccc(Nc2nc(NCCOCCOCCNC(=O)c3ccccc3)nc(NCCc3ccccc3)n2)cc1]
or a pharmaceutically acceptable salt thereof.
4. The compound of claim 2 which is:
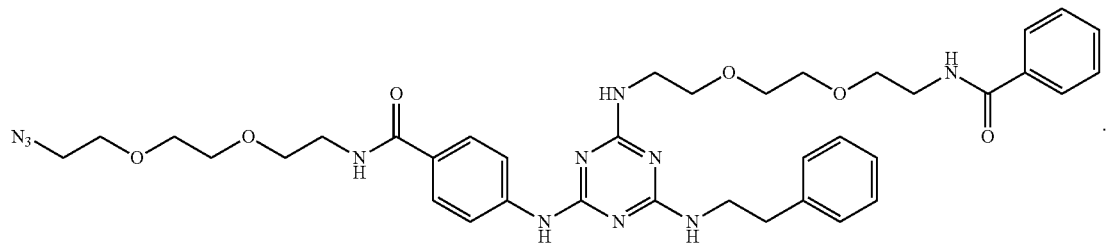 [SMILES: [N-]=[N+]=NCCOCCOCCNC(=O)c1ccc(Nc2nc(NCCOCCOCCNC(=O)c3ccccc3)nc(NCCc3ccccc3)n2)cc1]
5. The compound of claim 3 which is:
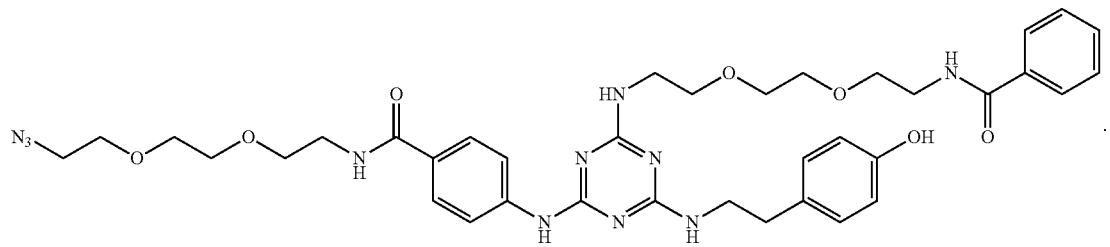 [SMILES: [N-]=[N+]=NCCOCCOCCNC(=O)c1ccc(Nc2nc(NCCOCCOCCNC(=O)c3ccccc3)nc(NCCc3ccc(O)cc3)n2)cc1]
6. A composition comprising the compound of claim 1 in a pharmaceutically acceptable excipient.
* * * * *